United States Patent
Love et al.

(10) Patent No.: US 11,767,557 B2
(45) Date of Patent: Sep. 26, 2023

(54) SINGLE CELL ANALYSES

(71) Applicant: Massachusetts Institute of Technology, Cambridge, MA (US)

(72) Inventors: J. Christopher Love, Somerville, MA (US); Todd Michael Gierahn, Brookline, MA (US); Alexander K. Shalek, Lexington, MA (US); Marc Havens Wadsworth, Somerville, MA (US); Travis K. Hughes, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 255 days.

(21) Appl. No.: 16/213,551

(22) Filed: Dec. 7, 2018

(65) Prior Publication Data
US 2019/0218607 A1 Jul. 18, 2019

Related U.S. Application Data

(60) Provisional application No. 62/595,895, filed on Dec. 7, 2017.

(51) Int. Cl.
| | | |
|---|---|---|
| *C12Q 1/6874* | (2018.01) | |
| *C12Q 1/6806* | (2018.01) | |
| *C12N 15/10* | (2006.01) | |
| *G03F 7/20* | (2006.01) | |
| *B01L 3/00* | (2006.01) | |

(52) U.S. Cl.
CPC .......... *C12Q 1/6874* (2013.01); *B01L 3/5085* (2013.01); *C12N 15/1068* (2013.01); *C12N 15/1093* (2013.01); *C12N 15/1096* (2013.01); *C12Q 1/6806* (2013.01); *G03F 7/2014* (2013.01); *B01L 2200/0647* (2013.01); *B01L 2300/0681* (2013.01); *B01L 2300/0819* (2013.01); *B01L 2300/0829* (2013.01); *B01L 2300/0851* (2013.01)

(58) Field of Classification Search
CPC ................ C12Q 1/6874; C12Q 1/6806; C12N 15/1068; C12N 15/1093; C12N 15/1096
See application file for complete search history.

(56) References Cited

U.S. PATENT DOCUMENTS

| | | |
|---|---|---|
| 5,939,291 A * | 8/1999 | Loewy et al. ............... 435/91.2 |
| 7,393,665 B2 | 7/2008 | Brenner |
| 8,148,068 B2 | 4/2012 | Brenner |
| 9,194,001 B2 | 11/2015 | Brenner |
| 9,512,478 B2 | 12/2016 | Bignell et al. |
| 9,567,645 B2 | 2/2017 | Fan et al. |
| 9,708,654 B2 | 7/2017 | Hunicke-Smith et al. |
| 9,783,847 B2 | 10/2017 | Chee |
| 9,816,137 B2 | 11/2017 | Fodor et al. |
| 10,273,541 B2 | 4/2019 | Hindson et al. |
| 10,590,483 B2 | 3/2020 | Vigneault et al. |
| 10,612,088 B2 | 4/2020 | Shishkin et al. |
| 10,633,702 B2 | 4/2020 | Brenner et al. |
| 10,711,296 B2 | 7/2020 | Heuermann et al. |
| 10,752,895 B2 | 8/2020 | Church et al. |
| 2007/0292837 A1 * | 12/2007 | Deutsch et al. .................. 435/4 |
| 2009/0099040 A1 * | 4/2009 | Ward et al. ..................... 506/26 |
| 2013/0130923 A1 * | 5/2013 | Erlich et al. ........... C12Q 1/686 |
| 2014/0213485 A1 | 7/2014 | Weissman et al. |
| 2015/0368719 A1 * | 12/2015 | Regev et al. ........ C12Q 1/6883 |
| 2018/0030515 A1 * | 2/2018 | Regev et al. ........ C12Q 1/6809 |
| 2018/0179579 A1 * | 6/2018 | Vollmers et al. .... C12Q 1/6806 |
| 2019/0127782 A1 | 5/2019 | Regev et al. |

FOREIGN PATENT DOCUMENTS

| | | |
|---|---|---|
| EP | 2414548 | 2/2012 |
| JP | 2002-065263 A | 3/2002 |
| JP | 2006-519621 A | 8/2006 |
| JP | 2007-504831 A | 3/2007 |
| JP | 2016-533187 A | 10/2016 |
| JP | 2017-507663 A | 3/2017 |
| WO | WO 2004/081225 A2 | 9/2004 |
| WO | WO 2005/042759 A2 | 5/2005 |
| WO | WO 2015-031691 A | 3/2015 |
| WO | WO 2015/014307 A1 | 9/2015 |
| WO | WO 2016/038670 A2 | 3/2016 |
| WO | WO 2016/138500 A1 | 9/2016 |

OTHER PUBLICATIONS

Invitation to Pay Additional Fees dated Mar. 18, 2019, for Application No. PCT/US2018/064494.
International Search Report and Written Opinion dated May 10, 2019, for Application No. PCT/US2018/064494.
International Preliminary Report on Patentability dated Jun. 18, 2020, for Application No. PCT/US2018/064494.
[No Author Listed], Microbiology. Shen, ed. Higher Education Press. Jul. 2000; p. 269, 18 pages.

* cited by examiner

*Primary Examiner* — Kaijiang Zhang
(74) *Attorney, Agent, or Firm* — Wolf, Greenfield & Sacks, P.C.

(57) ABSTRACT

Modifications to both hardware and enzymatic reactions used in single cell analyses such as but not limited to Seq-well that enable significant increases in the yield of transcripts per cell, portability and ease of use, increased scalability of the assay, and linkage of transcript information to other measurements made in the picowell arrays are disclosed.

17 Claims, 28 Drawing Sheets

Specification includes a Sequence Listing.

 
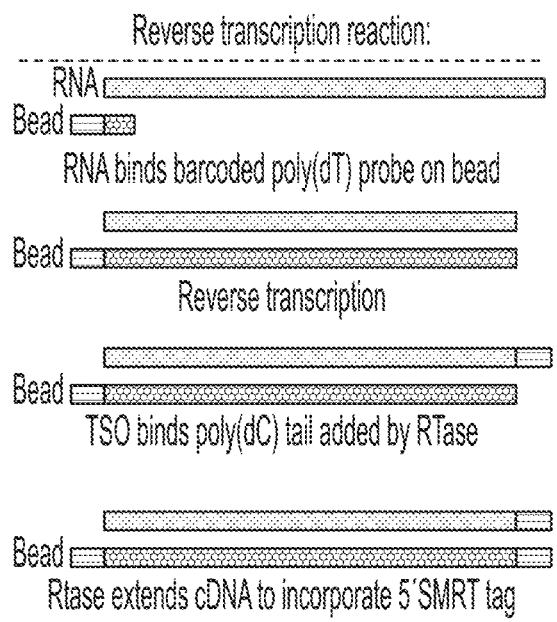 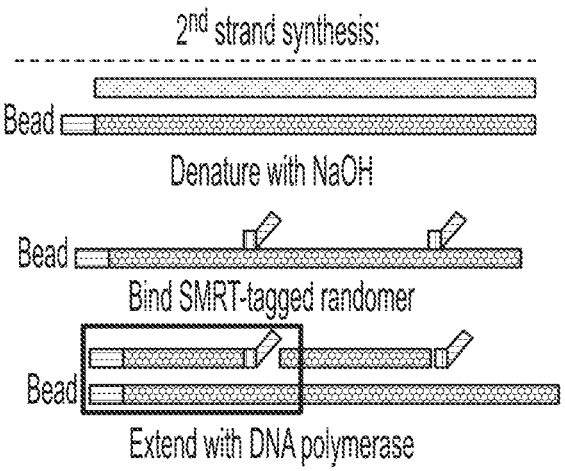
FIG. 2A
FIG. 2B
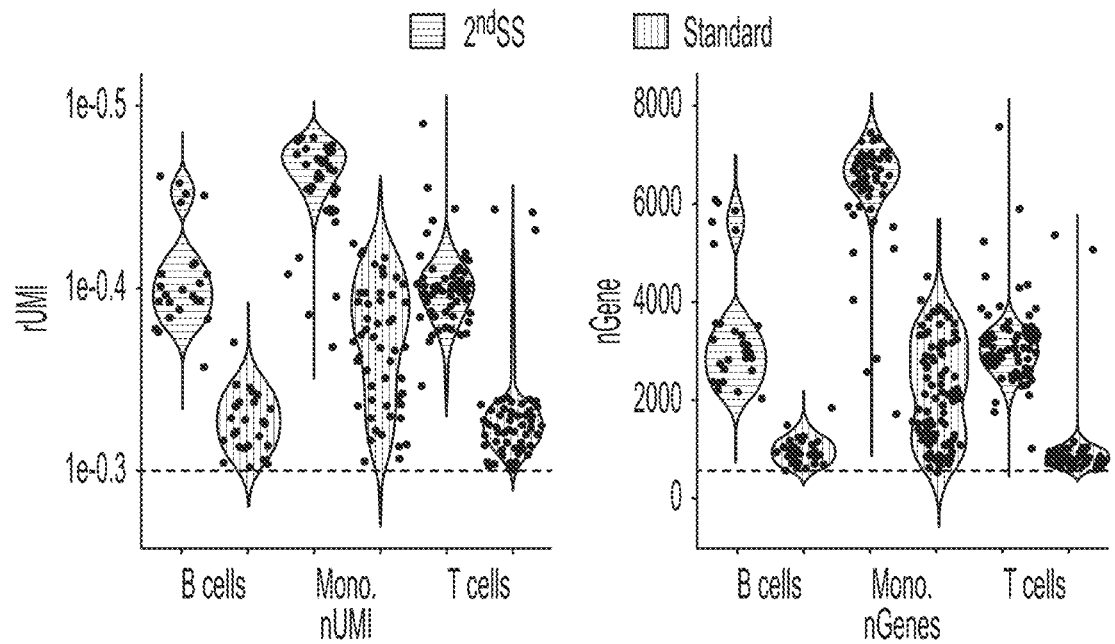
FIG. 2C 200 microns

SINGLE CELL ANALYSES

RELATED APPLICATIONS

This application claims priority under 35 U.S.C. § 119(e) to U.S. Provisional Application No. 62/595,895, filed Dec. 7, 2017 and entitled "SINGLE CELL ANALYSES," which is incorporated herein by reference in its entirety for all purposes.

FEDERALLY SPONSORED RESEARCH

This invention was made with Government support under GM119419, DK097681 and P01 AI045757 awarded by the National Institutes of Health, and under Grant No. W911NF-13-D-0001 awarded by the Army Research Office. The Government has certain rights in the invention.

BACKGROUND OF INVENTION

The well-based biological analysis platform, also referred to as Seq-well, facilitates the creation of barcoded single-cell sequencing libraries from thousands of single cells using devices that contain 10,000-1,000,000 or more wells of micron dimensions and picoliter volumes preloaded with barcoded transcript-capture beads. Cells are simply applied to the top surface of the array and drop into the wells by gravity within minutes. This simplified loading scheme enables Seq-well to capture nearly 100% of cells applied to the surface of the device. Key to the robust capture of single cell transcriptomes by Seq-well is the attachment of a semi-permeable membrane to the array surface after cell loading (as disclosed in published PCT Application No. PCT/US17/13791), enabling facile buffer exchange within the wells for cell lysis and RNA hybridization while retaining biologic macromolecules (e.g., DNA, RNA, and protein) for capture. Due to its low input requirements and efficient capture of beads and cells, the Seq-well platform has broad application in numerous research and clinical settings. While the platform has been optimized for the generation of individually barcoded single-cell sequencing libraries following confinement of cells and mRNA capture beads (Macosko, et al. 2015), it is capable of multiple levels of data acquisition. The platform is compatible with other assays and measurements performed with the same array. Levels of cell surface proteins (Ogunniyi, A. O., B. A. Thomas, T. J. Politano, N. Varadarajan, E. Landais, P. Poignard, B. D. Walker, D. S. Kwon, and J. C. Love, "Profiling Human Antibody Responses by Integrated Single-Cell Analysis" Vaccine, 32(24), 2866-2873), secreted proteins (see, e.g., U.S. Pat. Nos. 7,776,553; 8,835,187; 8,772,049; 8,865,479; JP 571822; EP 2 297 333; US Publication No. 2012/0015824), cytolytic behaviors of cells (see, e.g., US Publication No. 2012/0149592), dynamic motility (see, e.g., Yao, X. et al. Functional analysis of single cells identifies a rare subset of circulating tumor cells with malignant traits. Integr Biol (Camb), doi:10.1039/c3ib40264a (2014), and gene expression (see, e.g., US Publication No. 2011/0111981) can be assessed using confined volume technologies. However, these additional measures have not been linked to the full transcriptome of each cell because the random nature of the barcoded bead loading process prevents linking a bead barcode in sequencing space back to its well of origin.

SUMMARY OF INVENTION

This disclosure therefore provides improved products and methods for use in single cell analytics. These improved products and methods are useful in well-based assays and/or bead-based assays such as but not limited to the Seq-well assays. They improve the robustness of such assays, for example by increasing the proportion of single cell transcripts that are captured, thereby arriving at a more complete "transcriptome" of such single cells, and/or reducing the likelihood of cross-contamination of material from one well to another within a well array. They also serve to expand the use of well-based assays by providing means to spatially locate the well of origin of each transcriptome. This latter improvement enables the linkage of transcriptome data to other measurements or manipulations performed on the cells prior to transcript capture. For example, methods are provided to apply a different condition or a different agent to each well (or in a subset of wells) in a well array, and the effect of such manipulation may be determined. This cellular response can then also be associated with an analysis of the transcriptome of the single cells in these wells. As another example, an end user may interrogate a cell based on expression of one or more markers, for example cell surface markers, and again associate such marker expression with the transcriptional profile of the cell. In yet another example, it allows single cells to be analyzed functionally, for example for cell proliferation or migration activity, and to then associate such functional attributes with particular gene expression patterns. The ability to spatial barcode wells in an array and thus cells in an array allows for combined transcriptomics, proteomics and functional analysis of such cells. They also serve to expand the use of well-based arrays by providing for arrays which are made of dry film photoresist, resulting in arrays that are manufactured in a highly scalable manner, and which can be super-Poisson loaded.

Thus, this disclosure provides in one aspect, a method for producing a library of nucleic acids containing universal primer sites on the 5' and 3' end from input nucleic acids comprising: (a) contacting input nucleic acids with a pool of capture oligonucleotides, each capture oligonucleotide containing a 5' universal primer site and a 3' target binding site (also referred to as a capture site) complementary to a nucleotide sequence in an input nucleic acid, and optionally a barcode, optionally present between the 5' universal primer site and the 3' target binding site, (b) adding a DNA polymerase and thereby extending capture oligonucleotides hybridized to input nucleic acids, and denaturing the first strand nucleic acids from their complementary nucleic acids, to form first strand nucleic acids each comprising the 5' universal primer site and a sequence that is complementary to an input nucleic acid, (c) contacting the first strand nucleic acids with a pool of second strand priming oligonucleotides, each comprising a 5' universal primer site and a 3' target binding site complementary to a nucleotide sequence in the first strand nucleic acid, and (d) adding a DNA polymerase and thereby extending the second strand priming oligonucleotides, to form second strand nucleic acids comprising 5' and 3' universal primer sites that flank nucleotide sequences present in the input nucleic acids.

In some embodiments, the capture oligonucleotides comprise target binding sequences that comprise a poly(dT) sequence. In some embodiments, the capture oligonucleotides comprise target binding sequences that comprise a poly(dT) sequence and/or target binding sequences that comprise a sequence targeting a specific sequence in the input nucleic acids. In some embodiments, the capture oligonucleotides comprise target binding sequences that comprise a sequence targeting a specific sequence in the input nucleic acids.

In some embodiments, the capture oligonucleotides are attached to a surface, optionally a surface of a bead.

In some embodiments, the input nucleic acids are provided as a complex mixture of input nucleic acids. In some embodiments, the input nucleic acids comprise RNA. In some embodiments, the input nucleic acids comprise a mixture of single-stranded DNA (ssDNA) and RNA. In some embodiments, the input nucleic acids are (a) derived from a virus or bacteria, or (b) derived from a eukaryotic cell such as a yeast or an insect cell or a mammalian cell. In some embodiments, the input nucleic acids are derived from an infected cell comprising mammalian or yeast or insect RNA and bacterial or viral DNA. In some embodiments, the input nucleic acids are derived from a single cell. In some embodiments, the input nucleic acids are derived from 2-1000 cells.

In some embodiments, the target binding sequences in the pool of second strand priming oligonucleotides comprise random nucleotide sequences. In some embodiments, the target binding sequences in the pool of second strand priming oligonucleotides comprise semi-random nucleotide sequences. In some embodiments, the target binding sequences in the pool of second strand priming oligonucleotides comprise random sequences and sequences complementary to specific sequences in the first strand nucleic acids. In some embodiments, the target binding sequences in the pool of second strand priming oligonucleotides comprise sequences complementary to sequences in the first strand nucleic acids.

In some embodiments, the pool of second strand priming oligonucleotides further comprises decoy oligonucleotides comprising target binding sequences complementary to sequences in the first strand nucleic acids but lacking the universal primer site to mediate depletion of specific nucleic acids.

In some embodiments, the second strand priming oligonucleotides are attached to a surface, optionally a surface of a bead.

In some embodiments, a crowding reagent is added in step (a), (b), (c) and/or (d). In some embodiments, a crowding reagent is added in step (b). In some embodiments, a crowding reagent is added in step (d).

In some embodiments, the capture oligonucleotides further comprise a random nucleotide sequence for unique molecular identification.

Another aspect of this disclosure provides a method for producing a plurality of identically 5' and 3' labeled cDNA molecules from a single cell, comprising (a) synthesizing, from a single cell RNA library, a first strand cDNA library, wherein first strand cDNA molecules from the library each comprises an identical 5' universal primer site, and optionally an identical barcode; (b) contacting first strand cDNA molecules having a 5' universal primer site with oligonucleotides having a 5' universal primer site upstream of a target binding sequence; and (c) extending the oligonucleotides to produce a plurality of second strand cDNA molecules identically labeled with 5' universal primer sites and 3' universal primer sites.

In some embodiments, the first strand cDNA library is synthesized by hybridization of single RNA molecules to a capture oligonucleotide comprising the 5' universal primer site and a random, semi-random and/or targeted capture sequence. In some embodiments, the first strand cDNA library is synthesized by hybridization of single RNA molecules to a capture oligonucleotide comprising the 5' universal primer site and a poly(dT) capture sequence.

In some embodiments, the capture oligonucleotide is attached to a bead. In some embodiments, a plurality of identical capture oligonucleotides are attached to the bead.

In some embodiments, the capture oligonucleotide comprises a 5' universal primer sequence, a barcode, and a 3' capture sequence.

In some embodiments, the method further comprises obtaining or providing the RNA library from a single cell.

In some embodiments, step (b) further comprises contacting first strand cDNA molecules with decoy oligonucleotides that lack a 5' universal primer site.

Another aspect of this disclosure provides a method for producing a plurality of nucleic acid molecules, comprising (a) synthesizing, from a plurality of parent nucleic acids, first strand nucleic acids each complementary to a parent nucleic acid in the plurality, wherein first strand nucleic acids each comprises an identical 5' universal primer site; (b) contacting first strand nucleic acids having a 5' universal primer site with second strand priming oligonucleotides comprising a 5' universal primer site upstream of a target binding sequence; and (c) extending the second strand priming oligonucleotides to produce a plurality of second strand nucleic acids that are identically labeled with 5' universal primer sites and 3' universal primer sites.

In some embodiments, each of the first strand nucleic acids is synthesized by hybridizing a parent nucleic acid to a capture oligonucleotide having a random, semi-random or targeted sequence. In some embodiments, the capture oligonucleotide is attached to a bead.

In some embodiments, a plurality of identical capture oligonucleotides are attached to the bead.

In some embodiments, the capture oligonucleotide comprises a 5' universal primer sequence, a barcode sequence, and a 3' capture sequence.

In some embodiments, the method comprises obtaining the plurality of parent nucleic acids from a single cell or virus. In some embodiments, the single cell is a pathogen.

In some embodiments, the target binding sequence comprises a random sequence, a semi-random sequence, and/or a non-random/targeted sequence.

In some embodiments, first strand cDNA molecules or the first strand nucleic acids each comprises an identical barcode. In some embodiments, the first strand cDNA molecules or the first strand nucleic acids are attached to a bead.

In some embodiments, the method further comprises adding a crowding reagent in step (a), (b) and/or (c).

In some embodiments, the method further comprises generating first strand cDNA molecules comprising: providing the capture oligonucleotide comprising the 5' universal primer site, a capture sequence, and optionally a barcode sequence therebetween; contacting the capture oligonucleotide with a plurality of RNA molecules from a single cell; allowing the plurality of RNA molecules to anneal to their respective capture sequences; and adding DNA polymerase, thereby extending the capture oligonucleotide to generate the first strand cDNA molecules, wherein the first strand cDNA molecules are complementary to the plurality of RNA molecules.

In some embodiments, the method further comprises generating first strand nucleic acids comprising: providing the capture oligonucleotide comprising the 5' universal primer site, a capture sequence, and optionally a barcode sequence therebetween; contacting the capture oligonucleotide with a plurality of parent nucleic acids from a single cell or virus; allowing the plurality of parent nucleic acids to anneal to the capture sequence; and adding DNA polymerase, thereby extending the capture oligonucleotide to generate the first strand nucleic acids, wherein the first strand nucleic acids is each complementary to a parent nucleic acid.

Another aspect of this disclosure provides a method of increasing the yield of a template switching reaction comprising adding a crowding reagent to a template switching reaction.

Another aspect of this disclosure provides a method of enhancing the sealing of a membrane to a picowell array comprising contacting the picowell array and membrane with a crowding reagent. In some embodiments, the picowell array is used in a Seq-well assay.

Another aspect of this disclosure provides a picowell array comprising a plurality of picowells, each picowell comprising a functionalized surface comprising one or more nucleic acid barcodes.

In some embodiments, each nucleic acid barcode is unique relative to all other nucleic acid barcodes in the array or to a subset of other nucleic acid barcodes in the array.

In some embodiments, one or more nucleic acid barcodes is shared between a plurality of picowells.

In some embodiments, the location of each nucleic acid barcode in the array is known.

In some embodiments, a unique stimulus is applied to each picowell having a unique nucleic acid barcode.

In some embodiments, the functionalized surface is a bottom interior surface of the picowell.

In some embodiments, a bottom interior surface of the picowell array comprises a DNA microarray.

In some embodiments, a plurality of picowells each comprises a spectrally-encoded bead. In some embodiments, a plurality of picowells each comprises a plurality of spectrally-encoded beads. In some embodiments, the spectrally-encoded beads are attached to a functionalized surface of the picowell.

Another aspect of this disclosure provides a picowell array comprising a plurality of picowells, each comprising a functionalized surface that comprises one or more nucleic acid molecules having a unique spatial barcode, each unique spatial barcode being unique to one or a cluster of picowells, optionally wherein the location of each spatial barcode in the picowell array is known.

In some embodiments, the functionalized surface is present in the interior bottom surface of the picowell. In some embodiments, the interior bottom surface of the picowell array comprises a DNA microarray.

In some embodiments, the functionalized surface comprises a spectrally-encoded bead.

Another aspect of this disclosure provides a method for spatially locating transcripts in a picowell array comprising: (a) providing a picowell array wherein: (i) one or more picowells comprise one or more functionalized surfaces that each comprises nucleic acid molecules having a unique spatial barcode; (ii) one or more picowells comprise a unique combination of spatial barcodes; (iii) identity of spatial barcodes located in each picowell is known; and (iv) one or more picowells are loaded with a barcoded transcript capture bead (b) contacting the picowell array with a population of cells, each cell containing one or more transcripts; (c) lysing the cells and capturing RNA from cells on the bead resident in the same well; (d) generating cDNA from the captured transcripts such that the sequence of the bead barcode is incorporated into the cDNA; (e) generating bead barcode:spatial barcode hybrid molecules through primer extension of spatial barcodes bound to transcript capture beads; (f) sequencing the cDNA and bead barcode:spatial barcode hybrid molecules; (g) determining all the spatial barcodes associated with each bead barcode; (h) determining the well of origin for each bead barcode by matching combination of spatial barcodes associated with bead barcode to known picowell with same combination of spatial barcodes; and (i) locating the transcript on the picowell array by matching the bead barcode in the cDNA to the picowell identified as the source of the that bead barcode.

In some embodiments, the functionalized surface comprises the bottom interior surface of the picowell. In some embodiments, the bottom interior surface of the picowell array comprises a DNA microarray.

In some embodiments, the functionalized surface comprises a spectrally-encoded bead.

In some embodiments, the population of cells is delivered to the array as a thin tissue section bound to a glass slide.

Another aspect of this disclosure provides a method for determining a transcriptional response to a set of stimuli using a picowell array comprising: (a) providing a picowell array wherein the majority of picowells each comprise one or more functionalized surfaces comprising (1) nucleic acid molecules having a unique spatial barcode and (2) a unique stimulus; (b) contacting the picowell array with a population of cells containing one or more transcripts; (c) releasing the stimulus from the functionalized surface; (d) culturing the cells to allow for transcriptional response to the released stimulus; (e) loading barcoded transcript capture beads into the majority of wells; (f) lysing the cells and capturing RNA from the cells on the bead resident in the same well as the cell(s); (g) generating cDNA from the captured RNA such that the sequence of the bead barcode is incorporated into the cDNA; (h) generating bead barcode:spatial barcode hybrid molecules through primer extension of spatial barcodes bound to transcript capture beads; (i) sequencing the cDNA and bead barcode:spatial barcode hybrid molecules; (j) determining the combination of spatial barcodes associated with each bead barcode; and (k) determining stimuli exposure of cells that were source of cDNA associated with a given bead barcode by translating combination of spatial barcodes into combination of stimuli present in well.

In some embodiments, the functionalized surface comprises the bottom of the picowell.

In some embodiments, the bottom of the picowell array comprises a DNA microarray.

In some embodiments, the functionalized surface comprises a spectrally-encoded bead.

Another aspect of this disclosure provides a method for spatially locating transcripts on a picowell array comprising: (a) providing a picowell array wherein: (i) each picowell comprises a functionalized surface that comprises one or more nucleic acid molecules having a unique spatial barcode; (ii) each unique spatial barcode is unique to one or a cluster of picowells, and (iii) the location of each unique spatial barcode on the array of picowells is known; (iv) each picowell is loaded with a barcoded transcript capture bead (b) contacting the picowell array with a population of cells containing one or more transcripts; (c) generating cDNA from the transcripts such that the sequence of the bead barcode is incorporated into the cDNA; (d) simultaneously generating of bead barcode:spatial barcode hybrid molecules through primer extension of spatial barcodes bound to transcript capture beads; and (e) locating the transcript on the picowell array by matching the bead barcode in the cDNA to bead barcode:spatial barcode hybrid molecules.

In some embodiments, functionalized surface comprises the bottom of the picowell.

In some embodiments, the bottom of the picowell array comprises a microarray.

In some embodiments, the functionalized surface comprises a spectrally-encoded bead.

In some embodiments, each picowell further comprises a stimulus.

Another aspect of this disclosure provides a method for spatially locating transcripts in a tissue section comprising: (a) providing a picowell array wherein: (i) each picowell comprises a functionalized surface that comprises one or more nucleic acid molecules having a unique spatial barcode; (ii) each unique spatial barcode is unique to one or a cluster of picowells, and (iii) the location of each unique spatial barcode on the array of picowells is known; (iv) each picowell is loaded with a barcoded transcript capture bead (b) contacting the picowell array with a thin tissue section bound to a glass slide; (c) generating cDNA from the transcripts such that the sequence of the bead barcode is incorporated into the cDNA; (d) generating of bead barcode:spatial barcode hybrid molecules through primer extension of spatial barcodes bound to transcript capture beads; and (e) locating the transcript on the picowell array by matching the bead barcode in the cDNA to bead barcode:spatial barcode hybrid molecules.

In some embodiments, functionalized surface comprises the bottom of the picowell.

In some embodiments, the bottom of the picowell array comprises a microarray.

In some embodiments, the functionalized surface comprises a spectral bead.

In some embodiments, each picowell further comprises a stimulus.

Another aspect of this disclosure provides a membrane applicator for applying a membrane to a picowell array comprising: a semi-porous membrane; and a rigid support; wherein the membrane is attached to the rigid support through a reversible chemistry.

In some embodiments, the reversible chemistry is a hydrophilic thin film.

In some embodiments, the hydrophilic thin film is a salt bridge or a hydrophilic polymer.

In some embodiments, the rigid support is glass or acrylic plastic.

In some embodiments, the picowell array is a Seq-well array.

Another aspect of this disclosure provides a method for sealing a semi-porous membrane to an array comprising a plurality of picowells comprising (a) contacting a picowell array with a semi-porous membrane on a rigid support; and (b) applying a heated surface to the rigid support, wherein the semi-porous membrane is sandwiched between the rigid support and the array; thereby sealing the membrane to the picowell array.

In some embodiments, the heated surface is applied to the membrane for less than 10 minutes.

In some embodiments, the heated surface is 35° C.-50° C.

Another aspect of this disclosure provides a device configured to contact one or more picowell arrays with a semi-porous membrane on a rigid support, and apply a heated surface to said rigid support, thereby sealing the semi-porous membrane to the picowell.

In some embodiments, the device comprises a rigid support and a surface capable of being heated to a desired temperature.

Another aspect of this disclosure provides a method for delivering stimuli to cells comprising: (a) providing a picowell array, wherein each picowell comprises one or more beads attached to a stimulus and a nucleic acid comprising a unique stimulus barcode uniquely associated with the stimulus; (b) contacting the picowell array with population of cells containing one or more transcripts; (c) culturing cells with the stimulus; (d) loading each well with a barcoded transcript capture bead; (e) releasing the nucleic acid comprising the unique stimulus barcode from the bead; (f) generating cDNA from the transcripts such that the sequence of the bead barcode is incorporated into the cDNA; (g) generating bead barcode:stimulus barcode hybrid molecules through primer extension of spatial barcodes bound to transcript capture beads; and (h) identifying the stimulus of the cell of origin for each cDNA by matching the bead barcode in the cDNA to bead barcode:stimulus barcode hybrid molecules In some embodiments, the method further comprises releasing the stimulus from the beads.

In some embodiments, the method further comprises sequencing the bead barcode:stimulus barcode hybrid molecules.

Another aspect of this disclosure provides a clamp for affixing a membrane to a picowell array comprising: a three-screw design; wherein the clamp is a square that encompasses an array holder and top piece and contacts the array holder only on the underside, thereby causing upward force on the array.

In some embodiments, the clamp is plastic.

Another aspect of this disclosure provides a method for magnetizing porous resins for use as barcoded beads comprising: (a) contracting the resin, thereby enlarging the pores of the resin; (b) contacting the resin with magnetic nanoparticles; and (c) expanding the resin.

In some embodiments, the resin is contracted by reducing the temperature and is expanded by increasing the temperature. In some embodiments, the resin is contracted and expanded by altering the composition of the solvent.

Another aspect of this disclosure provides a picowell array comprising a plurality of picowells, wherein each picowell (1) is surface-functionalized to enable membrane attachment and single cell transcript capture; and (2) comprises contents of a single cell precipitated and/or fixed to one or more inner walls of the picowell.

Another aspect of this disclosure provides a method to store cells for single cell analysis comprising (a) providing a picowell array wherein the majority of picowells are loaded with a barcoded transcript capture bead, (b) contacting the surface of the array with a single cell suspension, (c) allowing cells to load into picowells though gravity, (d) submerging the array in a fixative, and (e) storing the array for one or more days.

In some embodiments, the picowell array is functionalized to enable attachment of a membrane for transcript capture.

In some embodiments, the array is dried after fixation.

Another aspect of this disclosure provides an array of wells comprising: a first porous membrane having a flux rate of 0.1-100 mL/min/cm$^2$ and/or a pore size of 50 nm-3 microns; and a first bottomless microwell array comprising a dry film of photoresist having a first plurality of through-holes; wherein the first porous membrane contacts the first bottomless microwell array at the bottom surface of the first bottomless microwell array; and wherein each well of the array comprises one of the first plurality of through-holes and a bottom surface comprising the first porous membrane.

Another aspect of this disclosure provides a dry film of photoresist comprising a first array of wells having a largest lateral dimension in the range of 15-100 microns and having a porous bottom having a flux rate of 0.1-100 mL/min/cm$^2$ and/or a pore size of 50 nm-3 microns.

Another aspect of this disclosure provides a microfluidic device comprising a first bottomless microwell array having a largest lateral dimension in the range of 1-500 microns, bonded to (a) a second bottomless microwell array having a largest lateral dimension in the range of 1-500 microns, and (b) a first porous membrane.

Another aspect of this disclosure provides a method of making a free standing photoresist film comprising a plurality of through-holes, comprising: aligning a first dry film of photoresist with a photomask; exposing at least a portion of the first dry film of photoresist to ultraviolet (UV) light through the photomask to form a plurality of first through-holes in the first dry film of photoresist, thereby producing a first free standing photoresist film comprising a plurality of through-holes.

Another aspect of this disclosure provides a method, comprising: flowing a first fluid comprising a plurality of cells and/or a plurality of beads through any of the array of wells, the dry films of photoresist, or the microfluidic devices described herein, thereby forming a cell-loaded and/or a bead-loaded microwell array.

Another aspect of this disclosure provides a method comprising: providing a microfluidic device comprising a first bottomless microwell array having an average well diameter of 15-100 microns and bonded to a first porous membrane having an average pore diameter of 80-1000 nanometers; flowing a first fluid comprising a plurality of beads through the microfluidic device; bonding the first bottomless microwell array bound to the first porous membrane to a second porous membrane having an average pore diameter of 80-1000 nanometers bonded to a second bottomless microwell array having an average well diameter of 1-10 microns; and flowing a second fluid comprising a plurality of cells through the microfluidic device; wherein 80% of the wells of the first bottomless microwell array are occupied by a single bead.

Another aspect of this disclosure provides a method comprising: providing a microfluidic device comprising a first bottomless microwell array having an average well diameter of 1-10 microns and bonded to (a) a second bottomless microwell array having an average well diameter of 15-100 microns, and (b) a porous membrane having an average pore diameter of 80-1000 nanometers; flowing a first fluid comprising a plurality of cells through the microfluidic device; and exposing the microfluidic device to a second fluid comprising beads;

Another aspect of this disclosure provides a kit for processing biological samples that includes a base plate, one or more membranes, and a hybridization plate. The base plate may include a surface with a plurality of receptacles formed therein, and each receptacle is sized and shaped to receive a microwell array. The one or more membranes may be configured to be attached to the surface of the base plate to form an assembly such that the one or more membranes cover the plurality of receptacles. The hybridization plate may be configured to be attached to the assembly with the one or more membranes positioned between the hybridization plate and the base plate. Separate volumes may be formed between an interior surface of the hybridization plate and the one or more membranes where each volume is fluidly coupled with a separate one of the plurality of receptacles.

Another aspect of this disclosure provides a microwell device comprising: (a) a photoresist film comprising a top surface, a bottom surface, and a plurality of through-holes from the top to the bottom surface, wherein each hole has a top opening on the top surface and a bottom opening on the bottom surface, and (b) a porous bottom membrane in contact with the bottom surface of the photoresist film, wherein the bottom membrane has a flux rate of at least 0.1 mL/min/cm2 as measured by the initial flux rate of water at 10 pounds per square inch (psi).

Another aspect of this disclosure provides a substrate-free two-layer laminate comprising: (a) a photoresist film, wherein the photoresist film comprises (i) a top surface, a bottom surface and (ii) a strengthened portion and an unstrengthened portion, wherein upon contacting with a dissolving agent: said unstrengthened portion dissolves to form a plurality of through-holes from the top surface to the bottom surface, and each hole has a top opening on the top surface and a bottom opening on the bottom surface, and at least 25%, 30%, 35%, 40%, 45%, 50%, 60%, or 75% of the top surface, the bottom surface, or both surfaces is covered by the through-holes, and said strengthened portion is substantially resistant to said dissolving agent; and (b) a photomask, wherein a maximum feature distance on the photomask is no more than 2, 1.9, 1.8, 1.7, 1.6, 1.5, 1.4, 1.3, 1.2, 1.1, 1, 0.9, 0.8, 0.7, 0.6, or 0.5 mm, and wherein the photomask is in contact with and covers at least 90%, 91%, 92%, 93%, 94%, 95%, 96%, 97%, 98%, 99% of, or the entire top surface of the photoresist film.

Another aspect of this disclosure provides a method of manufacturing a free-standing photoresist film that comprises a plurality of through-holes comprising, (a) laminating a photoresist film with a photomask, wherein the photomask has a plurality of features and a maximum feature distance of no more than 2, 1.9, 1.8, 1.7, 1.6, 1.5, 1.4, 1.3, 1.2, 1.1, 1, 0.9, 0.8, 0.7, 0.6, or 0.5 mm, and wherein the photomask covers at least 90%, 91%, 92%, 93%, 94%, 95%, 96%, 97%, 98%, 99% of, or the entire photoresist film, (b) exposing the photoresist film to a light source through the photomask for a time sufficient to create a strengthened portion of the photoresist, (c) developing the photoresist film, and (d) separating the photoresist film from the photomask, thereby manufacturing the free-standing photoresist film comprising the plurality of through-holes.

Another aspect of this disclosure provides a method of cellular loading comprising, (a) flowing a fluid sample comprising a plurality of cells through a microarray device, said device comprising, (i) a bottomless microwell array comprising a top surface, a bottom surface, and a plurality of through-holes from the top to the bottom surface, wherein each hole has a top opening on the top surface and a bottom opening on the bottom surface, and (ii) a porous bottom membrane in contact with the bottom surface of the microwell array, wherein the bottom membrane has a flux rate of at least 0.1 mL/min/cm2 as measured by the initial flux rate of water at 10 pounds per square inch (psi), (b) applying a pressure gradient from the top opening to the bottom opening of at least one of the plurality of through-holes, thereby loading a single cell into the at least one through-hole, (c) retaining the cell at the bottom of the at least one through-hole by applying the pressure gradient, (d) inverting the microwell array while the cell is retained, and (e) reversing the inverted microwell array, thereby loading cells in said through-holes in the microarray.

Another aspect of this disclosure provides a method of culturing or storing isolated cells, comprising, (a) flowing a fluid sample comprising a plurality of cells through a microarray device, said device comprising, (i) a bottomless microwell array comprising a top surface, a bottom surface, and a plurality of through-holes from the top to the bottom surface, wherein each hole has a top opening on the top surface and a bottom opening on the bottom surface, and (ii)

a porous bottom membrane in contact with the bottom surface of the microwell array, wherein the bottom membrane has a flux rate of at least 0.1 mL/min/cm2 as measured by the initial flux rate of water at 10 pounds per square inch (psi), (b) loading at least one cell of the plurality of cells into the through-holes by gravity or by application of a pressure gradient, (c) applying a porous top membrane above the top surface of the microwell array, thereby retaining the cells in the through-holes, and (d) submerging the microwell array in a media such that at least a portion of the plurality of through-holes are fluidically connected with the media through the top, the bottom, or both openings.

Another aspect of this disclosure provides a method of analyzing a tissue section comprising: (a) contacting the tissue section with a microarray device, said device comprising, (i) a bottomless microwell array comprising a top surface, a bottom surface, and a plurality of through-holes from the top to the bottom surface, wherein each hole has a top opening on the top surface and a bottom opening on the bottom surface, wherein at least a portion of the plurality of through-holes comprise a barcoded transcript capture bead and a functional surface, and (ii) a porous bottom membrane in contact with the bottom surface of the microwell array, and (b) generating cDNA sequences from the transcripts such that the sequence of the bead barcode is incorporated into the cDNA, thereby analyzing the tissue section.

Another aspect of this disclosure provides a single-cell analyses kit comprising: (a) one or more microarrays each comprising a photoresist film comprising a top surface, a bottom surface, and a plurality of through-holes from the top to the bottom surface, wherein each hole has a top opening on the top surface and a bottom opening on the bottom surface, and (b) at least one porous dry membrane, wherein the membrane has a flux rate of at least 0.1 mL/min/cm2 as measured by the initial flux rate of water at 10 pounds per square inch (psi).

These and other aspects and embodiments of this disclosure will be described in greater detail herein.

BRIEF DESCRIPTION OF DRAWINGS

FIGS. 2A-2C: Improved transcript capture through second strand cDNA tagging. FIG. 2A Standard template-switching method for applying 5′ primer tag. FIG. 2B New second strand cDNA tagging method. FIG. 2C Violin plot of the number of unique transcripts and genes acquired from different cell types using second strand cDNA tagging (purple; horizontal lines) or template switching (gold; vertical lines).

FIG. 3A Scatter plot of the two-dimensional t-SNE reduction of the spectral data. FIG. 3B The percentage of beads that are called correctly using the 5 color spectral barcodes.

FIG. 5A Schematic depicting the generation of double stranded microarray features. FIG. 5B Schematic of the top-down barcoded array. FIG. 5C Schematic of the bottom-up barcoded array. FIG. 5D Image of a picowell array sealed with a labeled DNA microarray.

FIG. 6A Image of material delivered to picowell array using ink jet printing. FIG. 6B Schematic representation of delivery of compounds using particle delivery. FIG. 6C Controlled, nonsynchronous delivery of two compounds (FITC-labeled oligo and AF555-labeled antibody) using desthiobiotin-streptavidin and dithiol-linked biotin:streptavidin linkages.

FIG. 8A Three pieces combined. FIG. 8B Top piece with no internal cavities. FIG. 8C Square clamp with three screw holes. FIG. 8D Bottom of array holder.

FIG. 9A. Heatmap of gene expression signatures of single cells derived from live or methanol fixed cells. FIG. 9B Genes/cell of libraries derived from live or fixed cells. FIG. 9C Transcripts per cell from libraries derived from live or fixed cells. FIG. 9D % Mitochondrial genes per cell from libraries derived from live or fixed cells. FIG. 9E Sequencing reads per cell from libraries derived from live or fixed cells.

FIG. 10A is a cross-sectional schematic diagram of an array 100 of wells, according to certain non-limiting embodiments. FIG. 10B is a cross-sectional schematic diagram of an array 1000 of wells, according to certain non-limiting embodiments. FIG. 10C is a cross-sectional schematic diagram of an array 800 of wells, according to certain non-limiting embodiments. FIG. 10D is a cross-sectional schematic diagram of a layered device 200, according to certain non-limiting embodiments. FIG. 10E is a cross-sectional schematic diagram of a layered device 300 (e.g., a microfluidic device), according to certain non-limiting embodiments.

FIG. 11A is a dry film of photoresist having through-holes of 50 micron diameter. FIG. 11B is a dry film of photoresist having through-holes of 5 micron diameter.

FIG. 12A is a cross-sectional schematic diagram of a layered device 400 (e.g., a microfluidic device), according to certain non-limiting embodiments. FIG. 12B is a cross-sectional schematic diagram of a layered device 500 (e.g., a microfluidic device), according to certain non-limiting embodiments. FIG. 12C is a cross-sectional schematic diagram of a layered device 600 (e.g., a microfluidic device), according to certain non-limiting embodiments. FIG. 12D is a cross-sectional schematic diagram of a layered device 700 (e.g., a microfluidic device), according to certain non-limiting embodiments.

FIG. 13A is a cell-loaded array fabricated from dry film photoresist. FIG. 13B is a cell-loaded array fabricated from dry film photoresist and stained with mitotracker red.

FIG. 20A is a schematic perspective view of one embodiment of a hybridization chamber prior to bonding with a microwell array. FIG. 20B is a schematic perspective view of the embodiment of a hybridization chamber of FIG. 20A bonded to a microwell array during sample collection.

DETAILED DESCRIPTION OF INVENTION

Figure 1:
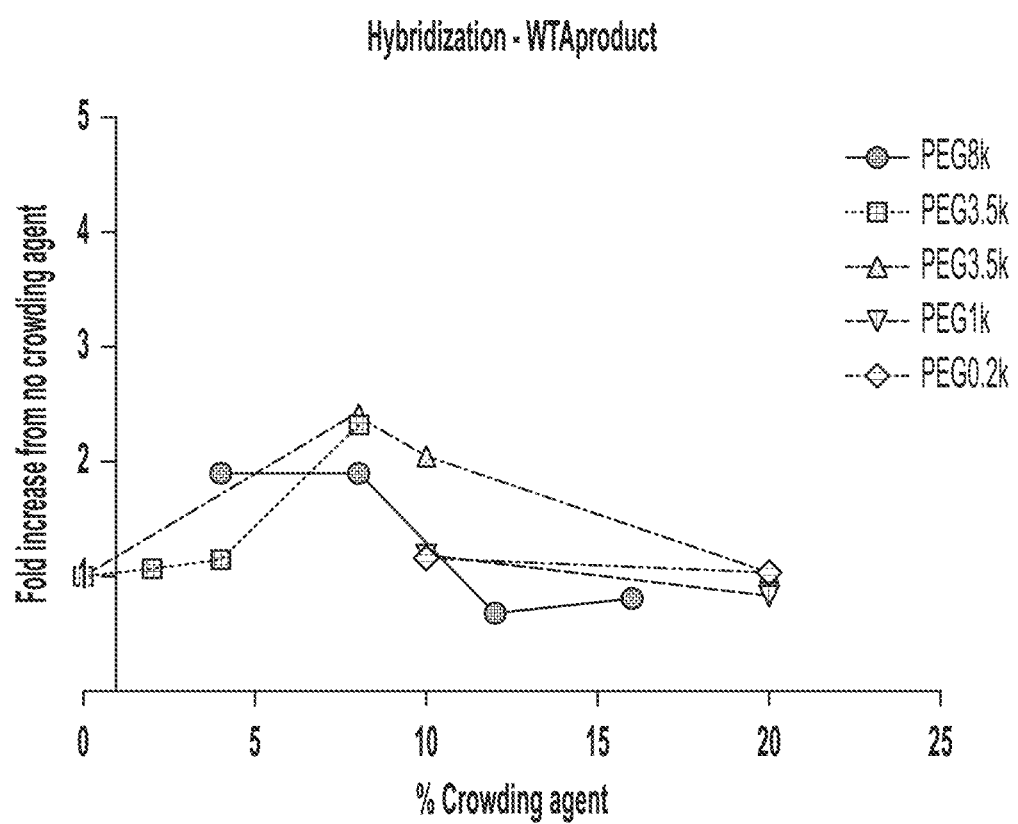
FIG. 1: Crowding reagent increases whole transcriptome amplification product yields. Different concentrations of various poly(ethylene glycol) sizes were included in both the hybridization buffer and wash buffer. Whole transcriptome amplification (WTA) product yields from equivalent numbers of barcoded beads was quantitated using an AATI fragment analyzer. WTA comprises amplification of a whole transcriptome by first synthesizing cDNA from RNA and then amplifying the cDNA. The AATI fragment analyzer provides detailed information on nucleic acid concentration and size distribution.

This disclosure describes improvements to both the hardware and applications relating to well-based or other contained volume systems including picowell-based systems and droplet-based systems.

Picowells and picowell arrays facilitate massively parallel analysis of large numbers of single cells or other nucleic acid sources such as single viruses, single nuclei, etc. However, the exceptionally small volume of these wells and the high-density of their corresponding arrays precludes the use of standard fluid handling techniques for delivering to and/or retrieving from such wells reagents, nucleic acid sources such as cells, and/or cellular contents such as mRNA transcripts. It will be understood that, in some embodiments, the arrays described herein, e.g., arrays comprising dry film photoresist, are not referred to as picowell arrays, which refer to the volume contained in each well, but rather are characterized by the diameter and depth of the wells.

The disclosure provides, in part, improvements relating to arrays, e.g., picowells and high-density picowell arrays. These improvements include but are not limited to improved nucleic acid capture from single cells, improved portability and ease of use, increased scalability of any given assay, linkage of transcript or transcriptome information to other measurements or interventions made in the well, and improved arrays made of dry film photoresist, which provide for increased scalability in manufacture and super-Poisson loading, as is described in further detail below. It will be understood that various of these improvements may also be applied to non-well based systems such as droplet-based systems.

As used herein, a picowell refers to a well having a volume in the picoliter range, including volumes ranging from less than 1 picoliter to about 10,000 picoliters including volumes ranging from about 0.01 picoliter to about 1000 picoliters or about 0.1 picoliter to less than 1000 picoliters or about 0.01 picoliter to about 500 picoliters. The range may be about 1 picoliter to about 1000 picoliters, or about 3 picoliters to about 1000 picoliters, or about 3 picoliters to about 500 picoliters, or about 3 picoliters to about 125 picoliters or about 0.05 picoliters to about 1000 picoliters, or about 0.1 picoliters to about 500 picoliters, or about 0.1 picoliters to about 125 picoliters. These wells typically have dimensions (e.g., x and y or diameter, and height dimensions in the micron ranges. For example, a well may have dimensions of about 45 microns (x) by about 45 microns (y) by about 60 microns (h) and have a rectangular volume, or they may have dimensions of about 50 microns (x) by about 50 microns (y) by about 50 (h) microns and have a cube volume. The well may have cross-sectional area (from a top-down perspective) that is square or circular or oval, although not limited to any of these. Thus, to the extent the term "microwell" or "well" is used in this disclosure, it is to be understood that such term refers to wells having a picoliter or sub-picoliter (e.g., from 1 femtoliter to 10,000 picoliter volume.

A picowell array may comprise about $10^3$ to about $10^7$ wells, about $3 \times 10^3$ to about $10^7$ wells, about $5 \times 10^3$ to about $10^7$ wells, about $10^4$ to about $10^7$ wells, about $10^4$ or about $5 \times 10^4$ or about $8 \times 10^4$ through to about $10^5$ or about $5 \times 10^5$ or about $1 \times 10^6$ or about $5 \times 10^6$ or about $1 \times 10^7$ wells, and accordingly are referred to as "high-density" arrays.

In some embodiments, the wells and well arrays are functionalized to perform Seq-well. Seq-well arrays are described in published PCT Application No. PCT/US17/13791, the contents of which are incorporated herein in their entirety. In Seq-well, an array of >80,000 picoliter wells are used to isolate single cells together with a barcoded transcript-capture bead. A semi-porous membrane is used to seal the wells, in an effort to minimize escape of and thus cross-contamination of macromolecules, such as mRNA, while allowing passage of small molecules and lysis buffers. This enables cell lysis within the sealed wells and consequently the generation of RNA-seq libraries. This is accomplished by first capturing mRNA molecules released by the lysed cells on the barcoded bead that is resident in the well. After capture, the unique barcode of the bead (and therefore, of the well) is incorporated into first strand cDNA synthesized using reverse transcription from (and thus complementary to) the captured mRNA transcripts, in the process of creating a cDNA library from each single cell. The bead barcode therefore identically marks (or labels) all the captured transcripts from the same single cell. The barcoded cDNA libraries may then be combined, with each cDNA marked as to its single cell origin, and may undergo whole transcriptome amplification (WTA), and then sequencing. In some embodiments, single cell transcriptomes are recovered in silico by aggregating all the transcripts with the same bead barcode.

The library may comprise transcripts from a plurality of cells, including for example about 100, 1,000, 10,000, 20,000. 30,000, 40,000, 50,000, 60,000, 70,000, 80,000, 90,000, 100,000, 200,000, 300,000, 400,000, 500,000, 600, 000, 700,000, 800,000, 900,000 or 1,000,000 or more cells. Accordingly, the well arrays in some instances are large enough to accommodate these same numbers of cells in order to perform parallel analysis of these cells.

It will be understood by those in the art in view of this disclosure that various methodologies may be employed to increase the proportion of wells in an array that are occupied by a single cell and to concurrently decrease the proportion of wells in an array that are occupied by two or more cells. One way to achieve this is to dilute the cell suspension (and concurrently reduce the absolute cell number applied to an array) such that the vast majority of wells have either no cells or a single cell. In some instances, about 5-15% of wells are occupied by single cells, and 1-2% or fewer of the wells are occupied by two or more cells. The remainder of the wells are not occupied by any cells. It will be appreciated that the same approach can be adopted for other nucleic acid sources that may be analyzed using the methods and products of this disclosure including without limitation viruses, nuclei, exosomes, platelets, etc.

The various improvements provided by this disclosure are discussed in greater detail below.

Methods for Increasing Nucleic Acid (e.g., Transcript) Recovery

Some aspects of this disclosure relate to improving the quality of single cell RNA-seq libraries by increasing the number of unique transcripts captured from single cells. Higher cell transcript yields provide increased statistical power for identifying unique cell populations within a sample. Provided herein are methods to improve transcript capture yields from, for example, single cells or small groups of cells, in single wells or in droplets. These methods involve improved second strand cDNA tagging methodologies to increase transcript capture efficiency as wells as the use of crowding reagents. Among other things, these are associated with improved performance of well-based assays such as the Seq-well assay as well as droplet-based systems. This disclosure contemplates that either or both methods may be used in sequence or concurrently.

Second Strand Nucleic Acid (e.g., cDNA) Tagging/Labeling to Increase Nucleic Acid (e.g., Transcript) Capture Efficiency Provided herein are improved methods for efficiently tagging (e.g., labeling with or conjugating to a nucleic acid) nucleic acids, such as but not limited to second strand cDNA molecules, with universal primer sequences. These methods may be used to identically 5' and 3' label nucleic acids that derive from a single source such as a single cell, single nucleus, single virus, etc. To identically 5' and 3' label nucleic acids means to incorporate an identical nucleotide sequence on the 5' ends of a plurality of nucleic acids from the single source, and to incorporate an identical nucleotide sequence on the 3' ends of a plurality of nucleic acids from the single source. The nucleotide sequences at the 5' and 3' ends however need not be and in most instances are not the same. Nucleic acids that are identically 5' and 3' labeled share the same 5' nucleotide sequence and the same 3' nucleotide sequence, even though the 5' and 3' nucleotide sequences may not be the same (and typically are not the same). The benefit of identically 5' and 3' labeling nucleic acids is that such nucleic acids may be amplified and/or sequenced with relatively similar efficiency.

The 5' and 3' nucleotides sequences that are shared between nucleic acids will minimally comprise 5' and 3' universal primer sequences (or universal primer sites, as those terms are used interchangeably herein). Common or shared 5' and 3' UPS in a plurality of nucleic acids facilitate the relatively non-preferential amplification and/or sequencing of such nucleic acids, including when such nucleic acids are pooled together. Such nucleic acids may be from a single source, such as a single cell, or they may be from a plurality of different sources, such as a plurality of cells.

The 5' and/or 3' nucleotides sequences that are shared between nucleic acids may comprise a barcode. Barcodes refer to unique sequences that are used to label and identify nucleic acids from a particular source, and to distinguish such nucleic acids from other nucleic acids from one or more other sources. Barcodes, in this context, may be referred to as nucleic acid barcodes because of their nucleic acid nature. In some instances provided herein, barcodes are used label, identify and distinguish nucleic acids derived from a single cell from those derived from one or more other cells. Such barcodes may be referred to cell-specific barcodes. Barcodes may also be used to label and identify and thus distinguish nucleic acids from a population of cells that have been similarly manipulated. In some instances, two or more barcodes may be used, wherein one barcode identifies the cell source and another barcode identifies the manipulation. Barcodes may be incorporated into the 5' end and/or the 3' end of a nucleic acid. For example, a barcode may be incorporated during a first strand cDNA synthesis reaction by including the barcode in the primer sequence from which the cDNA is synthesized. The barcode can then be incorporated in second strand cDNA and further progeny. The barcode may be of a known sequence. The barcode may be random.

The 5' and/or 3' nucleotide sequences that are shared between nucleic acids may comprise a capture site or domain (or target binding site, as the terms are used interchangeably). The capture domain comprises a nucleotide sequence that is complementary to a sequence in the target nucleic acid (and thus may be referred to as a target binding sequence) or a complementary sequence thereof. This domain acts to hybridize (and thus capture) the target nucleic acid, following which first strand and second strand nucleic acids may be generated. The capture domain may have random, semi-random or specific (or targeted) sequence. An example of a specific (or targeted) sequence is a poly(dT) sequence which hybridizes with the poly(dA) sequence of mRNA transcripts. Other examples of specific (or targeted) sequences are sequences that are complementary to known conserved nucleotide sequences in transcripts, particular transcripts, or certain nucleic acid classes. It will be understood that, depending on whether the capture domain is present in the first or second strand nucleic acid, the capture sequence will be either complementary or identical to the corresponding sequence in the target nucleic acid.

FIG. 2B illustrates one embodiment for 5' and 3' labeling of target nucleic acids in the context of mRNA capture and first and second strand cDNA synthesis. Initially the mRNA is captured by hybridization to a capture oligonucleotide that is bound to a bead. The capture oligonucleotide minimally comprises a UPS and a capture domain and may optionally comprise a barcode sequence. As an example, the capture oligonucleotide sequence may be from the bead 5'-UPS-barcode-capture domain-3'. Since the target nucleic acid is an mRNA transcript, then the capture domain may have a poly(dT) sequence in order to hybridize to the poly(dA) tail of the mRNA. The target mRNA transcript binds to the capture oligonucleotide via the capture domain and then through a process of reverse transcription a first strand cDNA is synthesized from the capture oligonucleotide. In this way, the first strand cDNA comprises the 5' UPS, the barcode, the capture domain, and the complementary sequence of the mRNA target.

Second strand cDNA synthesis is carried out by then hybridizing the first strand cDNA to one or more other oligonucleotides each having a 5' UPS and a capture domain. These oligonucleotides may be referred to as "second strand priming oligonucleotides". In FIG. 2B, they are referred to as UPS-tagged randomers. The capture domain may comprise random, semi-random or specific (targeted) sequence. An example of this oligonucleotide is shown in FIG. 2B as having the sequence NNNGGNNNB. The GG motif prevents self-hybridization as well as binding to the poly(dT)/universal primer. The oligonucleotide shown in the Figure is referred to as a randomer, intending that its capture sequence is random and that it is designed to bind randomly to mRNA transcripts. Upon addition of DNA polymerase, the oligonucleotide is extended until it either reaches the next adjacent oligonucleotide or the end of the first strand cDNA. It is those second strand nucleic acids that are located in closest proximity to the end of the first strand cDNA which are of greatest interest and they will incorporate both 5' and 3' UPS, and optionally 5 and/or 3' barcodes which may be random sequence barcodes, and/or optionally 5' and/or 3' capture sequences.

It is further to be understood that once the target nucleic acid (e.g., mRNA transcript) is captured on the bead, the remaining steps in the procedure may be performed in the well (or droplet) or outside of the well. In particular, the second strand synthesis step is typically performed in solution following the pooling of contents from a plurality of wells or a plurality of droplets. It is possible to do this step outside of a confined volume such as the well or droplet because the cell-specific transcripts are already covalently attached to the bead, via the covalently attached first strand nucleic acids (e.g., first strand cDNA). Second strand synthesis may be performed in a single reaction volume using beads from a plurality of wells or droplets, including for example all wells from a picowell array.

If the method is used to capture mRNA transcripts from a plurality of cells, then a subset of the second strand cDNA that are generated will have the same 5' UPS and the same 3' UPS. Therefore these "identically" labeled single strand nucleic acids may be amplified using the same primers and/or sequenced using the same primers.

Thus, in some instances, the methods tag (or label) second strand cDNA with universal primer sequences to enable whole transcriptome amplification (WTA). Due to the limited amount of available RNA, cDNA libraries generated from single or small numbers of cells must be PCR amplified prior to sequencing. PCR amplification requires known primer binding sites flanking the sequences to be amplified. In the case of WTA, universal primer sites are typically added to the both sides of the cDNA. As discussed above, a universal primer site is easily added to the 5' end of the first strand cDNA by hybridizing the target RNA to an oligonucleotide containing a universal primer sequence 5' to a capture sequence, e.g. poly(dT) sequence, and then performing reverse transcription, yielding a first strand cDNA with a universal primer sequence on its 5' end.

Adding a universal primer sequence to the other end of the cDNA however heretofore has been a challenge. Herein we provide methodologies for efficiently adding this second universal primer site.

Current state of the art utilizes either a template switching reverse transcription reaction, poly(dA) tailing of the first cDNA strand, or ligation to double stranded cDNA to add a second universal site, with template switching (FIG. 2A) being the most common procedure. Template switching leverages dC tailing activity of some reverse transcriptases to generate a universal poly(dC) site on the end of the first strand cDNA during the reverse transcription reaction, which is bound by the template switching oligonucleotide which contains the universal primer site 5' to a poly(dG) tract. The reverse transcriptase then extends from the poly (dC) tail on the cDNA, adding the universal primer site to the 3' end of the first strand cDNA. Though simple, template switching is inefficient and requires reverse transcription of the entire RNA, favoring shorter RNA molecules.

Instead of adding the second universal primer site to the 3' end of first strand cDNA, we devised a method to add the second primer site during second strand synthesis. This can be achieved at least as described above and as illustrated in FIG. 2B. Starting with the first strand cDNA containing a universal prime site on its 5' end, the second strand is synthesized by hybridizing and extending an oligonucleotide that contains the universal primer sequence 5' to a target binding (or capture) sequence. The target binding sequence may be a random primer sequence or it may be a targeted primer sequence. The primer is extended using a DNA polymerase, preferably one lacking both 5'-3' and 3'-5' exonuclease activity such as Klenow exo-, Bsu large fragment or Bst large fragment. FIG. 2C shows comparisons of transcript yield per cell for a variety of cell types using the standard template switching approach and the second strand synthesis approach of this disclosure. As shown, the second strand synthesis approach increases the transcript yield per cell 5-10-fold (FIG. 2C) compared to a template switching reaction. For example, as is shown in FIG. 2C, both the number of UMIs (e.g., the number of individual transcripts) and the number of genes identified was substantially increased relative to a template switching reaction.

An additional benefit of having both primer sites on the second strand nucleic acid, e.g., DNA, or cDNA when first strand synthesis is primed by bead-bound oligonucleotides as in the case of SeqWell, is the second strand is not covalently linked to the barcoded bead surface, enabling easier separation of the tagged second strand nucleic acid e.g., DNA or cDNA, from the bead prior to subsequent manipulations such as but not limited to amplification (e.g., PCR). Separation of the non-covalently attached second strand from the bead can be accomplished by any means including but not limited to simple base-mediated DNA denaturation. This enables the use of a single PCR reaction for WTA amplification and retention of the barcoded bead for sample banking.

In prior art methods, the WTA reaction had to be split across ~40 reactions/array to ensure efficient amplification of the second strand nucleic acids, e.g., cDNA, due to inefficient priming on the bead surface and "poisoning" of the PCR reaction by beads if present at too high a concentration. Additionally, after PCR cycling, the beads were typically discarded. The WTA amplification is half the price of the library preparation so second strand tagging should significantly decrease the cost of library preparation as well.

As discussed above, the second strand DNA synthesis methods of this disclosure can also be used to generate a directed library. A pool of second strand-priming oligonucleotides with target binding sequences (capture sequences) specific for a desired set of first strand cDNA molecules can be used to generate sequencing libraries containing transcripts of interest. Alternatively, oligonucleotides containing target binding sequences (capture sequences) specific for a set of cDNA molecules but lacking the universal primer sequence can be used to deplete the targeted cDNA molecules from the library when used in conjunction with probes containing both the universal primer sequence and target binding sequences (capture sequences). Finally, a mixture of two oligonucleotides containing the same target binding sequence (capture sequence) and either lacking or comprising the universal primer sequence can be used to quantitatively normalize the concentration of highly expressed cDNA molecules based on the ratio of the two oligonucleotides, e.g. only 1 in 4 copies of a given cDNA will be tagged with the universal primer sequence and amplified if the ratio of oligonucleotide comprising the universal primer site to the oligonucleotide lacking the site is 1:3.

As used herein, a "universal primer site" is an exogenous primer binding site introduced into the nucleic acid molecule for the purpose of primer binding. Examples of universal primer sites include p5 and nextera. It is to be understood that the terms "universal primer site" and "universal primer sequence" are used interchangeably.

In some embodiments, the 5' universal primer site is 10, 11, 12, 13, 14, 15, 16, 17, 18, 19, 20, 21, 22, 23, 24, 25, 26, 27, 28, 29, or 30 nucleotides long, e.g., 10-30, or 15-25 nucleotides long. In some embodiments, the 3' universal primer site is 10, 11, 12, 13, 14, 15, 16, 17, 18, 19, 20, 21, 22, 23, 24, 25, 26, 27, 28, 29, or 30 nucleotides long, e.g., 10-30, or 15-25 nucleotides long. The universal primer sites at the 5' and 3' ends may be the same or they may be different.

In some embodiments, the target binding site (or target binding sequence or capture site, sequence or domain, as the terms are used interchangeably) is a randomer, e.g., is not complementary to sequences in specific nucleic acids such as cDNA molecules (see, e.g., UPS-tagged randomer in FIG. 2B). In some embodiments, the sequence of the target binding site is semi-random. In some embodiments, the sequence of the target binding site is complementary to a sequence in a specific nucleic acid, e.g., a cDNA molecule, enabling targeted tagging of the desired nucleic acid, e.g., cDNA molecule. In some embodiments, the target binding sequence is 5, 6, 7, 8, 9, 10, 11, 12, 13, 14, or 15 nucleotides long, e.g., 5-15, or 7-12 nucleotides long. In some embodiments, a plurality of oligonucleotides with different target binding sites are used to make targeted libraries of desired cDNA molecules.

In some embodiments, contacting the first strand nucleic acid, e.g., cDNA, having a 5' universal primer site with an oligonucleotide comprising a universal primer site upstream of a target binding sequence comprises annealing (or hybridizing) the first strand nucleic acid, e.g., cDNA, having a 5' universal primer site with an oligonucleotide comprising the universal primer site upstream of a target binding sequence at the target binding site. (see., e.g., FIG. 2B) In some embodiments, the target binding site is annealed to the first strand nucleic acid, e.g., cDNA, having a 5' universal primer site at 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C.

In some embodiments, the first strand nucleic acid, e.g., cDNA, having a 5' universal primer site is attached to a bead 5' to the universal primer site. Conventional covalent linkage methodology may be used to attach the capture oligonucleotide and thus ultimately the first strand nucleic acid to the bead. Any covalent or non-covalent attachment means of sufficient strength may be used including for example affinity binding pairs such as but not limited to biotin-streptavidin. In some embodiments, the bead is a transcript capture bead.

As used herein, a "capture bead" comprises a bead having a capture oligonucleotide attached to its surface, which in turn comprises a capture domain, site or sequence for annealing to target nucleic acids such as target transcripts. If the target nucleic acids are transcripts then the bead may be referred to as a "transcript-capture bead". In some embodiments, the transcript capture bead has a poly(dT) capture sequence for annealing to the poly(dA) tail of mRNA transcripts. As discussed above, in some embodiments, the capture oligonucleotide further comprises a barcode. The barcode can be used for labeling all captured nucleic acids from a single cell, including all captured transcripts of a single cell. This may be accomplished when the transcript capture bead and the single cell are placed in the same well and the cell is lysed. The barcode may be used to label nucleic acids from a single cell (or a single well) or it may be used to label nucleic acids from a plurality of cells (or a plurality of wells). In this latter embodiment, the barcode may be used to represent a particular manipulation carried out on the cells (or wells).

The size of the capture beads will typically be dictated by the size of the well or droplet in which is used. In some embodiments, the size of the bead will be chosen such that only one bead can occupy a well or droplet at a single time. Alternatively, the dimensions of the well or droplet may be chosen such that only one bead can occupy a well or droplet at a single time. In some embodiments, the capture beads are 1 μm, 5 μm, 10 μm, 15 μm, 25 μm, 30 μm, 35 μm, 40 μm, 45 μm, 50 μm, 55 μm, 60 μm, 65 μm, 70 μm, 75 μm, 80 μm, 90 μm, 100 μm, 110 μm, 120 μm, 150 μm, or 200 μm in diameter. In some embodiments, the transcript capture beads are from 10 μm-50 μm in diameter. In some embodiments, the beads are about 35 microns in diameter.

As used herein, a "barcode" refers to a nucleotide sequence that is used as an identifier. It may be used, in some instances, to identify a condition (e.g., a condition to which a well and thus a cell is subjected), a physical location on an array, or a single nucleic acid source such as a single cell. In some embodiments, a barcode identifies a nucleic acid or a set of nucleic acids (e.g., a transcript or a set of transcripts) as being from the same cell. In some embodiments, a barcode identifies a nucleic acid or a set of nucleic acids (e.g., a transcript or a set of transcripts) as being associated with a particular spatial location or with a particular treatment or manipulation, optionally at that location. For example, in some embodiments, a barcode identifies a nucleic acid or a set of nucleic acids (e.g., a transcript or set of transcripts) as being associated with exposure to a particular stimulus. In some embodiments, a barcode is 3, 4, 5, 6, 7, 8, 9, 10, 11, 12, 13, 14, 15, 16, 17, 18, 19, 20, 21, 22, 23 24, 25, 26, 27, 28, 29, or 30 nucleotides, e.g., is from 10 to 30 nucleotides long.

In some embodiments, the capture sequence comprises about 5, 6, 7, 8, 9, 10, 11, 12, 13, 14, 15, 16, 17, 18, 19, 20, 25 or 30 nucleotides.

In some embodiments, the capture oligonucleotide comprises about 10, 20, 30, 40, or 50 nucleotides.

In some embodiments, the RNA or single stranded DNA anneals to its capture sequence at 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., or 65° C. The conditions for annealing (hybridizing) the capture oligonucleotide to the target nucleic acid and/or the second strand priming oligonucleotides to the first strand nucleic acids may depend upon the particular nucleotide sequences but can nevertheless be determined by one of ordinary skill. The methods of this disclosure provide that target nucleic acids as well as first strand nucleic acids be relatively equally hybridized to their respective complementary oligonucleotides, whether such oligonucleotides are the capture oligonucleotides attached to beads or the second strand priming oligonucleotides.

It is to be understood that the foregoing methods may be used to capture RNA transcripts from a single cell, and thus are applicable to technologies such as but not limited to Seq-well, Drop-Seq, InDrop, and 10× Genomics. However, these methods have broader applicability and can be used to capture other nucleic acids from nucleic acid sources provided that such nucleic acids can be hybridized to the capture oligonucleotide and that they can be used to generate first strand nucleic acids from which second strand nucleic acids are formed.

Nucleic acid sources are sources comprising nucleic acids of interest. These include cells, viruses, nuclei, exosomes, bodily fluids and precipitates thereof, and the like. Virtually any source of nucleic acid may be used in the methods provided herein.

"Oligonucleotides", in the context of the invention, refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). Oligonucleotides include DNA such as D-form DNA and L-form DNA and RNA, as well as various modifications thereof. Modifications include base modifications, sugar modifications, and backbone modifications. Non-limiting examples of these are provided below.

Non-limiting examples of DNA variants that may be used in the invention are L-DNA (the backbone enantiomer of DNA, known in the literature), peptide nucleic acids (PNA) bisPNA clamp, a pseudocomplementary PNA, a locked nucleic acid (LNA), or co-nucleic acids of the above such as DNA-LNA co-nucleic acids. It is to be understood that the oligonucleotides used in products and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The oligonucleotide modification may render the oligonucleotide more stable and/or less susceptible to degradation under certain conditions. For example, in some instances, the oligonucleotides are nuclease-resistant.

The oligonucleotides may have a homogenous backbone (e.g., entirely phosphodiester or entirely phosphorothioate) or a heterogeneous (or chimeric) backbone. Phosphorothioate backbone modifications render an oligonucleotide less susceptible to nucleases and thus more stable (as compared to a native phosphodiester backbone nucleic acid) under certain conditions. Other linkages that may provide more stability to an oligonucleotide include without limitation phosphorodithioate linkages, methylphosphonate linkages, methylphosphorothioate linkages, boranophosphonate linkages, peptide linkages, alkyl linkages, dephospho type linkages, and the like. Thus, in some instances, the oligonucleotides have non-naturally occurring backbones.

Oligonucleotides may be synthesized in vitro. Methods for synthesizing nucleic acids, including automated nucleic acid synthesis, are also known in the art. Oligonucleotides having modified backbones, such as backbones comprising phosphorothioate linkages, and including those comprising chimeric modified backbones may be synthesized using automated techniques employing either phosphoramidate or H phosphonate chemistries. (F. E. Eckstein, "Oligonucleotides and Analogues—A Practical Approach" IRL Press, Oxford, UK, 1991, and M. D. Matteucci and M. H. Caruthers, Tetrahedron Lett. 21, 719 (1980)) Aryl and alkyl phosphonate linkages can be made, e.g., as described in U.S. Pat. No. 4,469,863; and alkylphosphotriester linkages (in which the charged oxygen moiety is alkylated), e.g., as described in U.S. Pat. No. 5,023,243 and European Patent No. 092,574, can be prepared by automated solid phase synthesis using commercially available reagents. Methods for making other DNA backbone modifications and substitutions have been described. Uhlmann E et al. (1990) Chem Rev 90:544; Goodchild J (1990) Bioconjugate Chem 1:165; Crooke S T et al. (1996) Annu Rev Pharmacol Toxicol 36:107-129; and Hunziker J et al. (1995) Mod Synth Methods 7:331-417.

The oligonucleotides may additionally or alternatively comprise modifications in their sugars. For example, a β-ribose unit or a β-D-2'-deoxyribose unit can be replaced by a modified sugar unit, wherein the modified sugar unit is for example selected from β D-ribose, α-D-2'-deoxyribose, L-2'-deoxyribose, 2'-F-2'-deoxyribose, arabinose, 2'-F-arabinose, 2'-O—(C1-C6)alkyl-ribose, preferably 2'-O—(C1-C6)alkyl-ribose is 2'-O-methylribose, 2'-O—(C2 C6)alkenyl-ribose, 2'-[O—(C1-C6)alkyl-O—(C1-C6)alkyl]-ribose, 2'-NH2-2'-deoxyribose, β D xylo-furanose, a arabinofuranose, 2,4 dideoxy-β-D-erythro-hexo-pyranose, and carbocyclic (described, for example, in Froehler J (1992) Am Chem Soc 114:8320) and/or open-chain sugar analogs (described, for example, in Vandendriessche et al. (1993) Tetrahedron 49:7223) and/or bicyclosugar analogs (described, for example, in Tarkov M et al. (1993) Helv Chim Acta 76:481).

The oligonucleotides may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7 deazaguanine, 7 deaza 7 substituted guanine (such as 7 deaza 7 (C2 C6)alkynylguanine), 7 deaza 8 substituted guanine, hypoxanthine, N2-substituted guanines (e.g. N2-methyl-guanine), 5-amino-3-methyl-3H,6H-thiazolo[4,5-d]pyrimidine-2,7-dione, 2,6 diaminopurine, 2 aminopurine, purine, indole, adenine, substituted adenines (e.g. N6-methyl-adenine, 8-oxo-adenine) 8 substituted guanine (e.g. 8 hydroxyguanine and 8 bromoguanine), and 6 thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichlorobenzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-β-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

"Probes" and "primers", as described herein, comprise oligonucleotides. They can be nucleic acids in whole or in part. They may comprise naturally occurring nucleotides and/or non-naturally occurring nucleotides. They may be or may comprise DNA, RNA, DNA analogs, RNA analogs, PNA, LNA and combinations thereof, provided it is able to hybridize in a sequence-specific manner to oligonucleotides and/or to be conjugated in some instances to a label.

In some embodiments, the probes or primers comprise adenine, thymine, guanine, and cytosine. In some embodiments, the probes or primers comprise uracil in place of thymine.

The probe or primer may form at least a Watson-Crick bond with the target. In other instances, the probe or primer such as the probe may form a Hoogsteen bond with the target, thereby forming a triplex. A probe or primer that binds by Hoogsteen binding enters the major groove of a nucleic acid and hybridizes with the bases located there. In some embodiments, the probes or primers can form both Watson-Crick and Hoogsteen bonds with the target. BisPNA probes, for instance, are capable of both Watson-Crick and Hoogsteen binding to a nucleic acid.

The probe or primer can be any length including but not limited to 8-100 nucleotides, 8-75 nucleotides, 8-50 nucleotides, 8-30 nucleotides, 18-30 nucleotides, and every integer therebetween as if explicitly recited herein.

The probes or primers are preferably single stranded, but they are not so limited. For example, when the probe or primer is a bisPNA it can adopt a secondary structure with the target resulting in a triple helix conformation, with one region of the bisPNA forming Hoogsteen bonds with the backbone of the identifier sequence and another region of the bisPNA forming Watson-Crick bonds with the bases of the target.

The binding of the probe or primer to the target via hybridization can be manipulated based on the hybridization conditions. For example, salt concentration and temperature can be modulated. Those of ordinary skill in the art will be able to determine optimum conditions for a desired specificity. In some embodiments, the hybridization conditions are stringent so that only completely complementary probes or primers will bind to the target. In other embodiments, less than stringent conditions are used.

Sequence-dependent binding when used in the context of a nucleic acid hybridization means recognition and binding to a particular linear arrangement of nucleotides in the nucleic acid. In the case of probes and primers, the linear arrangement includes contiguous nucleotides that each binds to a corresponding complementary nucleotide in the probes and primers.

The probes and primers described herein hybridize to their target nucleic acids, typically under stringent conditions. The term "stringent conditions" as used herein refers to parameters with which the art is familiar. Nucleic acid hybridization parameters may be found in references which compile such methods, e.g. Molecular Cloning: A Laboratory Manual, J. Sambrook, et al., eds., Fourth Edition, Cold Spring Harbor Laboratory Press, Cold Spring Harbor, N.Y., 2012, or Current Protocols in Molecular Biology, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH2PO4 (pH7), 0.5% SDS, 2 mM EDTA). SSC is 0.15M sodium chloride/0.015M sodium citrate, pH 7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit specific and selective hybridization of probes and/or primers to the nucleic acids of the invention (e.g., by using lower stringency conditions).

Crowding Reagents to Increase Nucleic Acid (e.g., Transcript) Capture Efficiency Another approach for increasing nucleic acid capture efficiency (i.e., increasing the number of nucleic acids captures per single nucleic acid source such as for example per cell) involves the use of a crowding reagent.

A crowding reagent is any compound (e.g., a biologic or synthetic polymer) having one of more of the functions described herein. It may function in a variety of ways to increase nucleic acid capture efficiency as described below. The crowding reagent may be a zwitterionic or neutrally charged agent that does not interfere with the charge interaction between the membrane and the array. A non-limiting example of a crowding reagent is polyethylene glycol (PEG). In some embodiments, PEG has a molecular weight equal to or greater than 1000 Da. Other examples of crowding reagents include but are not limited to dextan, ficoll, bovine serum albumin (BSA), and sucrose.

Thus, provided herein are methods of increasing the nucleic acid (e.g., transcript) capture rate per cell by including crowding reagents in multiple steps in the processes described herein. The crowding reagent may be used, for example, during nucleic acid (e.g., mRNA) binding to capture beads, during washing of the nucleic acid-bound beads before or after removal from the array, reverse transcription of the bound nucleic acid (e.g., RNA) to generate first strand nucleic acid (e.g., cDNA) whether in an open well or in bulk, and synthesis of second strand nucleic acid (e.g., cDNA), on the beads.

The mechanism by which crowding reagents improve transcript yields varies depending on when the reagent is used.

In some steps, the crowding reagent associates with or influences a significant fraction of solvent molecules in a solution, thereby effectively increasing the concentration of solutes in the solution. Although not intending to be bound by any particular theory, crowding reagents may disorder the solvent surrounding solutes, thereby increasing entropy and this results in molecular crowding as this term is understood in the art.

During RNA hybridization in the membrane-sealed well, the crowding agent cannot penetrate the semi-porous membrane due to size exclusion, thereby establishing an inward force on the membrane due to the lower osmotic pressure of the solution sealed in the wells (e.g., picowells). This inward force yields better sealing of the wells by the membrane, thereby decreasing loss of the well contents and reduced cross contamination. During bead washing and reverse transcription, the crowding reagent decreases the dissociation rate constant of the bead-bound RNA, thereby increasing the number of molecules that are reverse-transcribed into cDNA. Finally, inclusion of crowding reagent in the second strand cDNA synthesis reaction increases the hybridization rate of the second strand priming oligonucleotide (e.g., the randomer of FIG. 2B), yielding large increases in the amount of second strand cDNA.

The transcript capture yields using various PEG types is shown in FIG. 1 relative to the number of transcripts captured in the absence of a crowding agent. Addition of a crowding reagent such as PEG may lead to about a 50% increase in whole transcriptome amplification product and higher transcript capture per cell.

Regardless of the nature of the crowding reagent, the method may be used to increase nucleic acid (e.g., transcript) yield by at least 5%, at least 10%, at least 20%, at least 30%, at least 40% or at least 50% relative to capture in the absence of such crowding reagent. In some embodiments, the use of crowding agent may increase capture yield by at least 25% or by at least 50% relative to capture in the absence of such crowding reagent.

Crowding reagents may be used in a reaction mixture at a concentration of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%. In some embodiments, the crowding reagent is used in a reaction mixture at a concentration of 1%-15% or 5%-10%.

In some embodiments, the crowding reagent may be added to a reaction separately from other components or together with other components such as but not limited to reaction buffers, wash buffers or solutions. As an example, a crowding reagent may be added with (or in) a hybridization buffer such as that applied to a Seq-well array surface after cell lysis and/or along with (or in) a wash buffer that is used during removal of the beads from the Seq-well array.

Methods for Spatial Barcoding Well Arrays

The ability to link cellular function to single-cell RNA-seq will enable many applications involving single cell responses to perturbations including drugs, other cells or metabolites. The massively parallel nature of the Seq-well arrays provide enough replicates to empower multi-dose screens of a number of compounds or combinatorial screens of compounds using primary clinical samples or the identification of rare functional phenotypes, which could be immensely powerful in the realm of precision medicine. However, previously single cell functional activity could not be linked to the single cell transcriptome information acquired through Seq-well due to the random loading of the barcoded beads onto the well array, which made it impossible to trace back a given barcode sequence detected in sequencing data to a specific well or stimulation condition on the array. The methods of this disclosure overcome this limitation by delivering known, unique DNA spatial barcodes or unique combination of barcodes to each well. The spatial barcodes are leveraged to locate the well origin of each transcript, enabling linkage of transcript data with the results of other assays or treatments performed on the array. Spatially barcoded well arrays can also be used to acquire transcripts from thin tissue sections attached to glass slides, thereby retaining the 2D-location of each transcript within the original tissue structure. The spatial barcode delivery methods were further leveraged to co-deliver unique spatial barcodes with a matched unique stimulus to enable multi-drug combinatorial screens on the arrays.

There are a multiple ways of spatially barcoding an array. For example, it is possible to directly deliver a known barcode sequence to a known location on the Seq-well array using an inkjet printer or arraying device. As another example, a nucleic acid microarray, such as a DNA microarray, with nucleic acids of known sequence and location can be used to deliver the known sequences into individual picowells. In still other embodiments, spatial barcoding may involve the use of spectrally associate beads such as fluorescently-barcoded beads.

In one aspect, provided herein is a well array. In some embodiments, each well comprises a functionalized surface that comprises one or more nucleic acid molecules having a unique spatial barcode. In some embodiments, each unique spatial barcode is unique to one or a cluster of wells. In some embodiments, each well contains a unique combination of spatial barcodes. In some embodiments, each unique spatial barcode is co-delivered with unique stimuli. In some embodiments, the location of each spatial barcode on the array of wells is known.

In another aspect, provided herein is a method for spatially locating transcripts on said well array comprising contacting the well array with a population of cells containing one or more transcripts; generating cDNA from the transcripts on a standard barcoded capture bead such that the sequence of the unique bead barcode is incorporated into the cDNA; simultaneously releasing the unique spatial barcode from the well surface, enabling binding of the spatial barcode to the barcoded capture bead; generating a fusion of the spatial barcode and bead barcode by extending the bead capture probe through the hybridized spatial barcode sequence during the reverse transcription reaction; and locating the transcript on the well array by matching the bead barcode present in the cDNA molecule to a bead barcode-spatial barcode fusion sequence in the sequencing data.

It is to be understood that the term cDNA or first strand cDNA intend nucleic acid molecules that comprise nucleotide sequence that is complementary to a mRNA as well as nucleotide sequence that is not complementary to the mRNA. Examples of these latter sequences include the 5' UPS, a barcode nucleotide sequence, and the like. Thus, although for brevity some nucleic acids are referred to herein as cDNA or first strand cDNA, it should be noted that such nucleic acids comprise cDNA sequences as well as flanking sequences 5' and/or 3' to the cDNA sequence.

In another aspect, provided herein is a method for determining the transcriptional response to a set of stimuli or combinations of stimuli in cells on well array containing functionalized surfaces bound with unique spatial barcodes and matched stimulus comprising contacting the well array with a population of cells containing one or more transcripts; releasing stimuli from functionalized surface; culturing cells in wells long enough to enable transcriptional response to stimuli present in each well; generating cDNA from the transcripts on a standard barcoded capture bead such that the sequence of the unique bead barcode is incorporated into the cDNA; simultaneously releasing the unique spatial barcode from the well surface, enabling binding of the spatial barcode to the barcoded capture bead; generating a fusion of the spatial barcode and bead barcode by extending the bead capture probe through the hybridized spatial barcode sequence during the reverse transcription reaction; and linking the transcriptional response to a specific stimuli by matching the bead barcode present in the cDNA molecule to a bead barcode-spatial barcode fusion sequence in the sequencing data, which defines the stimuli or combination of stimuli present in the well.

In some embodiments, the functionalized surface is a wall of the well. In some embodiments, the functionalized surface is the bottom wall of the well. In some embodiments, each well of the well array comprises 1, 2, 3, 4, or 5 functionalized surfaces. In some embodiments, the functionalized surface is an object inserted into the well. In some embodiments, the functionalized surface is a bead. In some embodiments, the functionalized surface is a spectral bead.

In some embodiments, the well array is constructed on a microarray of unique spatial barcodes. In some embodiments, the well array is constructed on a surface printed with unique spatial barcodes. In some embodiments, unique spatial barcodes are transferred into the wells of well array.

In some embodiments, each unique spatial barcode is unique to one or a cluster of wells. In some embodiments, each unique spatial barcode is unique to 1, 2, 3, 4, 5, 6, 7, 8, 9, or 10 wells.

In some embodiments, the functionalized surface is functionalized with streptavidin and the spatial unique barcode is biotin labeled. In some embodiments, the functionalized surface is functionalized with an acrylic group. In some embodiments, the functionalized surface is functionalized with glyoxyl, thiols, amines, carboxyls, succinimide esters, epoxides, and/or thiocyanates. Virtually any covalent or non-covalent binding chemistry may be used to attach barcodes to surfaces such as well surfaces or beads as long as the linkage is reversible or cleavable.

In some embodiments, the methods further comprise releasing the nucleic acid molecules having a unique spatial barcode from the functionalized surface. In some embodiments, the nucleic acid molecules having a unique spatial barcode are released from the functionalized surface by a reducing agent such as a cell lysis buffer. For example, in some embodiments, the nucleic acid molecules having a unique spatial barcode are labeled with biotin through a disulfide linker and the functionalized surface is streptavidin-functionalized, creating a disulfide bridge which can be cleaved by a reducing agent, e.g., in the cell lysis buffer, releasing the nucleic acid molecules having a unique spatial barcode from the functionalized surface. In some embodiments, the nucleic acid molecules having a unique spatial barcode are released from the functionalized surface by cleavage of a photosensitive linkage. In some embodiments, the nucleic acid molecules having a unique spatial barcode are released from the functionalized surface by cleavage of an enzymatically cleavable linkage. In some embodiments, the spatial barcode is hybridized to a complementary oligonucleotide which is covalently linked to the surface. and is released by inducing DNA denaturation through temperature, a chaotrope or base.

As used herein a "spectrally-encoded bead" is a bead that has an optical signature. In some embodiments, a spectral bead is labeled with one or more dyes. In some embodiments, a spectral bead is labeled with 1, 2, 3, 4, 5, 6, 7, 8, 9, 10, 11, 12, 13, 14, 15, 16, 17, 28, 19 or 20 fluorophores. In some embodiments, a spectral bead is labeled with one or more dyes and one or more fluorophores. In some embodiments, a spectral bead is labeled with a mass label.

In some embodiments, the spectrally-encoded beads are about 3 to about 10 microns in diameter.

In some embodiments, the spectrally-encoded beads may be polystyrene or agarose beads.

In some embodiments, the spectrally-encoded beads are surface-functionalized with streptavidin and thus can be bound to biotinylated nucleic acid molecules having a unique spatial barcode. Streptavidin may be complexed to the bead surface and/or the oligonucleotide may be complexed with biotin through a dithiol linker.

In some embodiments, there are 1, 2, 3, 4, 5, 6, 7, 8, 9, or 10 spectrally-encoded beads per well.

In some embodiments, the location of the spectrally-encoded beads in the well array is visualized by epifluorescent microscopy.

In some embodiments, the unique spatial barcode is 3, 4, 5, 6, 7, 8, 9, 10, 11, 12, 13, 14, 15, 16, 17, 18, 19, 20, 21, 22, 23 24, 25, 26, 27, 28, 29, or 30 nucleotides, e.g., is from 10 to 30 nucleotides long.

In some embodiments, the nucleic acid comprising the unique spatial barcode further comprises a universal primer site. In some embodiments, the universal primer site is 10, 11, 12, 13, 14, 15, 16, 17, 18, 19, 20, 21, 22, 23, 24, 25, 26, 27, 28, 29, or 30 nucleotides long, e.g., 10-30, or 15-25 nucleotides long. In some embodiments, the nucleic acid comprising the unique spatial barcode further comprises a sequence that is complementary to a capture sequence on a nucleic acid attached to a transcript capture bead. In some embodiments, the sequence that is complementary to a capture sequence on a nucleic acid attached to a transcript capture bead is 5, 6, 7, 8, 9, 10, 11, 12, 13, 14, 15, 16, 17, 18, 19, or 20 nucleotides long. In some embodiments, the sequence that is complementary to a capture sequence on a nucleic acid attached to a transcript capture bead is a poly(dA) tract.

In some embodiments, the methods comprise contacting the well array with a population of cells containing one or more transcripts. In some embodiments, the cells are contacted with the well array at 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C.

In some embodiments, the cells are bacterial cells. In some embodiments, the cells are eukaryotic cells. In some embodiments, the cells are mammalian cells. In some embodiments, the cells are murine cells. In some embodiments, the cells are primate cells. In some embodiments the cells are human cells. In some embodiments, the cells are tumor cells. In some embodiments, the cells are non-mammalian cells and may be prokaryotic cells or other eukaryotic cells. The cells (or nucleic acid source) may be naturally occurring or it may be non-naturally occurring. An example of a non-naturally occurring nucleic acid is a synthetically produced cell.

In some embodiments, the methods comprise sealing the wells of the well array with a semi-permeable membrane.

In some embodiments, the methods comprise lysing the cells.

In some embodiments, the methods comprise generating cDNA from the one or more transcripts such that the sequence of the bead barcode is incorporated into the cDNA. Methods for generating cDNA from mRNA transcripts using reverse transcriptase are well known in the art. In some embodiments, the transcripts bind the capture sequence on the barcoded bead; simultaneously, the spatial barcode is released from the well surface and also binds a capture sequence on the capture bead; the beads are removed and both the bound spatial barcodes and transcripts are replicated by extending the capture oligonucleotide in a reverse transcription reaction, forming a first strand cDNA with the bead barcode fused to the transcript sequence or the spatial barcode sequence. In some embodiments, a second strand of cDNA is synthesized using the methods described here.

Thus, in some embodiments each well gives rise to two different but related second strand nucleic acids, one having the target nucleic acid sequence and the other having the spatial barcode sequence but both having the bead barcode sequence that can be used to ultimately associate both second strand nucleic acids.

In some embodiments, the transcript is located on the well array by matching the bead barcode in the cDNA to a bead barcode-spatial barcode fusion. In some embodiments, the location of the unique spatial barcode associated with a functionalized surface is known. In some embodiments, the functionalized surface is a spectral bead and the location of the unique spatial barcode is known by visualizing the spectral bead on the well array.

In some embodiments, the spectral beads further comprise a stimulus. In some embodiments, the stimulus is a drug. In some embodiments, the stimulus is attached to the spectral bead by a desthiobiotin-streptavidin bond. In some embodiments, the drug is contained in light sensitive micelles which are attached to the spectral bead. In some embodiments, the stimulus is attached to the spectral bead by a light sensitive covalent bond.

Figure 3A:
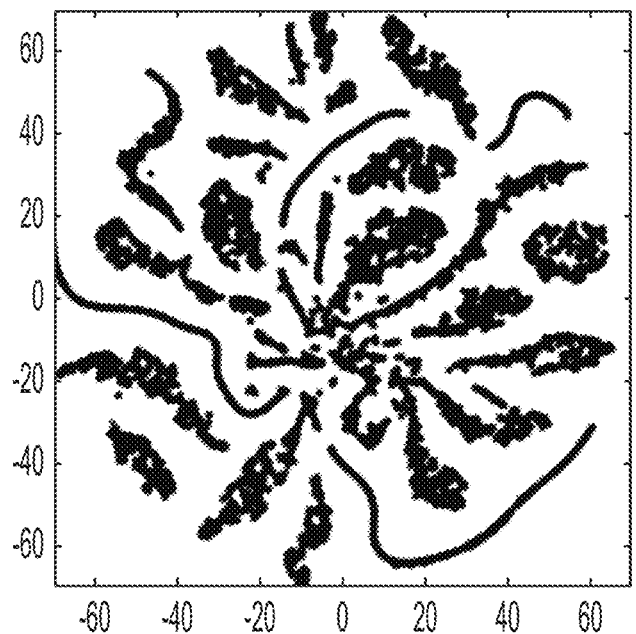
FIGS. 3A-3B: Spectrally barcoded particles. Glyoxyl-functionalized agarose beads were functionalized with combinatorial combinations of 5 different fluorescently-labeled streptavidin molecules, making 31 unique spectral barcodes. Beads were imaged using standard epifluorescent microscope in 5 spectral channels.
Figure 3B:
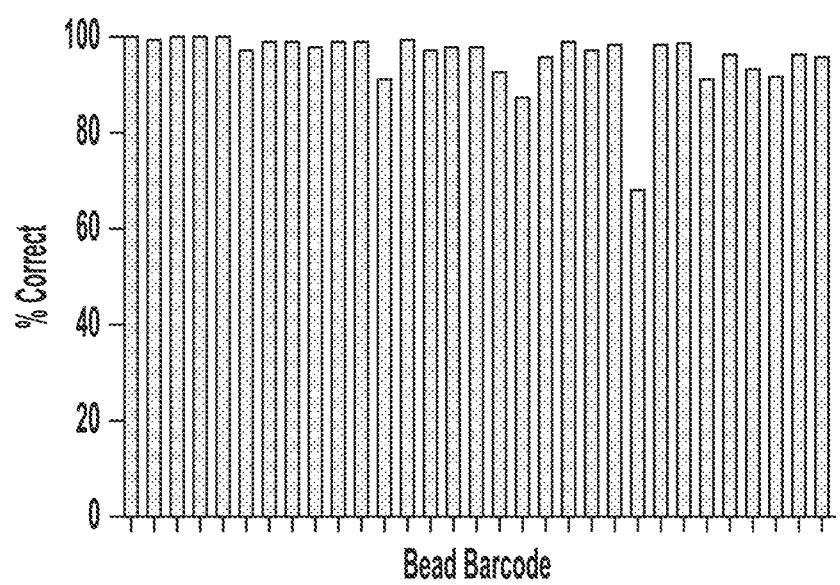
Figure 4:
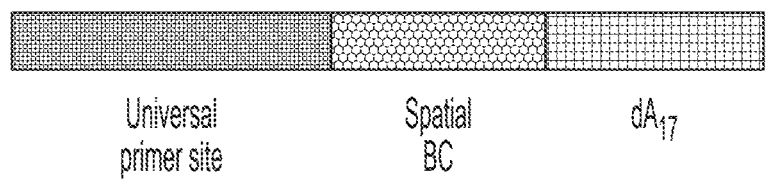
FIG. 4: Schematic of an embodiment of an oligonucleotide comprising a spatial barcode. The $dA_{17}$ could be replaced with a poly(dA) sequence of shorter or longer length. Capture oligonucleotides, such as those present on a capture bead, may comprise a poly(dT) sequence instead of a poly(dA) sequence, if designed to capture mRNA transcripts. Alternatively, they may comprise another capture sequence that is complementary to a sequence in the nucleic acid to be captured (also known as the target nucleic acid).

One exemplary implementation of the methods described herein comprises spatially locating transcripts on a well array using spectrally-encoded beads (FIGS. 3A and B). Beads can be labeled spectrally either through combinatorial combination of different quanta of a limited number of dyes, as provided commercially by companies such as Luminex or BD, combinatorial combinations of up to 16 different fluorophores or both, yielding a large number of potential spatial barcodes. Each unique spectrally-encoded barcoded bead is bound to a unique spatial barcode through a cleavable bond. One preferred method is using streptavidin-functionalized beads and oligonucleotides with a biotin molecule attached through a di-sulfide bridge, as the disulfide bond is cleaved by the reducing agent in standard cell lysis buffer. Other chemistries can be used including photosensitive or enzymatically cleavable linkages. The barcoded oligonucleotide consists of three parts, a universal primer site, the barcode sequence and a poly(dA) tract to mediate binding to the poly(dT) sequences on the transcript capture bead (FIG. 4). The barcoded beads are loaded into the array at a density that yields multiple beads per well. Barcoded bead loading can be performed either before or after the other cell assays are performed depending on concerns of whether the transcriptome will change during bead loading or whether the presence of the beads disrupts the other assays. After all cell functional assays are complete and the barcoded beads are loaded, the array is imaged to define which combination of spatially barcoded beads was present in each well. Finally, the standard DNA-barcoded transcript capture beads are loaded into the array and Seq-well is performed as described. In some embodiments, the barcoded transcript capture beads are loaded last if they are auto-fluorescent and prevent the image acquisition of the spatially barcoded beads if present though changes in the chemistry of the transcript capture bead may allow these beads to be present throughout. While the wells are still sealed with the porous membrane, the unique spatial bead barcode must be released from the spatially barcoded bead, using light, enzymes or preferably the reducing agent present in the cell lysis buffer. After release, a portion of the spatial barcode binds the transcript capture bead. Bound oligos are extended during the standard reverse transcription reaction yielding a fusion between unique spatial bead barcode and the transcript capture barcode contained on the transcript capture bead. These fusion events can be amplified using the primer sites on the unique spatial bead barcode oligonucleotide and transcript capture beads and sequenced using standard chemistries (Examples 2 and 3). The combination of unique spatial barcode oligonucleotides associated with any transcript capture barcode can be matched to the combination of spectral beads present in each well to link sequencing data back to a particular well. Spatial barcoding through spectral beads has limitations in that it requires a large number (100s) of different spectral beads, which can be challenging to make and accurately distinguish using epifluorescent microscopy, and a relatively high number of beads per well (e.g., 4-5) to give unique combination of beads/well, further complicating accurate image processing and requiring that spatial spectral bead barcodes from all beads present in a well are captured in sequencing space. These limitations make it most useful for lower density (1000s of wells) well arrays but it is an inexpensive option that can be readily applied to any Seq-well array.

A second exemplary implementation of the methods described herein comprises spatially locating transcripts on a well array using DNA microarrays to deliver known oligonucleotides to each well (FIGS. 5A-D). In some embodiments, this approach entails making DNA microarrays of the reverse complement of the unique spatial barcode oligonucleotides described above (FIG. 4) in which each DNA microarray feature has a unique spatial barcode sequence. In some embodiments is preferably accomplished through commercial in situ DNA synthesis, particularly for denser microarrays which contain up to 1 million unique barcode sequences. The size and spacing of the DNA microarray features are designed such that when sealed against a well array in any registration, every well will have access to at least a portion of the area of a microarray feature and no microarray feature can span two wells. A fluorescently-labeled oligonucleotide complementary to the universal primer site is hybridized to the microarray and then enzymatically extended using a standard DNA polymerase, yielding double-stranded microarray features containing the unique spatial barcode. In some embodiments, the spatial barcode sequence is synthesized directly on the array if it is attached to the array surface through a cleavable bond, such as a bond cleavable by light, reducing agent or an enzyme. The spatial barcode-bearing microarray can then be used to deliver the barcodes to a well array through a top-down (FIG. 5A, Example 2) or preferably bottom-up (FIG. 5C, Example 3) process.

Figure 5A:
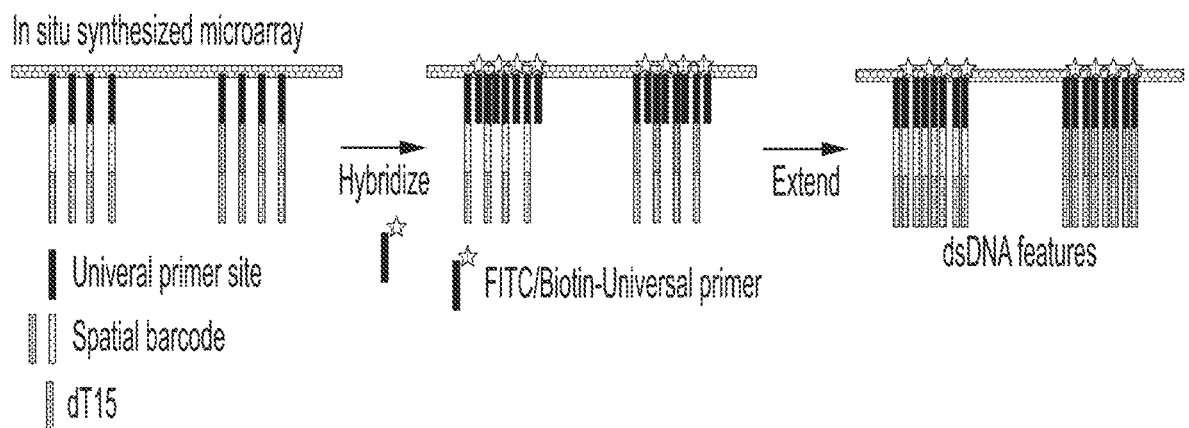
FIGS. 5A-5D: DNA microarray-mediated spatial barcoding of picowell arrays.
Figure 5B:
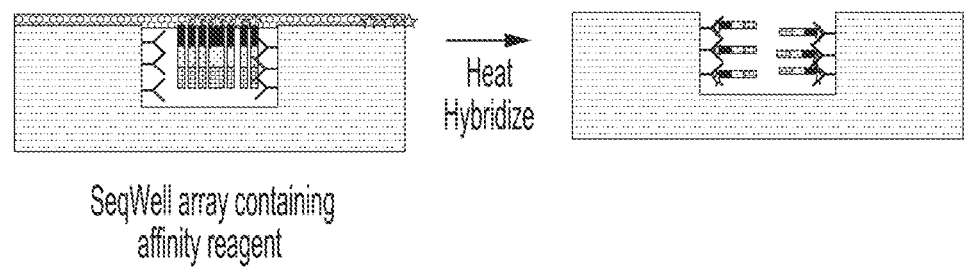
Figure 5C:
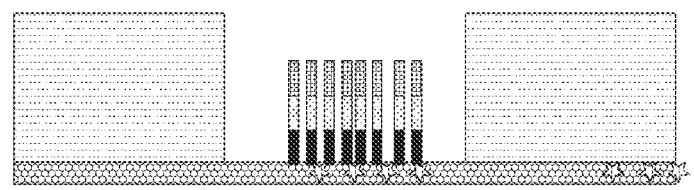
Figure 5D:
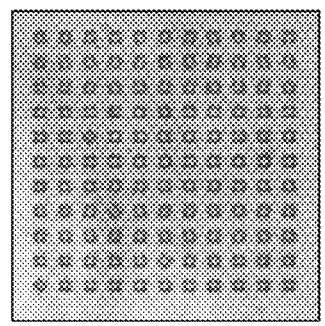

In the top-down delivery scheme (Example 2), the oligonucleotide used to prime the second strand on the microarray also has a biotin linker containing a bond that is cleavable by light, reducing agent or an enzyme. Prior to the cell assay being performed, the inner well surfaces of a standard Seq-well microarray can be functionalized with streptavidin molecules, preferably through carbodiimide chemistry or other covalent chemistries known in the field. The double stranded microarray can then be used to seal the well array (FIG. 5A). Fluorescent microscopy can be used to determine the alignment of the DNA microarray features and the well grid (FIG. 5B). The sealed array can then be heated to denature the double stranded microarray features. A portion of the released oligos are captured on the well surface through the biotin-streptavidin bond. The well array is now said to be spatially barcoded and can be used for cell functional assays. After the assays are complete, barcoded transcript capture beads are loaded and Seq-well can be performed as normal. During lysis, the reducing agent cleaves the oligonucleotide-biotin bond releasing the spatial barcode for capture on the transcript capture beads. The unique spatial barcode is again fused to the transcript capture barcode during reverse transcription, amplified and sequenced as described above. Microarray delivery of spatial barcodes in general is preferred because it requires only a single barcode per well to be successfully captured on the transcript capture bead and in sequencing space, making it technically less challenging. Also, defining the registration of the spatial barcodes and well arrays is a much more straight forward image processing step. The top-down delivery approach benefits include being able to use standard Seq-well picowell arrays.

In the bottom-up delivery scheme (FIG. 5C, Example 3), the well array is synthesized on top of the DNA microarray, making the bottom of each well the DNA microarray surface. This is accomplished by functionalizing the DNA microarray with a functional group that can be used to link the DNA microarray surface with the material used to synthesize the well array, a preferred implementation is an acrylic group and in combination with 3D stereolithography crosslinking of an acrylic resin to covalently link and build the array on top of the DNA microarray. DNA microarray functionalization is preferably accomplished by treating the in situ-synthesized DNA microarray prior to final nucleotide ring deprotection with an acrylic containing phosphoramidite such as acrydite. Standard oligonucleotide deprotection and second-strand synthesis is completed followed by well array synthesis on the DNA well array. Alternatively, acrylic functional groups can also be added to the DNA microarray through vapor deposition of an acrylic silane or the DNA microarray could be initially synthesized on a glass slide pre-functionalized with acrylic groups. When completed, fluorescent microscopy is again used to determine the registration between the DNA microarray and well grid. The synthesized well array is then functionalized using described chemistries to make it compatible with the standard Seq-well protocol. The arrays are then used for cell assays and transcript capture as described in the top-down method. The unique spatial barcode can be released by the denaturing cell lysis buffer. The bottom-up approach is preferable to the top-down method because it is more scalable since the barcodes are integrated into the well array synthesis. There is also a lower chance of leakage of unique spatial barcodes between wells since the barcodes are not released until the wells are fully sealed by the semi-porous membrane. These barcoded arrays are also reusable, after regenerating the double stranded barcode.

Figure 6A:
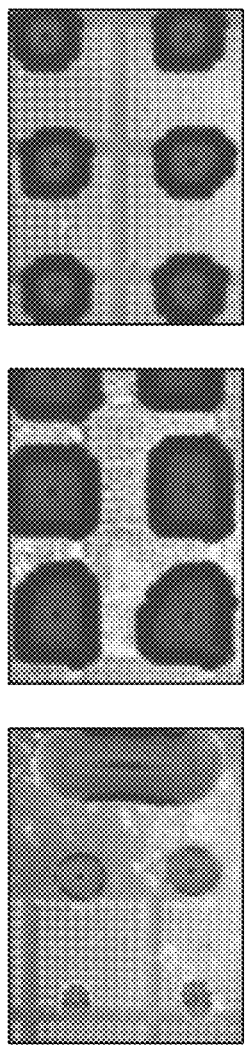
FIGS. 6A-6C: Delivery of compounds to individual wells in picowell arrays.
Figure 6B:
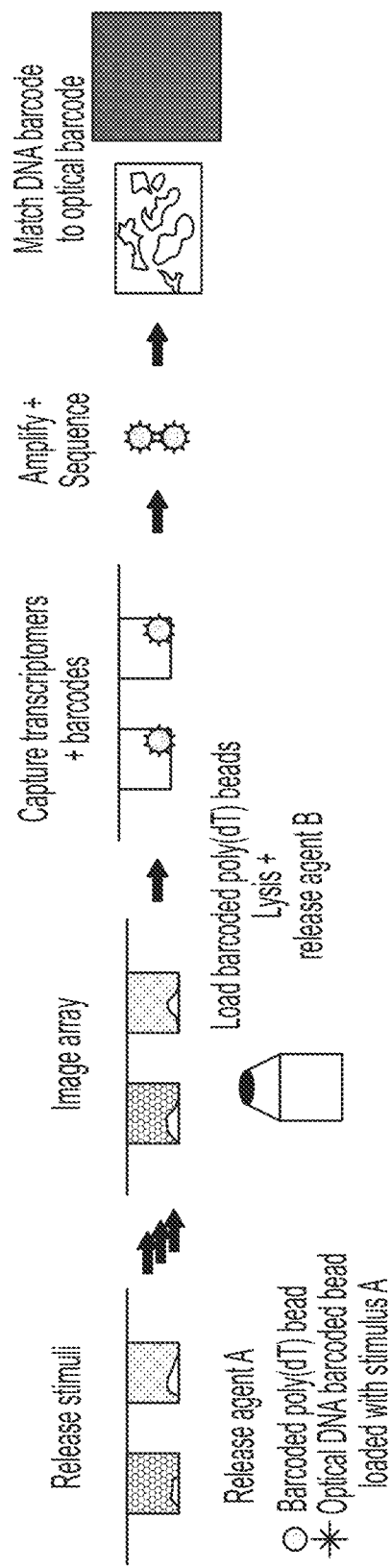
Figure 6C:
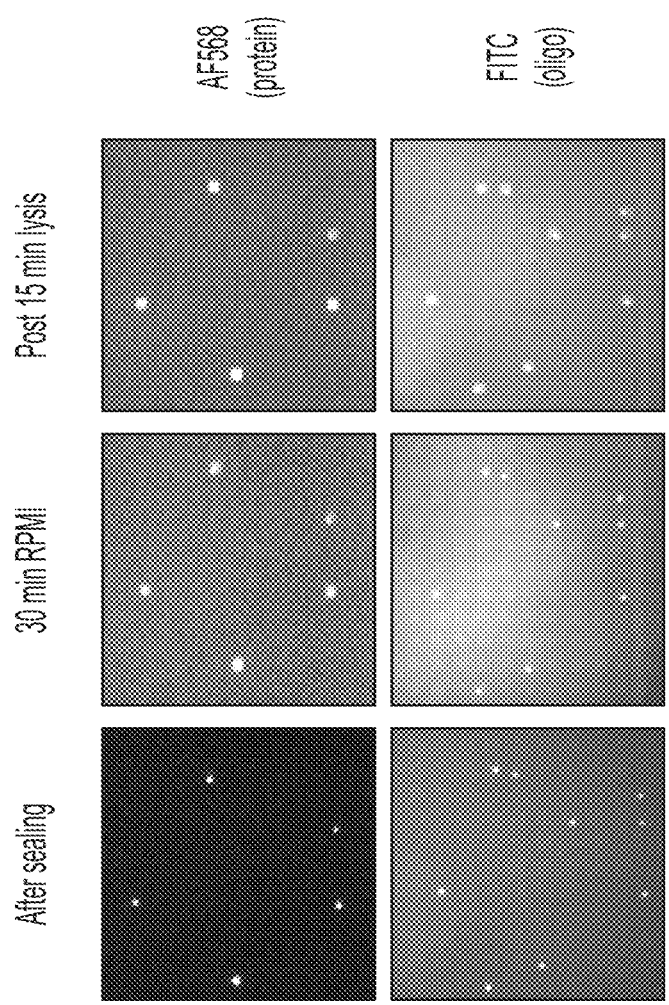

A third exemplary implementation of the methods described herein comprises linking transcriptional responses to a set of individual or combination of stimuli through the use of functionalized surfaces co-loaded with a spatial barcode and a matching unique stimulus (FIG. 6). Co-functionalized surfaces can be created through functionalizing the inner walls of a well array with a crosslinking chemistry such as streptavidin and then using a modified ink jet printer to print different molecules onto different segments of the array along with matching spatial barcodes (FIG. 6A), both of which are functionalized to link to the functional groups bound to the well surface. Alternatively, beads are co-loaded with matching unique stimuli and spatial barcodes and randomly loaded onto the array (FIG. 6B). In either approach, the drugs are stably associated with the functionalized surface through a mechanism that enables inducible drug release in conditions benign to the cells. One approach is the linkage of the drug to the surface through a desthiobiotin-streptavidin bond, which is released by biotin present in standard cell media (FIG. 6C). Following drug release, the cells are cultured to allow for transcriptional response to each drug. After an appropriate incubation, the transcripts are captured on barcoded beads as described above as are the co-delivered spatial barcodes. The single cell transcriptional responses to a given stimulus is determined by identifying bead barcodes fused to the spatial barcode specific for that particular stimulus.

Improved Hardware for Performing Well-Based Assays and Analyses Such as but not Limited to Seq-Well Membrane Applicator In another aspect, provided herein is a membrane applicator for applying a semi-porous membrane to a well array. Seq-well requires the attachment of a semi-porous membrane to the array surface to achieve optimal transcript capture. In the initial protocol, a plasma-activated polycarbonate membrane was attached to the picowell array through a mechanically challenging method of holding the membrane against the array in the proper location with one glass slide and then running a second glass slide against the back of the membrane to remove any liquid from between the membrane and the array. This step poses several challenges to the scalability, portability and ease of use of the technique. Plasma activation is essential for membrane attachment, but requires special equipment (i.e. a plasma oven), requiring centralized activation of the membranes for widespread adoption of the technique. However, plasma-treated membranes are extremely flimsy, both dry and in a hydrated state, making it extremely challenging to ship and reproducibly preform membrane attachment without significant training. Finally, each membrane is processed individually, limiting the scalability of the assay.

Figure 7:
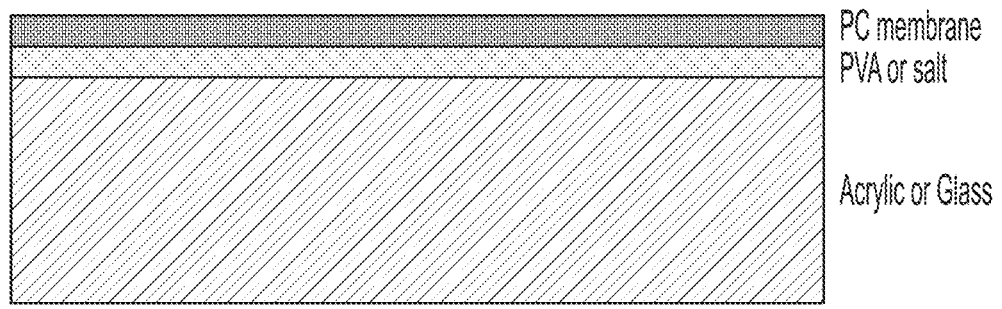
FIG. 7: Membrane applicator. Schematic of the layers of the membrane applicator. From top to bottom: PC membrane, PVA or salt, Acrylic or Glass.
Figure 8A:
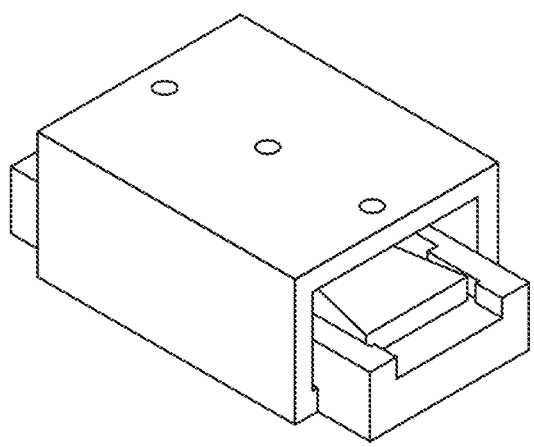
FIGS. 8A-8D: Schematic of plastic clamp.
Figure 8B:
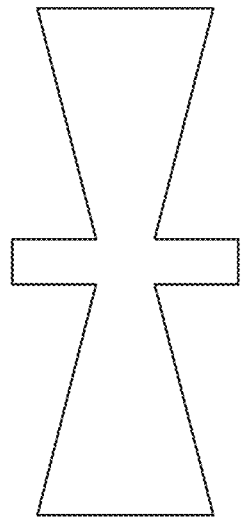
Figure 8C:
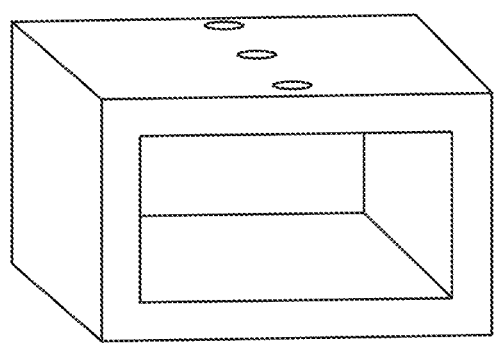
Figure 8D:
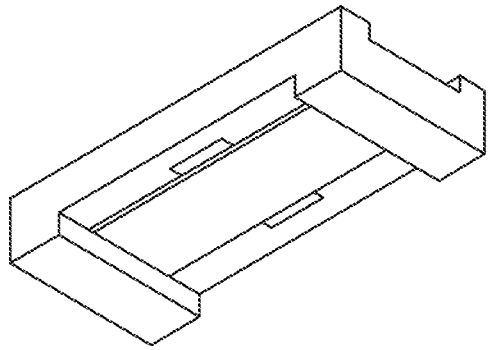
Figure 9A:
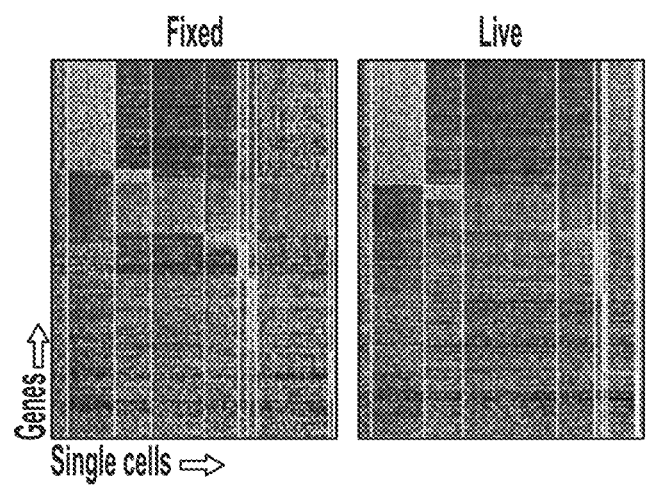
FIGS. 9A-9E: Metrics of single cell RNAseq libraries acquired from live cells or cells fixed with 80% methanol after being loaded into the array.
Figure 9B:
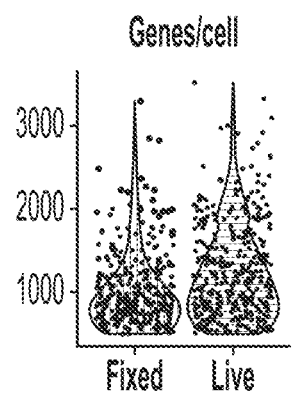
Figure 9C:
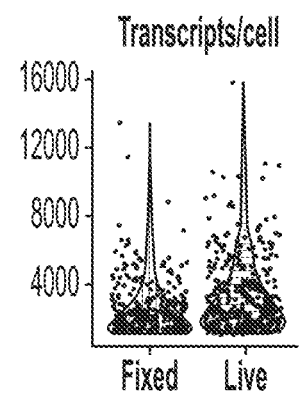
Figure 9D:
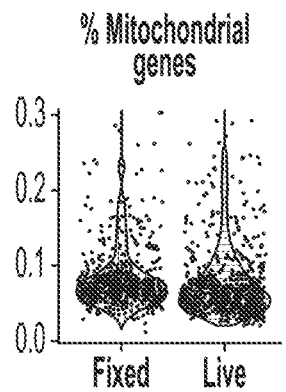
Figure 9E:
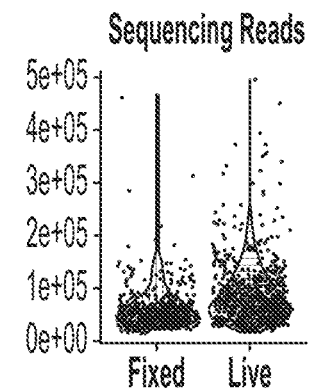

Presented herein is a membrane applicator that surprisingly overcomes these challenges. The generalized form of the applicator consists of the membrane attached to rigid backing of glass or preferably acrylic plastic through a reversible chemistry, e.g., a hydrophilic thin film (FIG. 7). In the simplest form, the thin film is a salt bridge, but ideally consists of a hydrophilic polymer, enabling a thicker film to be achieved. The applicator solves the shipping problem as activated membranes are stable for extended periods adhered to the rigid backing in a dry state, enabling shipping membranes in standard microscope slide containers. Scalable production of individual membranes is enables through the use of a clear acrylic support and a thicker polymeric thin film. Using these materials, large, bulk applicators can be constructed. The acrylic backing enables laser cutting of the bulk applicator into 100s of individual applicators. The thicker thin film is required to prevent fusion of the membrane to the acrylic backing during laser cutting, enabling detachment of the membrane during application. Finally, the applicator dramatically simplifies attachment of the membrane to the array, as the entire applicator can be placed on top of the array as a single dry piece. Following clamping and incubation, the applicator:array sandwich is submerged in solution. The hydrophilic thin film absorbs water, releasing the membrane from the applicator and leaving the membrane attached to the array. Therefore, the applicator negates the need for the end user to handle the flimsy membranes and perform the standard, error-prone membrane attachment procedure.

In one embodiment, provided herein is a membrane applicator comprising a membrane; and a rigid support; wherein the membrane is attached to the rigid support through a reversible chemistry.

In some embodiments, the rigid support comprises glass. In some embodiments, the rigid support comprises acrylic plastic. In some embodiments, the rigid support comprises polycarbonate or polystyrene.

In some embodiments, the rigid support is about 1 to about 2 mm thick. In some embodiments, the membrane is a semi-porous membrane. In some embodiments, the membrane is a plasma-activated. In some embodiments, the membrane is polycarbonate.

In some embodiments, the membrane is attached to the rigid support through a reversible chemistry. In some embodiments, the reversible chemistry is a hydrophilic thin film. In some embodiments, the hydrophilic thin film is a salt bridge. In some embodiments, the hydrophilic thin film is a hydrophilic polymer such as polyacrylamide, poly(vinyl alcohol), agarose or alginate. In some embodiments, the reversible chemistry is a disulfide bridge created by a biotin-streptavidin interaction which can be cleaved by a reducing agent. In some embodiments, the reversible chemistry is a photosensitive linkage. In some embodiments, the reversible chemistry is an enzymatically cleavable linkage.

In some embodiments, the membrane applicator is 20, 21, 22, 23, 24, 25, 26, 27, 28, 29, or 30 mm wide. In some embodiments, the membrane applicator is 70, 71, 72, 73, 74, 75, 76, 77, 78, 79, or 80 mm long. In other embodiments, the membrane applicator may be much larger including for example 1-5 feet by 1-5 feet (e.g., 2 feet×2 feet, or 2 feet by 3 feet). Use of these larger applicator enables the sealing of a plurality of arrays simultaneously.

Array Clamp

To induce a complete seal between the membrane and the well array, the membrane must be pressed against the array with a rigid backing for an extended period of time at elevated temperature, typically 37° C. for 30 minutes. The traditional protocol utilizes a commercial $450 steel hybridization clamp. The high cost of the clamp limits the number of samples of that can be processed simultaneously and represents a friction point for the adoption of the technology in new labs.

To facilitate rapid adoption of the technology in new labs, provided herein is a redesigned manual clamp to function when constructed of more pliable and cheaper plastic material (FIGS. 8A-D). There were three keys to engineering a clamp that works in plastic. 1. Pressure needed to be applied along the long axis of the array. If a single screw in the middle was used, the top piece bowed providing poor sealing at the ends of the array. A three screw design was found to be optimal for providing downward force along the long axis. 2. Upward force applied directly under the array. This was accomplished by creating a square clamp that completely encompassed the array holder and top piece and only touched the array holder underneath the array causing the upward force to be under the array. 3. Allow path for fluid to leave the array surface. The design presented herein can be injection molded for <$15, making the clamp a disposable item that can be sent to new labs along with the membranes and arrays. The cheap costs also enables large numbers of clamps to be available, increasing the throughput of heavy user labs or cores.

Scalable Array Clamping with a Heated Press

In another aspect, provided herein is a method for sealing a well to an array using a heated press. Manual clamping of each array still represents a bottleneck in the throughput of the assay for heavy user labs. The press consists of an elastic bottom surface on which the arrays are placed. Membranes can either be previously place on the arrays using the standard procedure or more preferably, a membrane applicator is placed on top of the arrays. As stated, the top surface of the press is heated to a defined temperature, typically 37° C. The press is then closed at a defined pressure for a defined amount of time, to mediate membrane attachment. The heated press method has several advantages for heavy user labs. Current press dimensions, enable membrane attachment to 50 arrays simultaneously. Improved heat transfer of the press compared to an oven, enables membrane attachment in 5 minutes instead of 30 minutes. Finally, a single membrane can be used to seal all fifty arrays, which facilitates scaling of the technology by requiring fewer individual membranes to be made and aids users as well by enabling simultaneous removal of the membrane from all arrays instead of one at a time after transcript capture.

In some embodiments, the method for sealing a membrane to a well array comprises contacting a well array with a membrane; and applying a heated surface to the membrane contacted to the well array.

In some embodiments, the membrane comprises a rigid support, e.g., a rigid support described herein, with the membrane facing the well and the rigid support facing the heated surface. In some embodiments, the membrane comprises a membrane applicator described herein.

In some embodiments, the heated surface is heated to 30° C., 31° C., 32° C., 33° C., 34° C., 35° C., 36° C., 37° C., 38° C., 39° C., 40° C., 41° C., 42° C., 43° C., 44° C., 45° C., 46° C. 47° C., 48° C., 49° C., 50° C., 51° C., 52° C., 53° C., 54° C., or 55° C. In some embodiments, the heated surface is heated to 35° C.-50° C.

In some embodiments, the heated surface is applied to the membrane for 1, 2, 3, 4, 5, 6, 7, 8, 9, 10, 11, 12, 13, 14, or 15 minutes. In some embodiments, the heated surface is applied to the membrane for less than 10 minutes. In some embodiments, the heated surface is applied to the membrane for 5 minutes.

In some embodiments, a heated press comprises a heat press. In some embodiments, a heated press comprises a t-shirt press. In some embodiments, a heated press comprises an iron.

Methods to Magnetize Porous Plastic Particles or Beads

Magnetic particles have become resins of choice for most biological assay that utilize particles because it dramatically simplifies separation of particles from solution and enables automation. Magnetic capture beads, such as magnetic barcoded transcript capture beads, would streamline much of the enzymatic reactions performed after transcript capture during Seq-well, but magnetic beads have to date not been used. The transcript capture beads utilized in Seq-well have multiple specifications that are essential for the assay including a large size (e.g., about 35 microns), highly uniform size distribution, macroporosity (>100 nm pores), and dense surface functionality. There are very few commercial resins that meet these specifications and none is magnetic. To avoid creating magnetic resins from scratch, a facile method for magnetizing commercially available, porous resins has been devised. The method utilizes either solvent or temperature to cause contraction of the polymer used to make the resin, preferable is an aqueous solution of 4M NaCl, 10% PEG8000 at −20° C. Shrinkage of the resin induces the pores within the resin to become larger. In the shrunken state, magnetic particles, sized to be slightly larger than the pores in the normal state, preferably 50-100 nm, are mixed with the resin. After the particles permeate the pores of the resin in the shrunken state, the resin is brought back to standard solvent condition and standard temperature. As the pores return to normal, magnetic particles are permanently trapped within the pore structure, yielding magnetic resin.

Methods for Stable Storage of Single Cell RNA

Currently, single-cell RNAseq analysis sparse cell samples require processing the sample to barcoded cDNA on the day of acquisition due to poor cell recovery after standard bulk freezing processes. This is a significant limitation of the technology as it requires the appropriate instrumentation to be available at or near the site of sample acquisition and requires processing every sample to the cDNA stage which can be cost- and time-intensive, prohibitively so for large clinical trials. To overcome this limitation, we have developed methods to leverage picowell arrays such as Seq-Well arrays to function as single cell RNA storage vehicles for thousands of cells. Cells are loaded into functionalized picoarrays preloaded with barcoded capture beads in a matter of minutes. The array is then submerged in an alcohol fixative (e.g., methanol) to precipitate the contents of each cell, and thereby hold such contents in the well during cell lysis, content precipitation and ultimately during storage. We have demonstrated that fixing cells with alcohol (e.g., methanol) once loaded into arrays has minimal effect on transcript recovery from the cells (FIGS. 9A-E). The array can then be placed into long term storage at a temperature below 0° C., including for example at about −80° C. or at about −20° C. To recover single cell transcriptomes from the stored arrays, a semi-porous membrane is attached to the array in the alcohol fixative. The Seq-Well protocol, or any other protocol involving picowells or picowell arrays is then performed. The robust denaturing lysis buffer re-dissolves the precipitated material, enabling capturing of the RNA at single cell resolution Layered Devices Layered devices (e.g., microfluidic devices, arrays of wells, e.g., comprising a dry film of photoresist) having through-holes and/or an array of wells (e.g., an array of microwells) having a plurality of wells configured such that each well can accommodate one cell and/or bead, and associated methods are disclosed herein. In some embodiments, such devices comprise a base layer which is optionally a porous membrane. In some embodiments, the dry film of photoresist having through-holes and/or an array of wells further comprises a second (e.g., a second or top layer of) dry film of photoresist having through-holes and/or an array of wells. The array of wells/bottomless microwell arrays are advantageously fabricated from a dry film of photoresist without the use of a solid support, providing several advantages over arrays and fabrication methods in the art.

Other types of arrays of wells (e.g., comprising solid well bottoms that do not allow liquid to pass through) may only allow for Poisson loading of cells and/or beads into the array, resulting in significantly lower throughput than can be achieved using a layered device of this disclosure (e.g., a layered device comprising well bottoms comprising a porous membrane which allow liquid comprising cells and/or beads to be flowed through the porous membrane of the layered device).

Other methods for making layered devices (e.g., arrays of wells, e.g., arrays of microwells) may be limited with respect to scalability and/or reproducibility. In alternative device fabrication methods to those described herein, photoresist may be spin-coated onto a solid support surface. These methods may be followed by exposing and developing an array of through-holes in the photoresist and then releasing the photoresist film from the support by a mechanical method (e.g., by using a razor blade to scrape off the photoresist film from the support). Such mechanical methods may not easily be applied to a large area photoresist film (e.g., larger than 0.1 m in length by 0.1 m in width), and may not be easily reproducible. Another alternative method of detaching a photoresist from a solid surface may involve spin-coating a photoresist onto a dissolvable solid support, called a lift-off layer. However, this method may add considerable complexity to the manufacturing process. Other alternative methods of making a device include using polydimethylsiloxane (PDMS) to make an array of microwells, but these methods may be difficult to apply to a large area of PDMS (e.g., larger than 0.1 m in length by 0.1 m in width), and may not be easily reproducible.

Advantageously, methods of making layered devices disclosed herein may be carried out with a dry film of photoresist and without any solid support for the dry film of photoresist, other than a photomask which may naturally detach from the dry film of photoresist during exposure to a developing solution. Methods of making layered devices disclosed herein may more easily be applied to a large area photoresist film (e.g., larger than 0.1 m in length by 0.1 m in width), and may be more easily reproducible than alternative methods. For example, methods disclosed herein may be used to make at thousands or tens of thousands in a reproducible manner in short periods of time and without significant manpower, including for example making at least 10,000 arrays per day with a few technicians.

Methods of making free-standing structures (e.g., bottomless arrays of wells) comprising a dry film of photoresist without a need for a solid support for the dry film of photoresist other than a photomask has significant utility beyond the robust, facile and reproducible manufacture of arrays of wells.

In alternative devices to those described herein, a bottomless array of wells may be supported by a chitosan layer, which forms the bottom surface of the wells. These alternative arrays having a chitosan layer typically have a pore size and/or flux so low as to prevent or hinder moving liquid there-through quickly enough for the purpose of loading cells and/or beads at high throughput, and/or for the purpose of super-Poisson loading the array of wells with cells and/or beads. Arrays of wells disclosed herein may have a significantly higher flux and/or a significantly higher pore size than these chitosan-layered arrays, and therefore facilitate loading cells and/or beads at high throughput and/or super-Poisson loading the array of wells.

Devices

In some embodiments, a layered device (e.g., microfluidic device, array of wells, e.g., comprising a dry film of photoresist) is provided. In some embodiments, a layered device comprises a plurality of layers. Layers in a layered device may include, e.g., one or more porous membranes, one or more bottomless arrays of wells, and/or one or more ultrafiltration membranes.

As is used herein, a "bottomless microwell array" comprises a planar substrate having a plurality of through-holes. In some embodiments, a bottomless microwell array comprises about $10^3$ or more through-holes, e.g., $10^3$ to about $10^7$ through-holes, about $3\times10^3$ to about $10^7$ through-holes, about $5\times10^3$ to about $10^7$ through-holes, about $10^4$ to about $10^7$ through-holes, about $10^4$ or about $5\times10^4$ or about $8\times10^4$ through to about $10^5$ or about $5\times10^5$ or about $1\times10^6$ or about $5\times10^6$ or about $1\times10^7$ through-holes. In some embodiments, a bottomless microwell array is state of the microwell array when it is not bound to a porous membrane at bottom.

Wells

In some embodiments, the layered device comprises a free standing photoresist film comprising a plurality of through-holes or wells (e.g., a bottomless array of wells, e.g., a bottomless microwell array).

In some embodiments, a layered device comprises an array of wells. In some embodiments, each well of the array of wells comprises one of a plurality of through-holes (e.g., in a dry film of photoresist) and a bottom surface (e.g., comprising a base layer, e.g., comprising a porous membrane). In some embodiments, wells in an array of wells described herein are configured to capture a single cell and/or bead. In some embodiments, wells in an array of wells described herein are arranged in a hexagonal pattern. In some embodiments, wells in an array of wells described herein are arranged in a square or rectangular grid pattern.

In some embodiments, the terms "microwell" or "well" or "through-hole" are used interchangeably and refer to a well having a largest lateral dimension or a diameter, e.g., a uniform diameter, of less than or equal to 1000 microns (e.g., between or equal to 1 micron and 1000 microns).

A well can be any shape and having at least sides and, optionally, a bottom surface. In some embodiments, at least some of (e.g., all of) the wells in an array of wells, and/or through-holes in a layer (e.g., dry film of photoresist), have a shape that is cylindrical, rectangular prism (e.g., having a square cross-section), pyramidal, or conical.

As used herein, the term "largest lateral dimension" of a feature (e.g., a well) in a layer (e.g., a photomask, a bottomless array of wells) refers to the maximum distance between two edges (e.g., two opposite edges, two diagonal edges) of the same feature (e.g., well) in a plane (e.g., any plane, a specific plane) parallel to the plane of a layer (e.g., bottomless array of wells) on which and/or in which the feature is located. For example, for wells with a circular cross-section, the largest lateral dimension in a plane parallel to the plane of the array of wells is the diameter of the circular cross-section in the plane. As another example, for wells with a rectangular cross-section (e.g., square cross-section), the largest lateral dimension in a plane parallel to the plane of the array of wells is the length of the diagonal of the rectangular cross-section in the plane. As used herein, the term "largest lateral dimension" of an article (e.g., a cell, a bead) refers to the maximum distance between any two edges of the same article (e.g., a cell, a bead).

In some embodiments, at least some of (e.g., all of) the wells in an array of wells, and/or through-holes in a layer (e.g., dry film of photoresist), have a shape that is cylindrical, rectangular prism (e.g., having a square cross-section), pyramidal, or conical.

Wells in an array of wells described herein, and/or through-holes in a dry film of photoresist, may have a suitable largest and/or smallest lateral dimension. In some embodiments, wells in an array of wells described herein, and/or through-holes in a dry film of photoresist, have a largest and/or smallest lateral dimension of at least 5 microns, at least 7 microns, at least 10 microns, at least 20 microns, at least 45 microns, at least 50 microns, or at least 100 microns. In some embodiments, wells in an array of wells described herein, and/or through-holes in a dry film of photoresist, have a largest and/or smallest lateral dimension of at most 500 microns, at most 400 microns, at most 300 microns, or at most 200 microns. Combinations of the above-referenced ranges are also possible (e.g., in a range of 5 microns to 500 microns, 7 microns to 400 microns, 5 microns to 50 microns). Other ranges are also possible. In some embodiments, wells in an array of wells described herein, and/or through-holes in a dry film of photoresist, have a largest and/or smallest lateral dimension in a range of 5 microns to 500 microns (e.g., 45 microns, 7 microns, 10 microns).

As used herein, when a quantitative characteristic (e.g., largest lateral dimension) is described as "in a range of," when accompanied by a smaller value and a larger value, this refers to the quantitative characteristic having a value between the smaller value and the larger value or equal to the smaller value of the larger value.

In some embodiments, at least some of (e.g., all of) the wells of a bottomless array of wells (e.g., a bottomless microwell array), and/or through-holes in a dry film of photoresist, have a uniform depth.

In some embodiments, at least some of (e.g., all of) the wells of a bottomless array of wells (e.g., a bottomless microwell array), and/or through-holes in a dry film of photoresist, have a depth such that at most several beads and/or cells (e.g., a single bead and/or a single cell) would fit inside of a well and/or through-hole. In some embodiments, at least some of (e.g., all of) the wells of a bottomless array of wells (e.g., a bottomless microwell array), and/or through-holes in a dry film of photoresist, have a depth equal to that of the thickness of the bottomless array of wells and/or the dry film of photoresist. In some embodiments, at least some of (e.g., all of) the wells of a bottomless array of wells (e.g., a bottomless microwell array), and/or through-holes in a dry film of photoresist, have a depth of at least 5 microns, at least 10 microns, at least 20 microns, or at least 30 microns. In some embodiments, at least some of (e.g., all of) the wells of a bottomless array of wells (e.g., a bottomless microwell array), and/or through-holes in a dry film of photoresist, have a depth of at most 500 microns, at most 200 microns, or at most 100 microns. Combinations of the above-referenced ranges are also possible (e.g., in a range of 5 microns to 500 microns, 10 microns to 200 microns, 30 microns to 100 microns). Other ranges are also possible. In some embodiments, at least some of (e.g., all of) the wells of a bottomless array of wells (e.g., a bottomless microwell array), and/or through-holes in a dry film of photoresist, have a depth in a range of 5 microns to 500 microns (e.g., 30 microns to 100 microns).

In some embodiments, at least some of (e.g., all of) the wells of a bottomless array of wells (e.g., a bottomless microwell array), and/or through-holes in a dry film of photoresist, have a uniform largest lateral dimension.

In some embodiments, at least some of (e.g., all of) the wells of a bottomless array of wells (e.g., a bottomless microwell array), and/or at least some of (e.g., all of) the through-holes in a dry film of photoresist, have a largest lateral dimension such that at most several beads and/or cells (e.g., a single bead and/or a single cell) would fit inside of a well and/or through-hole. In some embodiments, at least some of (e.g., all of) the wells of a bottomless array of wells (e.g., a bottomless microwell array), and/or at least some of (e.g., all of) the through-holes in a dry film of photoresist, have a largest lateral dimension (e.g., uniform diameter) of at least 1 micron, at least 10 microns, or at least 15 microns. In some embodiments, at least some of (e.g., all of) the wells of a bottomless array of wells (e.g., a bottomless microwell array), and/or at least some of (e.g., all of) the through-holes in a dry film of photoresist, have a largest lateral dimension (e.g., uniform diameter) of at most 500 microns, at most 300 microns, at most 200 microns, at most 100 microns, or at most 10 microns. Combinations of the above-referenced ranges are also possible (e.g., in a range of 1 micron to 500 microns, 10 microns to 300 microns, 15 microns to 100 microns). Other ranges are also possible. In some embodiments, at least some of (e.g., all of) the wells of a bottomless array of wells (e.g., a bottomless microwell array), and/or at least some of (e.g., all of) the through-holes in a dry film of photoresist, have a largest lateral dimension (e.g., uniform diameter) in a range of 1 micron to 500 microns (e.g., 15 microns to 100 microns, 1 micron to 10 microns).

In some embodiments, at least some of (e.g., all of) the wells of a bottomless array of wells (e.g., a bottomless microwell array), and/or at least some of (e.g., all of) the through-holes in a dry film of photoresist, have a largest lateral dimension relative to the largest lateral dimension of a cell and/or well such that at most several beads and/or cells (e.g., a single bead and/or a single cell) would fit inside of a well and/or through-hole. In some embodiments, at least some of (e.g., all of) the wells of a bottomless array of wells (e.g., a bottomless microwell array), and/or at least some of (e.g., all of) the through-holes in a dry film of photoresist, have a largest lateral dimension of at least 1 time, at least 2 times, or at least 3 times the largest lateral dimension of a cell and/or bead. In some embodiments, at least some of (e.g., all of) the wells of a bottomless array of wells (e.g., a bottomless microwell array), and/or at least some of (e.g., all of) the through-holes in a dry film of photoresist, have a largest lateral dimension of at most 6 times, at least 5 times, or at most 4 times the largest lateral dimension of a cell and/or bead. Combinations of the above-referenced ranges are also possible (e.g., in a range of 1 to 6 times, 2 to 5 times, 3 to 4 times). Other ranges are also possible. In some embodiments, at least some of (e.g., all of) the wells of a bottomless array of wells (e.g., a bottomless microwell array), and/or at least some of (e.g., all of) the through-holes in a dry film of photoresist, have a largest lateral dimension in a range of 1 to 6 times the largest lateral dimension of a cell and/or bead. In some embodiments, at least some of (e.g., all of) the wells of a bottomless array of wells (e.g., a bottomless microwell array), and/or at least some of (e.g., all of) the through-holes in a dry film of photoresist, have a largest lateral dimension in a range of 1 to 6 times the largest lateral dimension of a cell. In some embodiments, at least some of (e.g., all of) the wells of a bottomless array of wells (e.g., a bottomless microwell array), and/or at least some of (e.g., all of) the through-holes in a dry film of photoresist, have a largest lateral dimension in a range of 1 to 6 times the largest lateral dimension of a bead.

In some embodiments, at least some of (e.g., all of) the wells in an array of wells, and/or at least some of (e.g., all of) the through-holes in a layer (e.g., dry film of photoresist) are cylindrical. In some embodiments, at least some of (e.g., all of) the wells in an array of wells, and/or at least some of (e.g., all of) the through-holes in a layer (e.g., dry film of photoresist) are cylindrical and have a uniform diameter. In some embodiments, at least some of (e.g., all of) the wells in an array of wells, and/or at least some of (e.g., all of) the through-holes in a layer (e.g., dry film of photoresist) are cylindrical and have a diameter of at least 1 micron, at least 10 microns, or at least 15 microns. In some embodiments, at least some of (e.g., all of) the wells in an array of wells, and/or at least some of (e.g., all of) the through-holes in a layer (e.g., dry film of photoresist) are cylindrical and have a diameter of at most 500 microns, at most 300 microns, at most 200 microns, at most 100 microns, or at most 10 microns. Combinations of the above-referenced ranges are also possible (e.g., in a range of 1 micron to 500 microns, 10 microns to 300 microns, 15 microns to 100 microns). Other ranges are also possible. In some embodiments, at least some of (e.g., all of) the wells in an array of wells, and/or at least some of (e.g., all of) the through-holes in a layer (e.g., dry film of photoresist) are cylindrical and have a diameter in the range of 1 microns to 500 microns (e.g., 15 microns to 100 microns or 1 micron to 10 microns).

In some embodiments, at least some of (e.g., all of) the wells in an array of wells (e.g., a bottomless microwell array), and/or at least some of (e.g., all of) the through-holes in a layer (e.g., dry film of photoresist) are in the shape of a rectangular prism (e.g., square prism, having a square cross-section). In some embodiments, at least some of (e.g., all of) the wells in an array of wells, and/or at least some of (e.g., all of) the through-holes in a layer (e.g., dry film of photoresist) are in the shape of a rectangular prism (e.g., square prism, having a square cross-section) and have a uniform largest lateral dimension. In some embodiments, at least some of (e.g., all of) the wells in an array of wells, and/or at least some of (e.g., all of) the through-holes in a layer (e.g., dry film of photoresist) are in the shape of a rectangular prism (e.g., square prism, having a square cross-section) and have a largest lateral dimension (e.g., diagonal of rectangular or square cross-section; e.g., uniform largest lateral dimension) in a range of 1 micron to 500 microns (e.g., 15 microns to 100 microns or 1 micron to 10 microns).

In some embodiments, at least some of (e.g., all of) the wells in an array of wells, and/or at least some of (e.g., all of) the through-holes in a layer (e.g., dry film of photoresist) are pyramidal (in the shape of a pyramid; e.g., rectangular pyramidal, square pyramidal, triangular pyramidal, etc.). In some embodiments, at least some of (e.g., all of) the wells in an array of wells, and/or at least some of (e.g., all of) the through-holes in a layer (e.g., dry film of photoresist) array are pyramidal and have a uniform largest lateral dimension. In some embodiments, at least some of (e.g., all of) the wells in an array of wells, and/or at least some of (e.g., all of) the through-holes in a layer (e.g., dry film of photoresist) array are pyramidal and have a largest lateral dimension (e.g., diagonal of a largest cross-section; e.g., uniform largest lateral dimension) in a range of 35 microns to 100 microns (e.g., 45 microns to 80 microns, 40 microns to 50 microns) at the top surface of the layer or array (e.g., bottomless microwell array), and have a largest lateral dimension in a range of 0.5 microns to 10 microns (e.g., 0.5 microns to 3 microns, 1 micron to 5 microns) at the bottom surface of the layer or array (e.g., bottomless microwell array). Other ranges are also possible.

In some embodiments, at least some of (e.g., all of) the wells in an array of wells, and/or at least some of (e.g., all of) the through-holes in a layer (e.g., dry film of photoresist) are conical. In some embodiments, at least some of (e.g., all of) the wells in an array of wells, and/or through-holes in a layer (e.g., dry film of photoresist) array are conical and have a uniform diameter. In some embodiments, at least some of (e.g., all of) the wells in an array of wells, and/or at least some of (e.g., all of) the through-holes in a layer (e.g., dry film of photoresist) array are conical and have a diameter (e.g., uniform diameter) in a range of 35 microns to 100 microns (e.g., 45 microns to 80 microns, 40 microns to 50 microns) at the top surface of the layer or array (e.g., bottomless microwell array), and have a diameter in a range of 0.5 microns to 10 microns (e.g., 0.5 microns to 3 microns, 1 micron to 5 microns) at the bottom surface of the layer or array (e.g., bottomless microwell array). Other ranges are also possible.

As used herein, the characterizing term "uniform" in referencing a quantity (e.g., a distance, a thickness, a dimension (e.g., a largest lateral dimension)) refers to a variation in that quantity by no more than 10% more or less than the stated value or an average of that quantity (e.g., no more than 5% more or less, no more than 1% more or less, no more than 0.1% more or less than the stated value or an average of that quantity).

In some embodiments, at least some of (e.g., all of) the wells in an array of wells, and/or at least some of (e.g., all of) the through-holes in a layer (e.g., dry film of photoresist), have a pitch low enough so as to reduce or minimize the device area required for analyzing a large quantity of cells and/or beads, with a single cell and/or bead per well or through-hole, while providing adequate separation between each well or through-hole. In some embodiments, the pitch of through-holes in a layer of dry film of photoresist is low enough so that a photomask bound to the dry film of photoresist could be removed in developing solution, while providing adequate separation between each well or through-hole.

As used herein, the term "pitch" between features (e.g., wells in an array of wells, features on a photomask) in a layer refers to a center-to-center distance between features in the layer in a plane (e.g., any plane, a specific plane) parallel to the plane of a layer (e.g., bottomless array of wells) on which and/or in which the feature is located.

In some embodiments, at least some of (e.g., all of) the wells in an array of wells, and/or at least some of (e.g., all of) the through-holes in a layer (e.g., dry film of photoresist), have a maximum pitch of 2 mm. In some embodiments, at least some of (e.g., all of) the wells in an array of wells (e.g., bottomless microwell array), and/or at least some of (e.g., all of) the through-holes in a layer (e.g., dry film of photoresist), have a pitch of at least 1 micron, at least 10 microns, at least 20 microns, or at least 50 microns. In some embodiments, at least some of (e.g., all of) the wells in an array of wells (e.g., bottomless microwell array), and/or at least some of (e.g., all of) the through-holes in a layer (e.g., dry film of photoresist), have a pitch of at most 2 mm, at most 1 mm, at most 500 microns, or at most 200 microns. Combinations of the above-referenced ranges are also possible (e.g., in a range of 1 micron to 2 mm, 10 microns to 1 mm, 20 microns to 500 microns). Other ranges are also possible. In some embodiments, at least some of (e.g., all of) the wells in an array of wells (e.g., bottomless microwell array), and/or at least some of (e.g., all of) the through-holes in a layer (e.g., dry film of photoresist), have a pitch in a range of 20 microns to 200 microns (e.g., 10 microns to 200 microns).

In some embodiments, the through-holes in a layer of dry film of photoresist occupy an area percentage of the dry film of photoresist, on the surface facing a photomask, large enough so that a photomask bound to the dry film of photoresist could be removed in developing solution. In some embodiments, a total lateral area of wells at a top surface of a dry film of photoresist (e.g., the surface contacting a photomask) is at least 10% of the total lateral area of the dry film of photoresist. In some embodiments, a total lateral area of wells at a top surface of a dry film of photoresist is at least 10%, at least 20%, at least 30%, at least 40%, or at least 50% of the total lateral area of the dry film of photoresist. In some embodiments, a total lateral area of wells at a top surface of a dry film of photoresist is at most 99.9%, at most 99%, at most 90%, at most 80%, at most 70%, or at most 60% of the total lateral area of the dry film of photoresist. Combinations of the above-referenced ranges are also possible (e.g., in a range of 10% to 99.9%, 20% to 90%, 30% to 80%). Other ranges are also possible.

As used herein, the term "total lateral area" of a collection of features (e.g., of wells) in a layer refers to the cumulative cross-sectional area of all of the features (e.g., wells) in a plane (e.g., any plane, a specific plane) parallel to the plane of a layer (e.g., bottomless array of wells) on which and/or in which the features are located.

In some embodiments, the wells represent at least about 10% of the surface area of the top surface of the dry film of photoresist (e.g., the surface contacting a photomask). In some embodiments, the wells represent at least 10%, at least 20%, at least 30%, at least 40%, or at least 50% of the surface area of the top surface of the dry film of photoresist. In some embodiments, the wells represent at most 99.9%, at most 99%, at most 90%, at most 80%, at most 70%, or at most 60% of the surface area of the top surface of the dry film of photoresist. Combinations of the above-referenced ranges are also possible (e.g., in a range of 10% to 99.9%, 20% to 90%, 30% to 80%). Other ranges are also possible.

A First Bottomless Microwell Array

In some embodiments, a layered device (e.g., microfluidic device, array of wells, e.g., comprising a dry film of photoresist) comprises a dry film of photoresist, e.g., comprising a plurality of through-holes or wells (e.g., bottomless array of wells, bottomless microwell array).

As used herein, the term "photoresist" will be known to those of ordinary skill in the art and refers to a material sensitive to certain electromagnetic radiation (e.g., ultraviolet (UV) light) used in methods of forming a pattern onto a surface of the material and/or through the material. In some embodiments, a dry film of photoresist is a negative photoresist. The term "negative photoresist" will be known to those of ordinary skill in the art and refers to a photoresist in which portions exposed to certain electromagnetic radiation (e.g., UV light) become crosslinked, while portions not exposed remain soluble in developing solution and can be removed during development. In some embodiments, a dry film of photoresist comprises a negative photoresist material comprising an epoxide group. An epoxide group refers to a cyclic ether with a three-membered ring, optionally comprising any of a variety of substituents bonded with the two carbons in the three-membered ring. In some embodiments, a negative photoresist forms an acid during exposure to certain electromagnetic radiation (e.g., UV light), which acid induces polymerization of the negative photoresist material. In some embodiments the dry film of photoresist comprises SU-8 photoresist, a common photoresist comprising 8 epoxide groups with the chemical structure of the epoxide groups in SU-8 being:

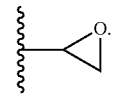 [SMILES: *C1CO1]

In some embodiments, the dry film of photoresist comprises a commercially available dry film of photoresist (e.g., dry film of negative photoresist). While epoxide photoresist chemistries are referred to as examples, it should be understood that other photoresist chemistries are also possible.

In some embodiments, a dry film of photoresist (e.g., comprising a plurality of through-holes; e.g., a bottomless microwell array) is situated over (e.g., is positioned adjacent to, contacts, directly contacts, is adhered to, is bonded to) a porous membrane. In some embodiments, a dry film of photoresist is directly contacted to a porous membrane. In certain embodiments, a dry film of photoresist (e.g., comprising a plurality of through-holes; e.g., a bottomless microwell array) is bonded to a porous membrane. In some embodiments, a dry film of photoresist is bonded (e.g., by heat lamination) to a porous membrane.

As used herein, the term "contact" referring to two articles (e.g., two layers, e.g., a bottomless array and a base layer) means to physically touch any portions of the two articles together that are available to touch. For example, in a layered configuration of two articles (e.g., layers), a top surface of a first article may contact a bottom surface of a second article.

As used herein, the term "bonded" refers to a state of attachment of one layer to another (e.g., by adhesive, by lamination, e.g., by heat lamination).

In some embodiments, the first bottomless microwell array comprises a first porous membrane. In some embodiments, a first porous membrane has a pore size (e.g., an average pore size) large enough to accommodate flow of a liquid through the porous membrane at high throughput, but small enough to prevent cells and/or beads from passing through the porous membrane. In some embodiments, a porous membrane has a pore size (e.g., an average pore size)

of at least 1 nm, at least 10 nm, at least 50 nm, at least 80 nm, at least 100 nm, at least 200 nm, at least 300 nm, or at least 500 nm. In some embodiments, a porous membrane has a pore size (e.g., an average pore size) of at most 3 microns, at most 2 microns, or at least 1 micron. Combinations of the above-referenced ranges are also possible (e.g., in a range of 5 nm to 3 microns, 1 nm to 1 micron, 80 nm to 200 nm). Other ranges are also possible. In some embodiments, a porous membrane has a pore size (e.g., an average pore size) in a range of 50 nm to 3 microns. In some embodiments, a porous membrane has an average pore size (e.g., diameter) in a range of 1 nm to 1000 nm (e.g., 80 nm to 200 nm).

In some embodiments, a porous membrane has a pore size (e.g., an average pore size) that is a low enough multiple of a largest lateral dimension of a cell and/or bead such that cells and/or beads cannot pass through the porous membrane. In some embodiments, a porous membrane has an average pore size of at least 0.001 times, at least 0.01 times, or at least 0.1 times a largest lateral dimension of a cell and/or bead. In some embodiments, a porous membrane has an average pore size of at most 0.25 times, at most 0.2 times, or at most 0.15 times a largest lateral dimension of a cell and/or bead. Combinations of the above-referenced ranges are also possible (e.g., in a range of 0.001 times to 0.25 times, 0.01 times to 0.2 times, 0.1 times to 0.15 times). Other ranges are also possible. In some embodiments, a porous membrane has an average pore size in a range of 0.001 to 0.25 times (e.g., 0.001 to 0.1 times) a largest lateral dimension of a cell and/or bead. In some embodiments, a porous membrane has an average pore size in a range of 0.001 to 0.1 times a largest lateral dimension of a cell. In some embodiments, a porous membrane has an average pore size in a range of 0.001 to 0.1 times a largest lateral dimension of a bead.

In some embodiments, a porous membrane has a flux rate high enough to accommodate flow of a liquid through the porous membrane at high throughput. In some embodiments, a porous membrane has a flux rate of at least 0.1 mL/min/cm², at least 0.5 mL/min/cm², or at least 1 mL/min/cm². In some embodiments, a porous membrane has a flux rate of at most 100 mL/min/cm², at most 10 mL/min/cm², or at most 5 mL/min/cm². Combinations of the above-referenced ranges are also possible (e.g., in a range of 0.1 mL/min/cm² to 100 mL/min/cm², 0.5 mL/min/cm² to 10 mL/min/cm², 1 mL/min/cm² to 5 mL/min/cm²). Other ranges are also possible. In some embodiments, a porous membrane has a flux rate in a range of 0.1 mL/min/cm² to 100 mL/min/cm².

In some embodiments, a porous membrane is of sufficient thickness to provide mechanical integrity such that neither cells nor beads pass through but not so high as to reduce flux of liquid through the membrane below a desired value. In some embodiments, a porous membrane has a thickness of at least 5 microns, at least 10 microns, or at least 20 microns. In some embodiments, a porous membrane has a thickness of at most 500 microns, at most 200 microns, or at most 100 microns. Combinations of the above-referenced ranges are also possible (e.g., in a range of 5 microns to 500 microns, 10 microns to 200 microns, 20 microns to 100 microns). Other ranges are also possible. In some embodiments, a porous membrane has a thickness in a range of 5 microns to 500 microns. In some embodiments, a porous membrane has a thickness of 10 microns.

In some embodiments, a porous membrane is situated under (e.g., is positioned adjacent to, contacts, directly contacts, is adhered to, is bonded to) a dry film of photoresist comprising a plurality of through-holes, e.g., a bottomless microwell array, e.g., at a bottom surface of the second layer.

As used herein, the term "adjacent" referring to two articles (e.g., two layers, e.g., a bottomless array and a base layer) that are positioned near one another and may or may not be contacting one another (e.g., may have an intervening layer in between).

In some embodiments, a dry film of photoresist has a plurality of through-holes. In some embodiments, a dry film of photoresist comprising a plurality of through-holes forms a bottomless array of wells (e.g., a bottomless microwell array).

In some embodiments, a dry film of photoresist has a uniform thickness.

In some embodiments, a dry film of photoresist has a thickness such that at most several beads and/or cells (e.g., a single bead and/or a single cell) would fit inside of a well and/or through-hole in the dry film of photoresist. In some embodiments, a dry film of photoresist has a thickness of at least 5 microns, at least 10 microns, or at least 20 microns. In some embodiments, a dry film of photoresist has a thickness of at most 500 microns, at most 200 microns, or at most 100 microns. Combinations of the above-referenced ranges are also possible (e.g., in a range of 5 microns to 500 microns, 10 microns to 200 microns, 20 microns to 100 microns). Other ranges are also possible. In some embodiments, a dry film of photoresist has a thickness in a range of 5 microns to 500 microns. In some embodiments, a dry film of photoresist has a thickness in a range of 5 microns to 100 microns. In some embodiments, a dry film of photoresist has a thickness of 50 microns.

Top Membrane

In some embodiments, a layered device (e.g., microfluidic device, array of wells, e.g., comprising a dry film of photoresist) further comprises a second porous membrane. In some embodiments, the second porous membrane is for sealing the wells of the layered device. As used herein, the term "ultrafiltration membrane" refers to a semipermeable membrane that has a pore size (e.g., average pore size) small enough to exclude high molecular weight molecules (e.g., DNA) from passing through. In some embodiments, an ultrafiltration membrane has a molecular weight cut-off of less than or equal to $10^6$ Da (e.g., between or equal to $10^3$ and $10^6$ Da, between or equal to $10^3$ and $3*10^5$ Da). The term "molecular weight cut-off" will be known to those of skill in the art and refers to the lowest molecular weight of a molecule in which at least 90% of the molecule is prevented from passing through the membrane. In some embodiments, an ultrafiltration membrane comprises a polymer (e.g., polysulfone, polypropylene, cellulose acetate, polylactic acid) and/or a ceramic.

In some embodiments, a second porous membrane (e.g., an ultrafiltration membrane) has an average pore size (e.g., diameter) small enough to exclude cells and at least some cell contents (e.g., high molecular weight molecules, e.g., DNA) from passing through. In some embodiments, a second porous membrane has an average pore size in a range described herein (e.g., in a range of 1 nm to 200 nm).

In some embodiments, a second porous membrane is located in a layered device relative to other components (e.g., layers) of the layered device. For example, in some embodiments, a second porous membrane is situated over a layer (e.g., dry film of photoresist), e.g., contacts a layer (e.g., dry film of photoresist) at a top surface of the layer (e.g., dry film of photoresist). In some embodiments, a second porous membrane is situated over or under a second layer. For example, in some embodiments, a second porous membrane contacts a top surface or bottom surface of a second layer (e.g., dry film of photoresist, bottomless microwell array). In some embodiments, a second porous membrane is situated over a second bottomless microwell array. In some embodiments, a second porous membrane is directly contacted to a second bottomless microwell array.

A Second Bottomless Microwell Array

In some embodiments, a layered device (e.g., microfluidic device, array of wells, e.g., comprising a dry film of photoresist) comprises a second dry film of photoresist, e.g., comprising a plurality of through-holes (e.g., bottomless array of wells, bottomless microwell array).

In some embodiments, a second dry film of photoresist (e.g., a second bottomless microwell array) is situated over (e.g., adjacent to, contacting, bonded to) a first dry film of photoresist (e.g., a first bottomless microwell array). In some embodiments, a second dry film of photoresist (e.g., a second bottomless microwell array) is directly contacted to a first dry film of photoresist (e.g., a first bottomless microwell array). In some embodiments, a second dry film of photoresist (e.g., a second bottomless microwell array) is bonded to a third porous membrane. In some embodiments, a second bottomless microwell array comprises a second dry film of photoresist. In some embodiments, a second dry film of photoresist is over (e.g., with a porous membrane in between, or with more layers in between, or directly adjacent to and/or contacting) a first dry film of photoresist and has a second plurality of through-holes.

In some embodiments, a layered device comprises at least two dry films of photoresist comprising through-holes (e.g., bottomless arrays of wells, e.g., bottomless microwell array) in a layered configuration, situated over one another (e.g., contacting or bonded to one another; e.g., with a porous membrane in between). In some embodiments, each of at least 70%, at least 80%, or at least 90% of the through-holes (e.g., wells) of a first bottomless array of wells is in fluid communication with a respective single through-hole (e.g., well) of a first bottomless array of wells. In some embodiments, each of at most 100%, at most 95%, or at most 85% of the through-holes (e.g., wells) of a first bottomless array of wells is in fluid communication with a respective single through-hole (e.g., well) of a first bottomless array of wells. Combinations of the above-referenced ranges are also possible (e.g., in a range of 70% to 100%, 80% to 95%, 80% to 85%). Other ranges are also possible. In some embodiments, each of at least 90% of the through-holes (e.g., wells) of a first bottomless array of wells is in fluid communication with a respective single through-hole (e.g., well) of a first bottomless array of wells.

In some embodiments, a largest lateral dimension of through-holes in the first bottomless array of wells is smaller than a largest lateral dimension of through-holes in the second bottomless array of wells. In some embodiments, largest lateral dimension of through-holes in the first bottomless array of wells is 1-10 microns and largest lateral dimension of through-holes in the second bottomless array of wells is 15-100 microns. In some embodiments, a largest lateral dimension of through-holes in the first bottomless array of wells is larger than a largest lateral dimension of through-holes in the second bottomless array of wells. In some embodiments, largest lateral dimension of through-holes in the first bottomless array of wells is 15-100 microns and largest lateral dimension of through-holes in the second bottomless array of wells is 1-10 microns.

In some embodiments, a layered device (e.g., microfluidic device, array of wells, e.g., comprising a dry film of photoresist) comprises a third porous membrane. In some embodiments, a third porous membrane is situated under a second dry film of photoresist (e.g., comprising through-holes; e.g., bottomless microwell array), and/or is situated over a first dry film of photoresist (e.g., comprising through-holes; e.g., bottomless microwell array). In some embodiments, a third porous membrane directly contacted to a first and/or second dry film of photoresist (e.g., comprising through-holes; e.g., bottomless microwell array). In some embodiments, a third porous membrane is situated between a first dry film of photoresist (e.g., comprising through-holes; e.g., bottomless microwell array) and a second dry film of photoresist (e.g., comprising through-holes; e.g., bottomless microwell array). In some embodiments, the third porous membrane has any of the properties of the first porous membrane described herein.

In some embodiments, the wells of the layered device further comprise beads and/or cells, as are described herein.

Several non-limiting embodiments of the layered devices (e.g., microfluidic device, array of wells, e.g., comprising a dry film of photoresist) are described in further detail. However, it should be understood that the current disclosure is not limited to only those specific embodiments described herein. Instead, the various disclosed components, articles, features, and methods may be arranged in any suitable combination as the disclosure is not so limited.

In some embodiments, a layered device comprises a base layer (e.g., a porous membrane) attached to a dry film of photoresist comprising a plurality of through-holes that are cylindrical or rectangular prismatic (e.g., square prismatic) in shape, with a circular or rectangular cross-section respectively. This configuration is shown in FIGS. 10A and 10D.

Figure 10A:
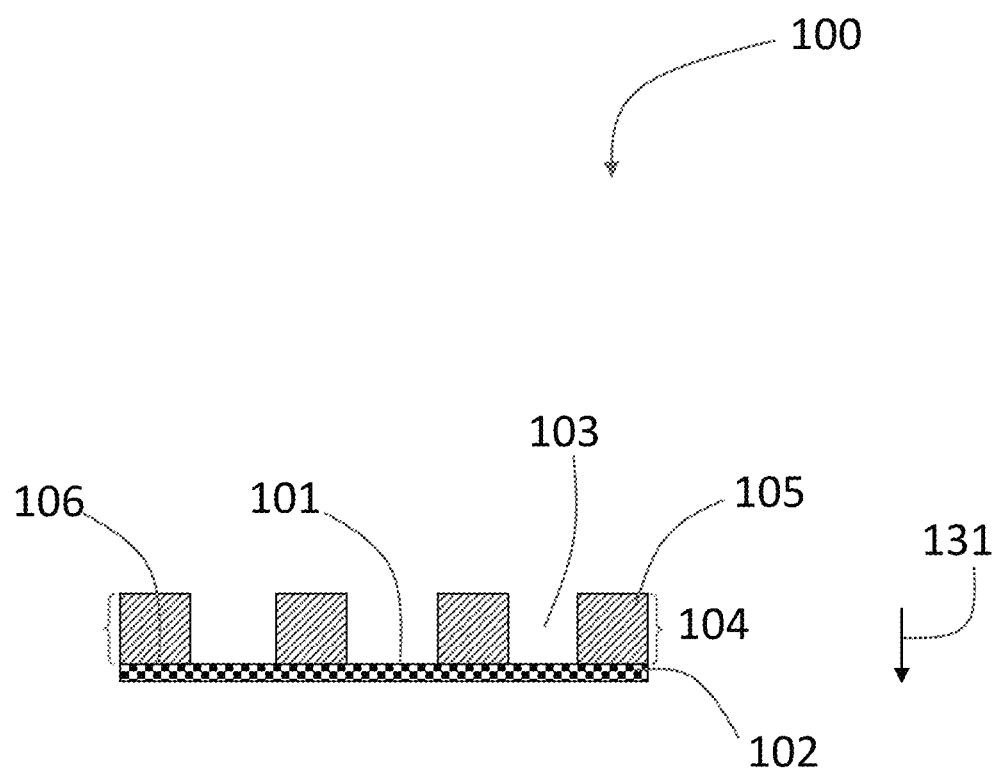
FIGS. 10A-10E are schematic diagrams of the layered devices described herein.

FIG. 10A is a cross-sectional schematic diagram of an array 100 of wells, according to certain non-limiting embodiments. The depicted array 100 of wells includes a first layer 102 (e.g., a porous membrane). In some embodiments, the first layer 102 is a porous membrane and has a flux rate in a range of 0.1 mL/min/cm$^2$ to 100 mL/min/cm$^2$ and/or a pore size in a range of 50 nm to 3 microns. The depicted array 100 of wells also includes a first bottomless array of wells 104 (e.g., bottomless microwell array) comprising a first dry film of photoresist 105 having a first plurality of through-holes 103. The first layer 102 contacts (e.g., is positioned adjacent to, directly contacts, is adhered to, is bonded to) the first bottomless array of wells 104 at the bottom surface 106 of the first bottomless array of wells 104. Each well of the array 100 comprises one of the first plurality of through-holes 103 and a bottom surface 101 comprising the first layer 102. While three wells are depicted, and the wells are depicted as having walls normal to the plane of the dry film of photoresist, it should be understood that an array may comprise any suitable number of wells (e.g., 1, 10, 100, 1000, or more wells) in one or two dimensions and/or may comprise wells of any suitable shape (e.g., cylindrical, rectangular prismatic, square prismatic, conical, or pyramidal shape) and/or size (e.g., largest lateral dimension); see, e.g., FIG. 10C. Other ranges are also possible. Array 100 may be used for the super-Poisson loading of cells and/or beads, e.g., by flowing a liquid comprising cells and/or beads through array 100 in flow direction 131.

Figure 10B:
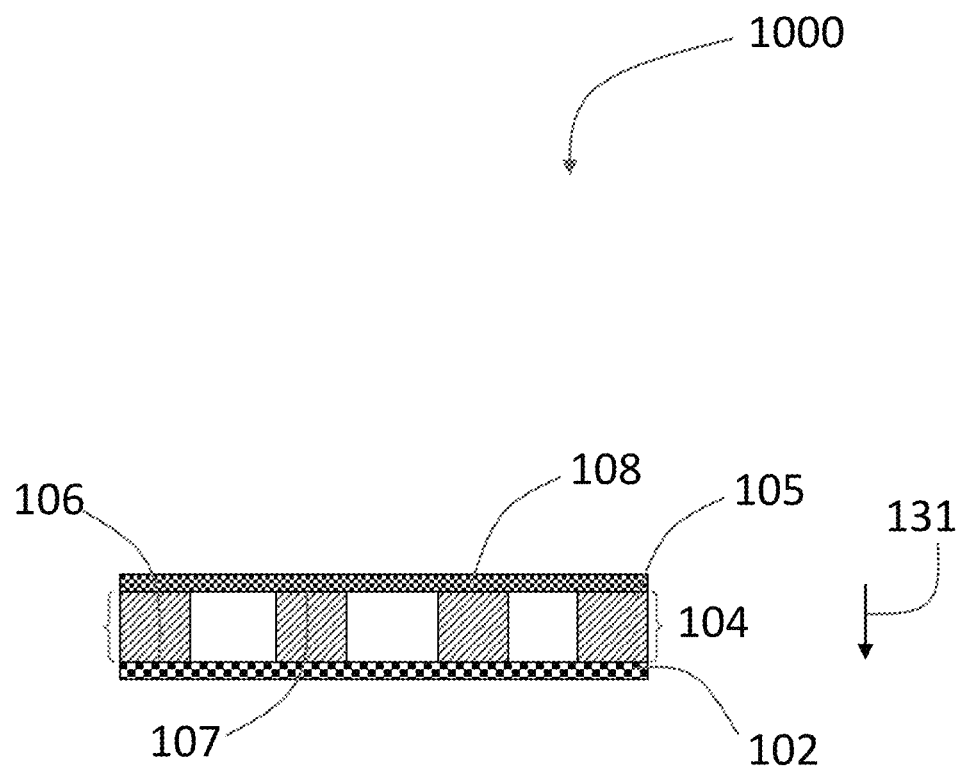
Figure 10C:
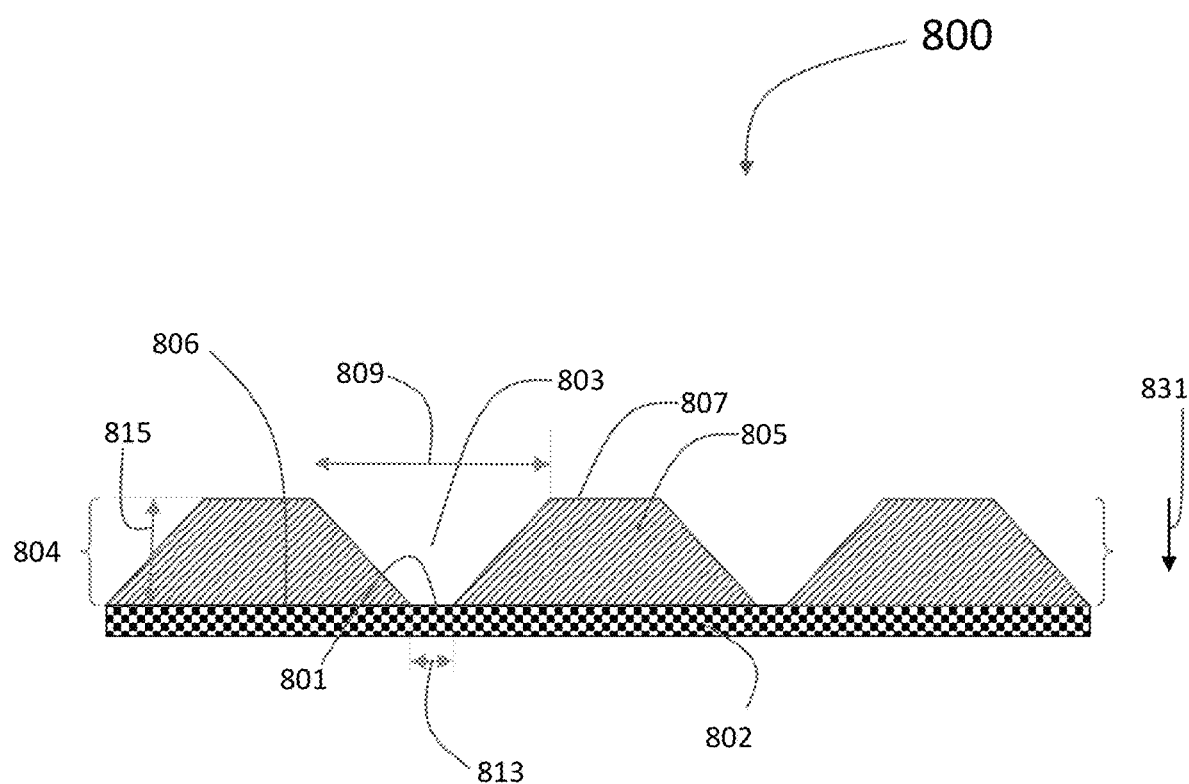
Figure 10D:
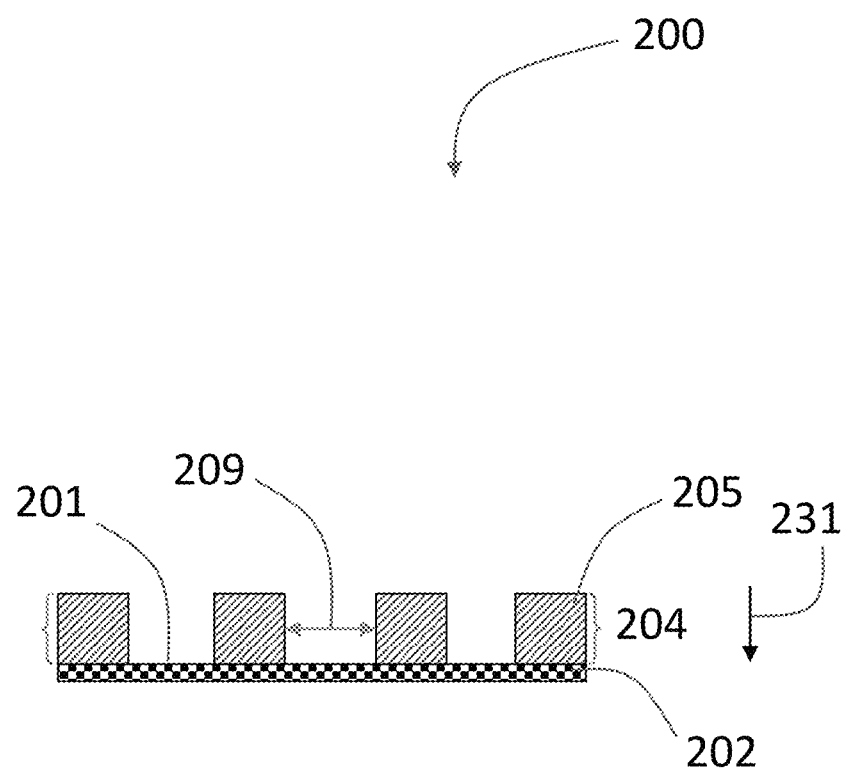

FIG. 10D is a cross-sectional schematic diagram of a layered device 200, according to certain non-limiting embodiments. The depicted layered device 200 includes a dry film of photoresist 205 comprising an array 204 of wells. In some embodiments, wells in the array 204 of wells have a largest lateral dimension 209 in the range of 15 microns to 100 microns. Wells in the array 204 have a bottom 201 (e.g., porous bottom). Bottom 201 (e.g., porous bottom) comprises layer 202 (e.g., porous membrane). In some embodiments, bottom 201 (e.g., porous bottom) and/or layer 202 (e.g., porous membrane) is porous and has a flux rate in a range of 0.1 mL/min/cm$^2$ to 100 mL/min/cm$^2$ and/or a pore size in a range of 50 nm and 3 microns. It should be understood that an array may comprise any suitable number of wells (e.g., 1, 10, 100, 1000, or more wells) in one or two dimensions and/or may comprise wells of any suitable shape (e.g., cylindrical, rectangular prismatic, square prismatic, conical, or pyramidal shape) and/or size (e.g., largest lateral dimension). Other ranges are also possible. Array 200 may be used for the super-Poisson loading of cells and/or beads, e.g., by flowing a liquid comprising cells and/or beads through array 200 in flow direction 231.

In some embodiments, a layered device comprises a dry film of photoresist comprising a plurality of through-holes that are cylindrical or rectangular prismatic (e.g., square prismatic) in shape, with a circular or rectangular cross-section respectively, which dry film of photoresist is attached on a bottom surface to a base layer (e.g., a porous membrane) and attached at a top surface to a second layer (e.g., an ultrafiltration membrane). This configuration is shown in FIG. 10B.

FIG. 10B is a cross-sectional schematic diagram of an array 1000 of wells, according to certain non-limiting embodiments. The depicted array 1000 includes features of array 100 and further comprises a second layer 108 (e.g., porous membrane) that contacts the first dry film of photoresist 105 at top surface 107 of the first dry film of photoresist 105. The second layer 108 (e.g., porous membrane) may have the same average pore size or a different average pore size from that of the first layer 102. Second porous membrane 108 may be positioned onto the array 1000, e.g., by applying vacuum in flow direction 131.

In some embodiments, a layered device comprises a base layer (e.g., a porous membrane) attached to a dry film of photoresist comprising a plurality of through-holes that are conical or pyramidal in shape. This is shown in FIG. 10C.

FIG. 10C is a cross-sectional schematic diagram of an array 800 of wells, according to certain non-limiting embodiments. The depicted array 800 of wells includes a first layer 802 (e.g., porous membrane). In some embodiments, the first layer 802 (e.g., porous membrane) has a flux rate in a range of 0.1 mL/min/cm$^2$ to 100 mL/min/cm$^2$ and/or a pore size in a range of 50 nm to 3 microns. The depicted array 800 of wells also includes a first bottomless array of wells 804 comprising a first dry film of photoresist 805 having a first plurality of through-holes 803. The first layer 802 (e.g., porous membrane) contacts (e.g., is positioned adjacent to, directly contacts, is adhered to) the first bottomless array of wells 804 at the bottom surface 806 of the first bottomless array of wells 804. Each well of the array 800 comprises one of the first plurality of through-holes 803 and a bottom surface 801 comprising the first layer 802 (e.g., porous membrane). While two wells are depicted, it should be understood that an array may comprise any suitable number of wells (e.g., 1, 10, 100, 1000, or more wells) in one or two dimensions. The depicted wells have a tapering cross-section (due to, e.g., a conical shape or a pyramidal shape) such that each well has a largest cross-sectional dimension 809 at the top surface 807 of the dry film of photoresist 805 and a smallest cross-sectional dimension 813 at the bottom surface 806 of the dry film of photoresist 805. In some embodiments, the wells have a largest cross-sectional dimension 809 in the range of 35 microns to 100 microns at the top surface 807 of the dry film of photoresist 805. In some embodiments, the wells have a smallest cross-sectional dimension 813 in the range of 0.5 microns to 3 microns at the bottom surface 806 of the dry film of photoresist 805. In some embodiments, the dry film of photoresist 805 has a thickness 815 of between or equal to 30 microns and 100 microns. Other ranges are also possible. Array 800 may be used for the super-Poisson loading of cells and/or beads, e.g., by flowing a liquid comprising cells and/or beads through array 800 in flow direction 831. In some embodiments, array 800 is used for the super-Poisson loading of cells (as described herein) first and then beads (as described herein) second, e.g., by flowing a liquid comprising cells through array 800 in flow direction 831 and then exposing the array 800 to a liquid comprising beads (e.g., allowing beads to settle into the array, flowing a liquid comprising beads through array 800 in flow direction 831).

In some embodiments, a layered device comprises a first dry film of photoresist comprising a plurality of through-holes that are cylindrical or rectangular prismatic (e.g., square prismatic) in shape, with a circular or rectangular cross-section respectively, which first dry film of photoresist is attached on a bottom surface to a base layer (e.g., a porous membrane) and attached at a top surface to a second dry film of photoresist, wherein the second dry film of photoresist comprises a plurality of through-holes that are cylindrical or rectangular prismatic (e.g., square prismatic) in shape, with a circular or rectangular cross-section respectively, wherein no more than one through-hole in the first dry film of photoresist overlaps with no more than one through-hole in the second dry film of photoresist, and wherein between or equal to 70% and 100% (e.g., between or equal to 70% and 85%) of through-holes in the first dry film of photoresist overlap with a respective through-hole in the second dry film of photoresist. This is shown in FIG. 10E.

Figure 10E:
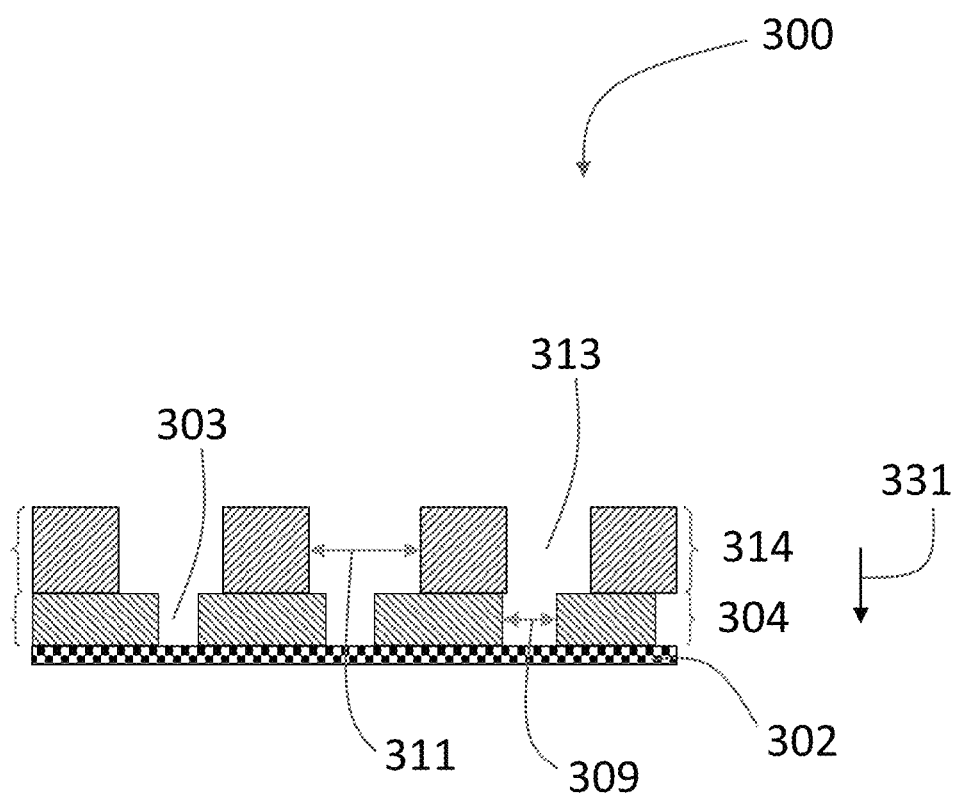

FIG. 10E is a cross-sectional schematic diagram of a layered device 300 (e.g., a microfluidic device), according to certain non-limiting embodiments. Depicted layered device 300 includes a first bottomless array of wells 304 comprising a first plurality of through-holes 303. In some embodiments, first plurality of through-holes 303 have a largest lateral dimension (e.g., 309) in the range of 1 micron to 500 microns. First bottomless array of wells 304 is contacting (e.g., bonded to) second bottomless array of wells 314 comprising a second plurality of through-holes 313. In some embodiments, second plurality of through-holes 313 have a largest lateral dimension (e.g., 311) in the range of 1 micron to 500 microns. First bottomless array of wells 304 is also contacting (e.g., bonded to) a first layer 302 (e.g., porous membrane). It should be understood that an array may comprise any suitable number of wells (e.g., 1, 10, 100, 1000, or more wells) in one or two dimensions and/or may comprise wells of any suitable shape (e.g., cylindrical, rectangular prismatic, square prismatic, conical, or pyramidal shape) and/or size (e.g., largest lateral dimension). Other ranges are also possible. Array 300 may be used for the super-Poisson loading of cells and/or beads, e.g., by flowing a liquid comprising cells and/or beads through array 300 in flow direction 331. In some embodiments, array 300 is used for the super-Poisson loading of cells (as described herein) first and then beads (as described herein) second using methods similar to that in array 800 in FIG. 10C, e.g., by flowing a liquid comprising cells through array 300 in flow direction 331 and then exposing the array 300 to a liquid comprising beads (e.g., allowing beads to settle into the array, flowing a liquid comprising beads through array 300 in flow direction 331). In some embodiments, a layered device further comprises a porous membrane between bottomless array of wells 304 and bottomless array of wells 314, and/or a porous membrane situated on top of bottomless array of wells 314.

In some embodiments, a layered device comprises a first dry film of photoresist comprising a plurality of through-holes that are cylindrical or rectangular prismatic (e.g., square prismatic) in shape, with a circular or rectangular cross-section respectively, which first dry film of photoresist is attached on a bottom surface to a base layer (e.g., a porous membrane) and attached at a top surface to a porous membrane, the top surface of which porous membrane is attached to a second dry film of photoresist, wherein the second dry film of photoresist comprises a plurality of through-holes that are cylindrical or rectangular prismatic (e.g., square prismatic) in shape, with a circular or rectangular cross-section respectively, wherein no more than one through-hole in the first dry film of photoresist overlaps with no more than one through-hole in the second dry film of photoresist, wherein between or equal to 70% and 100% (e.g., between or equal to 70% and 85%) of through-holes in the first dry film of photoresist overlap with a respective through-hole in the second dry film of photoresist, and wherein at least 70% (e.g., at least 80%, in a range of 80% and 85%) of the through-holes in the first dry film of photoresist are each occupied by a single bead.

It should be appreciated that the characterizing terms "first", and "second" features and/or layers (e.g., bottomless microwell array, plurality of through-holes), as used herein, refer to different features and/or layers within the layered device, and are not meant to be limiting with respect to the location of that feature and/or layer. Furthermore, in some embodiments, additional features and/or layers (e.g., "third", "fourth", "fifth", "sixth", or "seventh" features) may be present in addition to the ones shown in the figures. It should also be appreciated that not all features and/or layers shown in the figures need be present in some embodiments.

As used herein, the descriptors "over" and "under" refer to a layered configuration, and are not orientation-specific, but may be over or under depending on the angle at which an array is held. "Over" or "under" imply layering but not necessarily direct contact; there may be one or more intervening layers.

Methods of Manufacture

Methods of making a free standing photoresist film, e.g., a layered device (e.g., microfluidic device, array of wells, e.g., comprising a dry film of photoresist), as described herein, are provided.

As is used herein, a "free standing photoresist film" comprises any dry film of photoresist, as is described herein comprising through-holes, wherein the through-holes are generated by exposing the dry film of photoresist to UV light without the dry film of photoresist being attached to a solid support other than a photomask.

In some embodiments, a method involves aligning a dry film of photoresist with a photomask.

As used herein, the term "align" for two layers (e.g., a photoresist and a photomask) means to arrange the two layers in a layered configuration, and such that the plane of each of the two layers are parallel to one another. In some embodiments, two aligned layers have space and/or one or more intervening layers between the two layers. In some embodiments, two aligned layers are contacting one another.

In some embodiments, the dry film of photoresist is not supported by a substrate during device fabrication.

In some embodiments, the method comprises laminating a surface of a dry film of photoresist directly to a photomask, optionally without an underlying support. In some embodiments, the method comprises removing a release-liner (e.g., a polyolefin release-liner) from a surface of a dry film of photoresist. In some embodiments, the method comprises removing the release-liner immediately prior to lamination. In some embodiments, laminating the surface of a dry film of photoresist directly to a photomask involves contacting the surface of the dry film of photoresist with a surface of the photomask; and exposing the dry film of photoresist and the photomask to a temperature in a range of 60 degrees Celsius to 80 degrees Celsius (e.g., between or equal to 60 and 70 degrees Celsius, 65 degrees Celsius) for a duration sufficient to bond the surface of the dry film of photoresist to the surface of the photomask. Other temperature ranges are also possible.

In some embodiments, laminating the surface of a dry film of photoresist directly to a photomask involves heat-laminating the dry film of photoresist directly to the photomask at a rate in a range of 0.1 m/min to 0.5 m/min (e.g., 0.2 m/min to 0.4 m/min; 0.3048 m/min=1 ft/min). Other exposure rate ranges are also possible.

In some embodiments, the method comprises exposing the at least one portion of a dry film of photoresist to ultraviolet (UV) light through a photomask for a period of time in a range of 1 min to 10 min (e.g., 2 min to 8 min, 2 min to 3 min, 2.5 min). Other durations are also possible.

In some embodiments, exposing the at least one portion of a dry film of photoresist to UV light through a photomask comprises directing UV light at an angle in a range of 0 degrees to 45 degrees from a direction normal to a surface of the dry film of photoresist such that wells (e.g., microwells) of a bottomless array of wells formed in the dry film of photoresist are conical in shape. In some such embodiments, exposing the at least one portion of a dry film of photoresist to UV light through a photomask comprises spinning the photomask and dry film of photoresist during exposure on an axis perpendicular to the plane of the photomask and the dry film of photoresist.

In some embodiments, exposing the at least one portion of a dry film of photoresist to UV light through a photomask comprises placing a diffuser in a light path (e.g., a UV light path) immediately before the photomask, wherein the light path originates on the opposite side of the photomask from the dry film of photoresist, thereby directing UV light at an angle in a range of 0 degrees to 45 degrees from a direction normal to a surface of the dry film of photoresist such that wells (e.g., microwells) of a bottomless array of wells formed in the dry film of photoresist are conical in shape.

In some embodiments, wells (e.g., microwells) of a bottomless array of wells that are conical in shape are formed in a dry film of photoresist by reactive ion etching or a UV backside exposure photolithography technique.

In some embodiments, after exposing the dry film of photoresist attached to the photomask to electromagnetic radiation (e.g., light), (e.g., after crosslinking the regions of photoresist exposed to the electromagnetic radiation) the method further comprising exposing a dry film of photoresist and/or a photomask (e.g., wherein the photomask is attached to the dry film of photoresist) to a temperature in a range of 80 degrees Celsius to 100 degrees Celsius (e.g., 85 degrees Celsius to 95 degrees Celsius, 95 degrees Celsius) for a duration sufficient to crosslink the at least one portion of the dry film of photoresist that was exposed to UV light through the photomask. Other temperature ranges are also possible.

In some embodiments, the method comprises exposing a dry film of photoresist and/or a photomask (e.g., wherein the photomask is attached to the dry film of photoresist) to a temperature in a range of 80 degrees Celsius to 100 degrees Celsius (e.g., 85 degrees Celsius to 95 degrees Celsius, 95 degrees Celsius) for a period of time in a range of 1 min to 30 min (e.g., 5 min to 25 min, 10 min to 20 min, 15 min). Other temperature and duration ranges are also possible.

In some embodiments, a method comprises exposing a dry film of photoresist and/or a photomask (e.g., wherein the photomask is attached to the dry film of photoresist) to a temperature in a range of 10 degrees Celsius to 30 degrees Celsius (e.g., 15 degrees Celsius to 25 degrees Celsius, 20 degrees Celsius) for a duration sufficient to cool the dry film of photoresist (e.g., comprising at least one crosslinked portion) and the photomask to the temperature. Other temperature ranges are also possible.

In some embodiments, a method comprises exposing a dry film of photoresist (e.g., comprising at least one crosslinked portion) and/or a photomask (e.g., wherein the photomask is attached to the dry film of photoresist) to a temperature in a range of 10 degrees Celsius to 30 degrees Celsius (e.g., 15 degrees Celsius to 25 degrees Celsius, 20 degrees Celsius) for a period of time in a range of 30 min to 90 min (e.g., 40 min to 70 min, 50 min to 70 min, 60 min). Other temperature and duration ranges are also possible.

In some embodiments, a method further comprises exposing a dry film of photoresist and/or a photomask to a developing solution.

In some embodiments, a method comprises exposing a dry film of photoresist and/or a photomask to a developing solution for a duration sufficient to remove any non-crosslinked portions of the dry film of photoresist from the dry film of photoresist.

In some embodiments, a method comprises exposing a dry film of photoresist and/or a photomask to a developing solution for a period of time in a range of 1 min to 30 min (e.g., 10 min to 30 min, 20 min). Other duration ranges are also possible.

In some embodiments, the developing solution comprises a developing solvent. Developing solutions include but are not limited to cyclohexanol, cyclohexanone, propylene glycol, and methyl ether acetate.

In some embodiments, a method comprises de-laminating the first and/or second dry film of photoresist from the photomask in the developing solution.

In some embodiments, a method comprises washing the developed dry film of photoresist. In some embodiments, a method comprises washing the developed dry film of photoresist in isopropanol. In some embodiments, a method comprises washing the developed dry film of photoresist in isopropanol for a duration sufficient to remove residual developing solution from the first and/or second dry film of photoresist. In some embodiments, a method comprises washing the developed dry film of photoresist in isopropanol for a period of time in a range of 1 min to 10 min (e.g., 2 min to 8 min, 3 min to 7 min, 5 min). Other duration ranges are also possible.

In some embodiments, a method comprises air drying the developed dry film of photoresist.

Photomask

In some embodiments, a photomask comprises a polymer. In some embodiments, a photomask comprises polyethylene terephthalate (PET).

In some embodiments the photomask is designed such that, during exposure to the developing solution, the dry film of photoresist detaches from the photomask. In some such embodiments, the photomask has a density of features (e.g., represented by a maximum pitch of features) such that the dry film of photoresist detaches from the photomask during development. By contrast, for example, if a photomask has no features (e.g., its entire surface area is transparent to the wavelength or range of wavelengths of electromagnetic radiation to which it is exposed), the photoresist might remain bound to the photomask in the developing solution and be difficult to remove. In some embodiments, by decreasing the maximum pitch of features in the photomask, a surface area of interaction between the photomask and the crosslinked portion(s) of the dry film of photoresist decreases. As used herein, the term "pitch" refers to the center-to-center distance between entities (e.g., features, wells), e.g., for an array of entities. Without being bound by theory, it is believed that a lower pitch of features in the photomask results in the developing solution being able to access a photoresist/photomask interface throughout the surface area with a shorter distance between accessible regions, such that the bond between the photoresist and photomask is more readily disrupted by the developing solution. In some embodiments, features of the photomask have a maximum pitch of 2 mm between any two adjacent features. In some embodiments, the patterned area of the photomask is larger than the area of the photoresist film. Without being bound by theory, it is believed that in some embodiments, the combination of a maximum pitch of 2 mm, features covering at least 10% of the area of the photomask, and the patterned area of the photomask being larger than the area of the photoresist film facilitates complete detachment of the photomask from the photoresist in developing solution. By contrast, standard approaches involve placing the patterned area of the photomask in the center of the photoresist with non-patterned area around the edges of the pattern. If this standard approach were combined with the methods described herein, the edges of the photoresist might not detach from the photomask in developing solution and might be difficult to detach from the photomask without damaging the film.

In some embodiments, a photomask comprises features (e.g., which will be through-holes that form the walls of wells in a bottomless array of wells comprising a dry film of photoresist, and which are also herein referred to as "wells" of the photomask) with a maximum pitch of 2 mm between any two adjacent features. In some embodiments, a photomask comprises features every 2 mm or less in any direction along a surface of the photomask. In some embodiments, a photomask has features with a pitch of at least 1 micron, at least 10 microns, at least 20 microns, or at least 50 microns. In some embodiments, a photomask has features with a pitch of at most 2 mm, at most 1 mm, at most 500 microns, or at most 200 microns. Combinations of the above-referenced ranges are also possible (e.g., in a range of 1 micron to 2 mm, 10 microns to 1 mm, 20 microns to 500 microns). Other ranges are also possible.

In some embodiments, features (e.g., "wells") on a photomask occupy at least 10% of the area of the photomask and at most 99.9% of the area of the photomask (e.g., 50%). In some embodiments, the "wells" on a photomask occupy at least 10%, at least 20%, at least 30%, at least 40%, or at least 50% of the area of the photomask. In some embodiments, the "wells" on a photomask occupy at most 99.9%, at most 99%, at most 90%, at most 80%, at most 70%, or at most 60% of the area of the photomask. Combinations of the above-referenced ranges are also possible (e.g., in a range of 10% to 99.9%, 20% to 90%, 30% to 80%). Other ranges are also possible.

As used herein, the term "features" of a photomask refers to masked portions (e.g., portions opaque to light in the wavelength range of the electromagnetic irradiation or light to which the photomask and/or dry film of photoresist is exposed) of the photomask, e.g., corresponding to the lateral locations of wells in a dry film photoresist formed by photolithography using the photomask.

Layered Devices

In some embodiments, the method further comprises contacting a bottomless array of wells (e.g., bottomless microwell array) with a base layer to form an array of wells.

In some embodiments, a base layer comprises a plastic sheet, an acrylic plastic sheet, a DNA microarray, a silicone elastomer sheet, polydimethylsiloxane (PDMS), or a porous membrane (e.g., a first porous membrane, e.g., a first porous membrane described herein), or a combination thereof.

In some embodiments, a method comprises bonding (e.g., by adhesive, by heat lamination) a base layer to a bottom surface of a bottomless array of wells (e.g., bottomless microwell array). In some embodiments, a method comprises heat-laminating the base layer to the bottom surface of the bottomless array of wells (e.g., bottomless microwell array) (e.g., in embodiments where the base layer comprises a porous membrane).

In some embodiments, a method comprises enclosing a bottomless array of wells (e.g., bottomless microwell array) and the base layer in a housing. In some embodiments, the housing comprises polystyrene. Other materials for the housing are also possible.

In some embodiments, the method further comprises loading beads into an array of wells or bottomless microwell array.

In some embodiments, a method comprises contacting a bottomless array of wells (e.g., bottomless microwell array) or the array of wells, at its top surface, with a second porous membrane described herein.

In some embodiments, the method further comprises contacting (e.g., positioning, bonding, heat laminating) the second porous membrane, at its exposed surface, with a second bottomless microwell array.

In some embodiments, a method comprises contacting a first bottomless array of wells (e.g., bottomless microwell array), at its top surface, with a second bottomless microwell array. In some embodiments, the second bottomless microwell array is produced by methods described herein.

In some embodiments, a method comprises randomly aligning a first bottomless array of wells (e.g., bottomless microwell array) with a second bottomless array of wells (e.g., bottomless microwell array). In some embodiments, a method comprises heat laminating the first bottomless array of wells (e.g., bottomless microwell array) with the second bottomless array of wells (e.g., bottomless microwell array).

In some embodiments, a method involves forming a plurality of through-holes (described herein) in a dry film of photoresist (described herein) using a photomask by methods described herein to form a first bottomless array of wells (described herein), and contacting (e.g., attaching, bonding) the first bottomless array of wells to a base layer (e.g., porous membrane) to form an array of wells. In some embodiments, the method further involves loading the array of wells with beads. In some embodiments, the method further involves contacting the top surface of the first bottomless array of wells with a porous membrane. In some embodiments, the method further involves contacting the top surface of the porous membrane with a second bottomless array of wells.

In some embodiments, a method involves forming a plurality of through-holes (described herein) in a dry film of photoresist (described herein) using a photomask by methods described herein to form a first bottomless array of wells (described herein), and contacting (e.g., attaching, bonding) the first bottomless array of wells to a base layer (e.g., porous membrane) to form an array of wells. In some embodiments, the method further involves contacting the top surface of the first bottomless array of wells with a second bottomless array of wells such that no more than one well from the first bottomless array of wells overlaps with no more than one well from the second bottomless array of wells and at least 70% of wells from the first bottomless array of wells overlap with a respective well from the second bottomless array of wells.

Uses of the Layered Device

Advantageously, the layered device (e.g., microfluidic device, array of wells, e.g., comprising a dry film of photoresist) described herein can be used for a variety of types of analyses of single cells, including but not limited to those described herein. For example, a first fluid comprising a plurality of cells and/or a plurality of beads can be flowed through any of the layered devices described herein (e.g., microfluidic device, array of wells, e.g., comprising a dry film of photoresist) to form a cell-loaded and/or a bead-loaded microwell array.

In some embodiments, a first fluid is flowed through the device and the first fluid comprises beads. In some embodiments, a first fluid is flowed through the device and the first fluid comprises cells. In some embodiments, a first fluid is flowed through the device and the first fluid comprises beads and cells. In some embodiments, a second fluid is flowed through the device and the second fluid comprises beads. In some embodiments, a second fluid is flowed through the device and the second fluid comprises cells.

Super-Poisson Loading

A shortcoming of traditional arrays for single cell analysis is that cells and/or beads are loaded into the array at a Poisson distribution. As is used herein, a "Poisson distribution" is a discrete probability distribution that expresses the probability of a number of events occurring in a fixed period of time or space if these events occur at a known average rate and are independent of one another. The Poisson distribution formula is as follows: $f(k;\lambda)=(e^{-\lambda}\lambda^k/k!)$ where k is the number of occurrences of an event and X is a positive real number of the expected number of occurrences during the given interval. In some embodiments, when a lateral device is cell-loaded at a Poisson distribution, at least 1% of the wells (e.g., of the first and/or second bottomless microwell array or the first and/or second array of wells) will have more than one cell. In some embodiments, when a lateral device is cell-loaded at a Poisson distribution, 1%-40%, e.g., 1-10% or 1%-2%, e.g., 1%, 2%, 5%, 10%, 15%, 20%, 25%, 30%, 35% or 40% of the wells will have more than one cell. In some embodiments, when a lateral device is bead-loaded at a Poisson distribution, at least 1% of the wells will have more than one bead. In some embodiments, when a lateral device is bead-loaded at a Poisson distribution, 1%-40%, e.g., 1-10% or 1%-2%, e.g., 1%, 2%, 5%, 10%, 15%, 20%, 25%, 30%, 35% or 40% of the wells will have more than one bead. In some embodiments, when a lateral device is cell-loaded at a Poisson distribution, at least 10% of the wells will have no cells. In some embodiments, when a lateral device is cell-loaded at a Poisson distribution, 10%-40%, e.g., 10%, 15%, 20%, 25%, 30%, 35% or 40% of the wells will have no cells. In some embodiments, when a lateral device is bead-loaded at a Poisson distribution, at least 10% of the wells will have no beads. In some embodiments, when a lateral device is bead-loaded at a Poisson distribution, 10%-40%, e.g., 10%, 15%, 20%, 25%, 30%, 35% or 40% of the wells will have no beads.

Thus, when a lateral device is cell-loaded (or bead-loaded) at a Poisson distribution, it will be clear that not all wells will contain a single cell (or a single bead) and thus not all the wells may be usable or provide useful "single-cell" (or "single-bead") information. Thus it is also clear that when loading occurs at a Poisson distribution, most of the wells in the array are unusable. This leads to significant waste of cells and/or beads, either or both of which may be scarce and/or expensive. The arrays provided herein, and their methods of use including super-Poisson distribution provide a robust solution to this short-coming of Poisson based analysis.

Accordingly, in contrast, in the layered devices provided herein, in some embodiments, one or more of the layers are cell and/or bead loaded at a super-Poisson distribution. As is used herein, a "super-Poisson distribution" means that the probability of a number of events occurring at the average rate in a fixed period of time or space if these events occur at a known average rate and are independent of one another is greater than it would be at a Poisson distribution. For example, if an array is loaded with beads and the average loading is 1 bead per well, a Poisson-loaded array would have fewer wells with 1 bead and more wells with 0 or 2 or more beads than a super-Poisson loaded array loaded with the same number of beads. In some embodiments, when a lateral device is cell-loaded at a super-Poisson distribution, 5% more (or more) of the wells have 1 cell than would a lateral device cell-loaded at a Poisson distribution with the same number of cells. In some embodiments, when a lateral device is cell-loaded at a super-Poisson distribution, 1-20% more, e.g., 1%, 5%, 10%, 15%, or 20% more of the wells (e.g., of the first and/or second bottomless microwell array or the first and/or second array of wells) have 1 cell than would a lateral device cell-loaded at a Poisson distribution with the same number of cells. In other words, super-Poisson loading results in a greater number of usable wells (e.g., those having a single cell and/or a single bead) as compared to Poisson loading. Similarly, in some embodiments, when a lateral device is bead-loaded at a super-Poisson distribution, 5% more (or more) of the wells have 1 bead than would a lateral device bead-loaded at a Poisson distribution with the same number of bead. In some embodiments, when a lateral device is bead-loaded at a super-Poisson distribution, 1-20% more, e.g., 1%, 5%, 10%, 15%, or 20% more of the wells have 1 bead than would a lateral device cell-loaded at a Poisson distribution with the same number of beads. In some embodiments, super-Poisson loading of beads into a lateral device is achieved by forming the lateral device to comprise wells having a largest lateral dimension in a range of 1 to 1.5 times the diameter of the beads, such that only one bead fits in a well.

Super-Poisson distribution of the loaded beads and/or cells results from flowing fluid through the layered device. Indeed, the fluid is able to flow through the device (e.g., from the top to the bottom of the wells) in embodiments in which the device has a porous bottom. Flowing liquid through the device causes the cells and/or beads to flow into the wells and towards the bottom of the device. In some embodiments, the cell and/or bead will block the well once it flows to the bottom of the well, causing the flow rate to decrease. This will decrease the likelihood that wells will become loaded with more than one cell and/or bead. This is exemplified, for example, in FIG. 12D, in which the first layer of the array 714 has wells sized such that the cell 722 will enter the array and block the porous membrane 702, thereby reducing the flow through the well such that other cells have a reduced likelihood of entering the well relative to wells that do not have reduced flow.

In some embodiments, 25% or more, 30% or more, 40% or more, 50% or more, 60% or more, 70% or more, 80% or more, or 90% or more of the wells (e.g., of the first and/or second bottomless microwell array or the first and/or second array of wells) are loaded with a single cell. In some embodiments, about 25% or more, about 30% or more, about 40% or more, about 50%, about 55%, about 60%, about 65%, about 70%, about 75%, about 80%, about 85%, about 90%, about 95%, or about 99% of the wells loaded with a single cell.

In some embodiments, 25% or more, 30% or more, 40% or more, 50% or more, 60% or more, 70% or more, 80% or more, or 90% or more of the wells (e.g., of the first and/or second bottomless microwell array or the first and/or second array of wells) are loaded with a single bead. In some embodiments, about 25% or more, about 30% or more, about 40% or more, about 50%, about 55%, about 60%, about 65%, about 70%, about 75%, about 80%, about 85%, about 90%, about 95%, or about 99% of the wells loaded with a single bead.

In some embodiments, 25% or more, 30% or more, 40% or more, 50% or more, 60% or more, 70% or more, 80% or more, or 90% or more of the wells (e.g., of the first and/or second bottomless microwell array or the first and/or second array of wells) are loaded with a single bead and a single cell. In some embodiments, about 25% or more, about 30% or more, about 40% or more, about 50%, about 55%, about 60%, about 65%, about 70%, about 75%, about 80%, about 85%, about 90%, about 95%, or about 99% of the wells loaded with a single bead and a single cell.

The fluid containing the cells and/or beads can be flowed through the wells in a variety of ways. For example, and without limitation, cells can be flowed through the array by applying vacuum in the flow direction of the array or applying pressure to the liquid in the flow direction through the array, e.g., by centrifuging the array.

In some embodiments, the cells and/or beads are flowed through the array for 30 minutes or less, 25 minutes or less, 20 minutes or less, 15 minutes or less, or 10 minutes or less. In some embodiments, the cells and/or beads are flowed through the array for 1-10 minutes, e.g., about 1-5 minutes or 1-5 minutes.

In some embodiments, the cells and/or beads are flowed through the array at 20° C.-40° C., e.g. 25° C.-35° C., e.g, about 30° C.

In some embodiments, the flow rate is 0.01-100 mL/min, e.g., 0.05-50 mL/min, e.g., 0.1-10 mL/min. In some embodiments, the flow rate is about 0.1, 0.2, 0.3, 0.4, 0.5, 0.6, 0.7, 0.8, 0.9, 1, 2, 3, 4, 5, 6, 7, 8, 9 or 10 mL/min.

Configuration of Bead and/or Cell-Loaded Devices

In some embodiments the bead/and or cell layered device (e.g., microfluidic device, array of wells, e.g., comprising a dry film of photoresist) is any device described herein. Exemplary bead and/or cell loaded devices are shown in FIGS. 12A-12C.

Figure 12A:
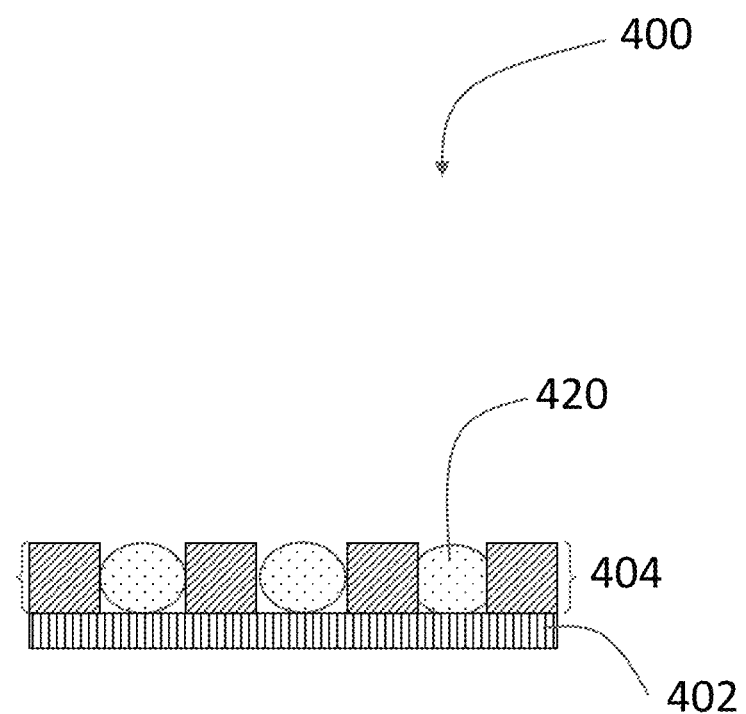
FIGS. 12A-12D are cross-sectional schematic diagrams of a layered devices described herein.

FIG. 12A represents a layered device (e.g., microfluidic device, array of wells, e.g., comprising a dry film of photoresist) having a first bottomless microwell array contacted to a porous membrane with each well of the array comprising a bead. FIG. 12A is a cross-sectional schematic diagram of a layered device 400 (e.g., a microfluidic device), according to certain non-limiting embodiments. Depicted layered device 400 includes bottomless array of wells 404 contacting (e.g., bonded to, e.g., by heat lamination) substrate 402. Substrate 402 may comprise, as non-limiting examples, glass, plastic, an elastomer (e.g., polydimethylsiloxane (PDMS)), and/or a porous membrane. Substrate 402 may comprise, as non-limiting examples, glass or plastic that has good optical clarity, e.g., useful for protein assays and/or tissue transcriptomics. In some embodiments, layered device 400 costs less than 1 U.S. dollar (USD) per array manufactured. In some embodiments, bottomless array of wells 404 is made at a scale of 0.3048 m long by 0.9144 m wide, by a method (e.g., photolithographic process) described herein, and diced to form smaller microwell arrays. Wells (may be a well described herein) in microwell array 404 each include a bead 420 (may be a bead described herein). In some embodiments, at least 70% of wells in microwell array 404 include a bead. The device may or may not include beads. It should be understood that an array may comprise any suitable number of wells (e.g., 1, 10, 100, 1000, or more wells) in one or two dimensions and/or may comprise wells of any suitable shape (e.g., cylindrical, rectangular prismatic, square prismatic, conical, or pyramidal shape) and/or size (e.g., largest lateral dimension). Other ranges are also possible.

Figure 12B:
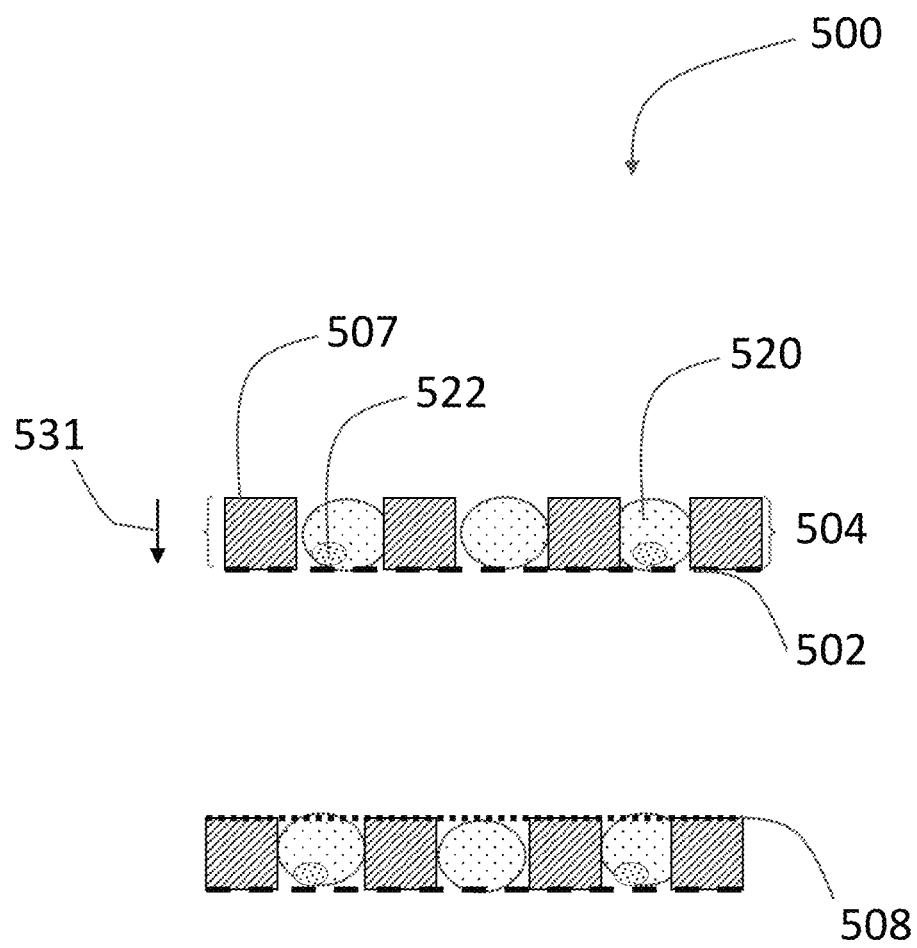

FIG. 12B shows a similar single layer device, except that each well comprises a bead and a cell. FIG. 12B is a cross-sectional schematic diagram of a layered device 500 (e.g., a microfluidic device), according to certain non-limiting embodiments. Depicted layered device 500 includes bottomless array of wells 504 contacting (e.g., bonded to, e.g., by heat lamination) porous membrane 502 (may be a porous membrane described herein). Wells (may be a well described herein) in microwell array 504 each include a bead 520 (may be a bead described herein). In some embodiments, porous membrane 502 has pores in a size range between or equal to 200 nm and 3 microns (e.g., 200 nm and 400 nm). In some embodiments, at least 70% of wells in microwell array 504 include a bead. Some wells (may be a well described herein) in microwell array 504 include a cell 522 (may be a cell described herein). In some embodiments, at least 70% of wells in microwell array 504 include a cell. The device may or may not include beads and/or cells. In some embodiments, the cells and/or beads were loaded by flowing a liquid comprising the cells and/or beads through the microwell array 504 in flow direction 531 (e.g., by pulling vacuum though the microwell array). In some embodiments, ultrafiltration membrane 508 is contacted with (e.g., attached to, bonded to) the top surface 507 of the microwell array 504, e.g., by pulling vacuum in the flow direction 531. This layered device 500 may be coupled with a fully automated liquid handler to load the cells and/or beads. It should be understood that an array may comprise any suitable number of wells (e.g., 1, 10, 100, 1000, or more wells) in one or two dimensions and/or may comprise wells of any suitable shape (e.g., cylindrical, rectangular prismatic, square prismatic, conical, or pyramidal shape) and/or size (e.g., largest lateral dimension). Other ranges are also possible.

Figure 12C:
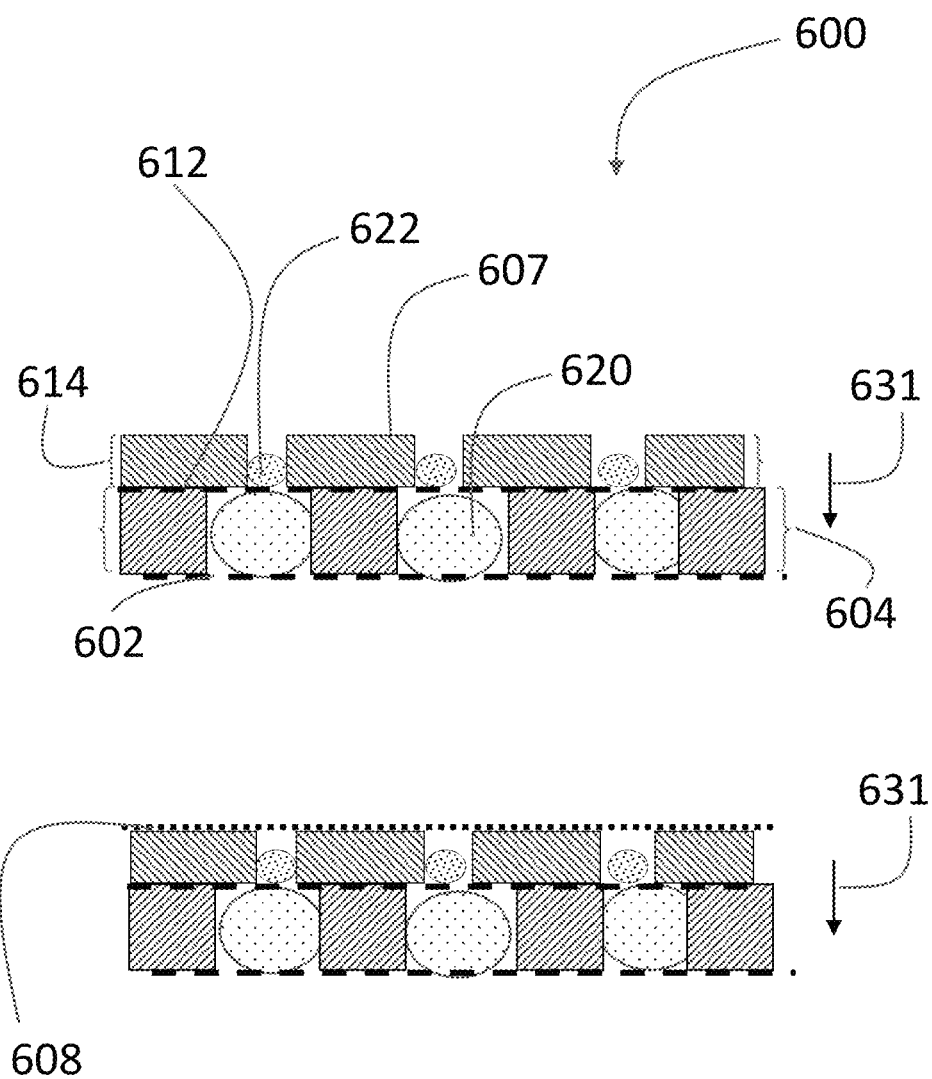

In the configuration in FIG. 12C, the device has a double layer of bottomless microwell arrays (e.g., first bottomless microwell array and second bottomless microwell array) and further comprises a porous membrane bound to the bottom of the first bottomless microwell array, with wells configured to fit beads (e.g., a diameter of 15-100 microns) on the bottom layer and wells configured to fit cells (e.g., a diameter of 1-10 microns) on the top layer. FIG. 12C is a cross-sectional schematic diagram of a layered device 600 (e.g., a microfluidic device), according to certain non-limiting embodiments. Depicted layered device 600 includes bottomless array of wells 604 contacting (e.g., bonded to, e.g., by heat lamination) first porous membrane 602 (may be a porous membrane described herein) and second porous membrane 612 (may be a porous membrane described herein). Wells (may be a well described herein) in microwell array 604 each include a bead 620 (may be a bead described herein). In some embodiments, first porous membrane 602 and/or second porous membrane 612 have pores in a size range between or equal to 200 nm and 3 microns (e.g., 200 nm and 400 nm). In some embodiments, at least 70% of wells in microwell array 604 include a bead. Second porous membrane 612 contacts microwell array 614. Wells (may be a well described herein) in microwell array 614 each include a cell 622 (may be a cell described herein). The device may or may not include cells. In some embodiments, at least 70% of wells in microwell array 614 include a cell. Each well in depicted microwell array 614 overlaps with a corresponding well in microwell array 604. In some embodiments, between or equal to 70% and 85% of wells in microwell array 614 overlap with a corresponding well in microwell array 604 (e.g., due to random alignment of the two microwell arrays). In some embodiments, the largest lateral dimension and pitch of the wells in microwell arrays 604 and 614 are such that at most one well in microwell array 604 can overlap with a corresponding well in microwell array 614. In some embodiments, the wells of microwell array 604 have a largest lateral dimension in a range of 20 microns to 500 microns (e.g., 50 microns), and the wells of microwell array 614 have a largest lateral dimension in a range of 1 microns to 10 microns (e.g., 5 microns). In some embodiments, the cells and/or beads were loaded by flowing a liquid comprising the cells and/or beads through the layered device 600 in flow direction 631 (e.g., by pulling vacuum though the microwell array). In some embodiments, the beads were loaded by exposing the device 600 to a liquid comprising the beads (e.g., by allowing the beads to settle into the device), e.g., by flowing a liquid comprising the beads in flow direction 631 (e.g., by pulling vacuum though the microwell array 604, by centrifuging with the array) through a portion of layered device 600 that included porous membrane 602 and microwell array 604 but not the other components depicted. Then, in some embodiments, second porous membrane 612 and microwell array 614 were positioned (e.g., bonded together) as depicted in layered device 600. In some embodiments, the cells were loaded by flowing a liquid comprising the cells in flow direction 631 (e.g., by pulling vacuum though the layered device 600). Without being bound by theory, it is believed that once a cell loads into a well, it clogs the base of the well, eliminating flux through the well and thereby preventing a second cell from loading. In some embodiments, ultrafiltration membrane 608 is contacted with (e.g., attached to, bonded to) the top surface 607 of the layered device 600, e.g., by pulling vacuum in the flow direction 631. This layered device 600 may be coupled with a fully automated liquid handler to load the cells and/or beads. It should be understood that an array may comprise any suitable number of wells (e.g., 1, 10, 100, 1000, or more wells) in one or two dimensions and/or may comprise wells of any suitable shape (e.g., cylindrical, rectangular prismatic, square prismatic, conical, or pyramidal shape) and/or size (e.g., largest lateral dimension). Other ranges are also possible. In some embodiments, cells are lysed, and after lysis, the contents of each cell diffuse from a well in microwell array 614 into a corresponding adjacent well in microwell array 604, likely containing a bead (e.g., 70% or more of wells in microwell array 604 contain a bead).

To fabricate such an array, in some embodiments, the first bottomless microwell array bound to the first porous membrane on the bottom surface is loaded with beads by flowing a first fluid comprising a plurality of beads through the device, using the methods described herein. A second bottomless microwell array is then sealed to the bead-loaded first bottomless microwell array using the methods described herein, and the second bottomless microwell array is then loaded with cells by flowing a second fluid comprising a plurality of cells through the device using the methods described herein.

Figure 12D:
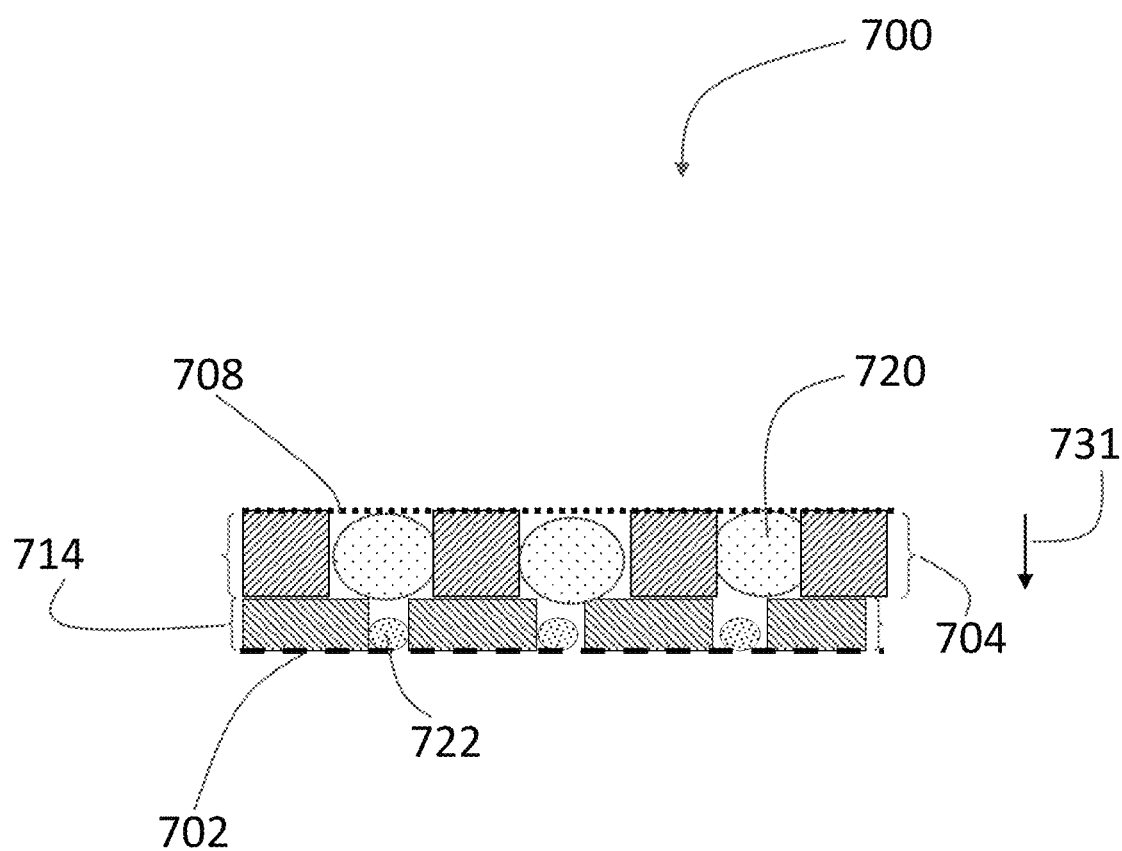

In the configuration in FIG. 12D, the device has a double layer of bottomless microwell arrays (e.g., first bottomless microwell array and second bottomless microwell array) and further comprises a porous membrane bound to the bottom of the first bottomless microwell array, with wells configured to fit cells (e.g., a diameter of 1-10 microns) on the bottom layer and wells configured to fit cells (e.g., a diameter of 15-100 microns) on the top layer. FIG. 12D is a cross-sectional schematic diagram of a layered device 700 (e.g., a microfluidic device), according to certain non-limiting embodiments. Depicted layered device 700 includes first bottomless array of wells 714 contacting (e.g., bonded to, e.g., by heat lamination) first porous membrane 702 (may be a porous membrane described herein) and second bottomless array of wells 704. In some embodiments, first porous membrane 702 has pores in a size range between or equal to 200 nm and 3 microns (e.g., 200 nm and 400 nm). In some embodiments, second bottomless array of wells 704 contacts (e.g., is bonded to, e.g., by heat lamination) ultrafiltration membrane 708. Wells (may be a well described herein) in microwell array 714 each include a cell 722 (may be a cell described herein). Wells (may be a well described herein) in microwell array 704 each include a bead 720 (may be a bead described herein). The layered device 700 may or may not include beads and/or cells. In some embodiments, at least 70% of wells in microwell array 714 include a cell. In some embodiments, at least 70% of wells in microwell array 704 include a bead. Each well in depicted microwell array 714 overlaps with a corresponding well in microwell array 704. In some embodiments, between or equal to 70% and 85% of wells in microwell array 714 overlap with a corresponding well in microwell array 704 (e.g., due to random alignment of the two microwell arrays). In some embodiments, the largest lateral dimension and pitch of the wells in microwell arrays 704 and 714 are such that at most one well in microwell array 704 can overlap with a corresponding well in microwell array 714. In some embodiments, the cells and/or beads were loaded by flowing a liquid comprising the cells and/or beads through the layered device 700 in flow direction 731 (e.g., by pulling vacuum though the microwell array). In some embodiments, the cells were loaded by flowing a liquid comprising the cells in flow direction 731 (e.g., by pulling vacuum though the layered device 700). Without being bound by theory, it is believed that once a cell loads into a well, in some embodiments, it clogs the base of the well, eliminating flux through the well and thereby preventing a second cell from loading. Then, in some embodiments, the beads were loaded by exposing the device 700 to a liquid comprising the beads (e.g., by allowing the beads to settle into the device), e.g., by flowing a liquid comprising the beads in flow direction 731 (e.g., by pulling vacuum though the layered device 700) through layered device 700. In some embodiments, ultrafiltration membrane 708 is contacted with (e.g., attached to, bonded to) the top surface of the layered device 700, e.g., by pulling vacuum in the flow direction 731. This layered device 700 may be coupled with a fully automated liquid handler to load the cells and/or beads. It should be understood that an array may comprise any suitable number of wells (e.g., 1, 10, 100, 1000, or more wells) in one or two dimensions and/or may comprise wells of any suitable shape (e.g., cylindrical, rectangular prismatic, square prismatic, conical, or pyramidal shape) and/or size (e.g., largest lateral dimension). Other ranges are also possible. In some embodiments, cells are lysed, and after lysis, the contents of each cell diffuse from a well in microwell array 714 into a corresponding adjacent well in microwell array 704, likely containing a bead (e.g., 70% or more of wells in microwell array 704 contain a bead).

Characterization of Single Cells

The cell-loaded and/or a bead-loaded layered device (e.g., microfluidic device, array of wells, e.g., comprising a dry film of photoresist) described herein can be used for a variety of types of biochemical analyses of single cells. For example, the lateral device can be used for high throughput biochemical analysis such as cell lysis performed in the well, and subsequently one or more of RT-PCR, RNA-seq, PCR, qPCR, DNA-seq, mass spectroscopy, ATAC-seq, bisulfite sequencing, immuno-PCR, in-situ sequencing, rolling circle amplification, in-situ hybridization, proximity extension assays, immunofluorescence, ELISA, reverse ELISA, multiple displacement reaction, DNase hypersensitivity, chip-seq, or any other genomic assay using methods known in the art for use with conventional arrays for single cell analysis (such as is described, for example, in PCT US17/13719 or WO 2018/132635, the entire contents of each of which is incorporated herein by reference).

In some embodiments, the cells are bacterial cells. In some embodiments, the cells are eukaryotic cells. In some embodiments, the cells are mammalian cells. In some embodiments, the cells are murine cells. In some embodiments, the cells are primate cells. In some embodiments the cells are human cells. In some embodiments, the cells are tumor cells. In some embodiments, the cells are non-mammalian cells and may be prokaryotic cells or other eukaryotic cells. The cells (or nucleic acid source) may be naturally occurring or it may be non-naturally occurring. An example of a non-naturally occurring nucleic acid is a synthetically produced cell.

In some embodiments, after the layered device is cell and/or bead loaded, it is sealed on the top surface with a porous membrane such as an ultrafiltration membrane described herein. The membrane is sealed using methods described herein, e.g., with a heated press or a PCR machine, or by bringing the membrane into contact with the top of the layered device, placing a solid surface, e.g., a glass slide, on top of the membrane, and clamping the layered device to the slide. In some embodiments, the layered device is clamped to the slide for 30 minutes or more, e.g., 30 minutes-2 hours, e.g., about 1 hour.

In some embodiments, cells within the lateral device are lysed by applying lysis buffer to the top of the layered device. Exemplary lysis buffers are known in the art and include guanidine hydrochloride. Cells are lysed within the lateral device and the membrane retains the contents of the cells within the lateral device while the lysis buffer can be washed out.

In some embodiments, the methods further comprise analyzing protein and/or nucleic acids of the lysed cells.

In some embodiments, the single-cell transcriptomes of each cell are then isolated. This is accomplished by first capturing mRNA molecules released by the lysed cells on the barcoded bead that is resident in the well. After capture, the unique barcode of the bead (and therefore, of the well) is incorporated into first strand cDNA synthesized using reverse transcription from (and thus complementary to) the captured mRNA transcripts, in the process of creating a cDNA library from each single cell. The bead barcode therefore identically marks (or labels) all the captured transcripts from the same single cell. The barcoded cDNA libraries may then be combined, with each cDNA marked as to its single cell origin, and may undergo whole transcriptome amplification (WTA), and then sequencing.

Exemplary Embodiments

Provided herein is a free-standing photoresist film that can be made using a scalable manufacturing method and the method of making the film. Traditionally, photoresist films are manufactured on a substrate, which provides support for the photoresist so that a liquid coating of the photoresist can be coated on the substrate. To manufacture a free-standing photoresist film using the traditional method, the photoresist film is separated with, or "lifted off" from the substrate, which requires cumbersome process and is not scalable. The methods provided herein have overcome these limitations.

Provided herein is a method of manufacturing a free-standing photoresist film. The method can comprise several steps such as laminating a photoresist film with a photomask, exposing the photoresist film through the photomask to strengthen a portion of the photoresist, removing an unstrengthened portion of the photoresist (development step), and separating the photoresist film from the photomask. The photoresist film can be a negative or positive photoresist film, and depending on the type of the photoresist, a suitable light source such as electron-beam, ultraviolent light (UV), or other short wavelengths light source can be used for strengthening. A photomask described herein can comprise a plurality of features, including but not limited to, repeating features, non-repeating features, solid features, shaded features, arrays (such as an array of circles, squares, rectangles, ovals, triangles, and pentagons), letters, and drawings. As used herein, the term "feature distance" refers to both (i) the distance between edges of features and (ii) the distance between edges of features and edges of the photomask.

Accordingly, some of the photomasks described herein have a maximum feature distance of no more than 5, 4, 3, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, or 0.1 mm, and some of the photomasks described herein have a maximum feature distance of no less than 3, 2, 1.9, 1.8, 1.7, 1.6, 1.5, 1.4, 1.3, 1.2, 1.1, 1, 0.9, 0.8, 0.7, 0.6, 0.5, 0.1, or 0.01 mm. In some cases, the maximum feature distance of the photomask is about 2, 1.5, or 1 mm. During the exposure process, the photomask can cover a minimum percentage of the surface of the photoresist film, or the exposed surface of the photoresist film. For example, the photomask can cover at least 75%, 80%, 85%, 90%, 91%, 92%, 93%, 94%, 95%, 96%, 97%, 98%, or 99% of the surface. For another example, the photomask can cover the entire surface, or the entire exposed surface of the photoresist film. Further, some of the photomasks can have feature coverages that a maximum percentage of the surface of the photoresist film is exposed to the light source, i.e., for negative photoresist, a maximum percentage of the surface of the photoresist is strengthened. For example, the strengthened portion of the photoresist can be at most 25%, 30%, 35%, 40%, 45%, 50%, 60%, or 75% of the photoresist by surface area.

The laminate of the photoresist film and the photomask can be exposed to one or more types of radiation or light from a preselected source for a time sufficient to strengthen the film, thereby forming a photoresist film that has strengthened portions and some unstrengthened portions. For negative photoresist films, strengthening can involve polymerizing or crosslinking to create a polymerized or crosslinked portion, respectively. The strengthened portion is substantially resistant to a dissolving agent and thus would not be removed during the development process. During the development step, the photoresist is developed and the unstrengthened portion is removed, e.g., by dissolving it in a dissolving agent. The method of manufacturing can comprise a separation step where the photoresist film is separated from the photomask. The separation can occur simultaneously with or after the development step, and it can occur naturally or through manipulation. In some embodiments, the separation occurs naturally when the photoresist is being developed. It should be noted that a person skilled in the art would understand that for positive photoresist films, the exposed portion can become soluble and be removed during the development step. The method can further comprise removing a release-liner from the photoresist. The release-liner can be removed after lamination, for example, before or after the exposure step or the development step.

In one aspect, provided herein is a substrate-free two-layer laminate comprising a photoresist film and a photomask, from which laminate a free-standing photoresist film can be produced. After exposure, the photoresist film can comprise a strengthened portion and an unstrengthened portion, and the strengthened portion is substantially resistant to a dissolving agent used in the development process. Upon contacting with a dissolving agent, the unstrengthened portion dissolves to form a pattern, such as a plurality of through-holes. The through-holes can occupy at least 25%, 30%, 35%, 40%, 45%, 50%, 60%, 75%, 80%, 85%, or 90% of the photoresist by surface area.

The photoresist film can comprise a top surface and a bottom surface, and it can comprise a strengthened (e.g., crosslinked) portion and an unstrengthened (e.g., uncrosslinked) portion. For some of the photoresist films, the unstrengthened (e.g., uncrosslinked) portion can be removed in a dissolving agent (or a developer) to form a plurality of through-holes from the top surface to the bottom surface, and each hole has a top opening on the top surface and a bottom opening on the bottom surface. Generally, during a development stage, the unstrengthened portion of the photoresist can be removed by a developer, thus creating a pattern on the photoresist, e.g., a plurality of hexagonally packed through-holes.

Some of the photoresist films can have a thickness of at least or at most 0.5, 1, 2, 3, 4, 5, 6, 7, 8, 9, 10, 20, 30, 40, 50, 60, 70, 80, 90, 100, 150, 200, 250, 300, 350, 400, 450, or 500 microns. The plurality of through-holes can have an average diameter of the top openings and an average diameter of the bottom openings; the two average diameters can be the same or different. Some photoresist films have an average diameter of the top openings, the bottom openings, or both openings of at least 1, 5, 10, 15, 20, 25, 30, 35, 40, 45, 50, 75, 100, 200, or 500 microns. Some photoresist films have an average diameter of the top openings, the bottom openings, or both openings of at most 5, 10, 15, 20, 25, 30, 35, 40, 45, 50, 75, 100, 200, or 500 microns. The geometry of the top openings and the geometry of the bottom openings can be selected from a square, a circle, a rectangle, a triangle, a pentagon, a hexagon, a heptagon, an octagon, or other geometries. Additionally, the plurality of the through-holes of the photoresist film can have a shape that is a cylinder, a cube, a cuboid, a cone, a triangle pyramid, a square pyramid, or a triangular prism. Further, the walls of the through-holes of the photoresist can comprise a functional wall surface, such as those described in PCT/US17/13791, which is hereby incorporated by reference in its entirety. For some applications, the size and shape of the through-holes are configured to hold one cell or one bead per through-hole.

The photoresist films made by the herein described methods can be used for various applications. For example, the picowell, microwell, or bottomless microwell array can comprise a free-standing photoresist film or is a free-standing photoresist film. In one aspect, a microwell device can comprise a photoresist film and a porous bottom membrane. The porous bottom membrane can be in contact with the bottom surface of the photoresist film. A microwell device can also comprise two photoresist films in parallel (a first photoresist film and a second photoresist film), optionally bound with each other, wherein the bottom surface of the second photoresist film is facing the top surface of the first photoresist film. The sizes of the through-holes of the two photoresist films can be the same or different; for example, the through-holes of the first film can be larger or smaller than the through-holes of the second film and they can have the same or different shape and geometry. Some of the devices can comprise a porous membrane between the first and the second photoresist film; and some of the devices can comprise a membrane, either solid or porous, on the top surface of the second photoresist film.

The described porous membrane can have a desired membrane flux. For example, the porous membrane can have a flux rate of at least 0.1, 0.5, 1, 2, 3, 4, 5, 10, 15, 20, 25, 30, 35, 40, 50, 60, 70, 80, 90, or 100 mL/min/cm$^2$ as measured by the initial flux rate of water at 10 pounds per square inch (psi), which water can be pre-filtered or unfiltered. For another example, the porous membrane can have a flux rate of at most 0.1, 0.5, 1, 2, 3, 4, 5, 10, 15, 20, 25, 30, 35, 40, 50, 60, 70, 80, 90, 100, or 200 mL/min/cm$^2$ as measured by the initial flux rate of water at 10 psi. The porous membrane can be a dry film membrane or a hydrogel-based membrane.

The porous membrane can be configured to retain an object of interest, such as a cell, a bead, a genome, a nucleic acid, a virus, a nucleus, a protein, a peptide, or other biological macromolecules. The cell can be a bacteria, plant, or animal such as mammal cell. The cell can be a blood cell such as white blood cell (e.g., monocytes, lymphocytes, neutrophils, eosinophils, basophils, and macrophages), red blood cell (erythrocytes), or platelet. Some methods that are applicable to blood cells analyses are described in PCT/US2018/013443, which is hereby incorporated by reference in its entirety. The cell can also be a healthy cell or an unhealthy cell (e.g., infected cell or tumor cell). Accordingly, depending on the application, the porous membrane can have an average pore size of at least 1, 2, 3, 4, 5, 6, 7, 8, 9, 10, 15, 20, 25, 30, 35, 40, 45, 50, 75, 100, 150, 200, 250, 300, 350, 400, 450, 500, or 1000 nm. The porous membrane can also have an average pore size of at most 5, 10, 15, 20, 25, 30, 35, 40, 45, 50, 75, 100, 150, 200, 250, 300, 350, 400, 450, 500, 1000, or 5000 nm.

A microwell device can further accommodate a tissue section in contact with the top surface of the photoresist film. A microwell device can also comprise beads (either pre-loaded, e.g., one or more beads per through-hole, or loaded after the cells) and/or cells in the through-holes.

In one aspect, provided herein is a bottomless microwell array comprising the photoresist film. The microwell array can comprise a top surface, a bottom surface, and a plurality of through-holes from the top to the bottom surface, wherein each hole has a top opening on the top surface and a bottom opening on the bottom surface. Further provided herein are methods of using a bottomless microwell array, regardless whether the array comprises the photoresist film.

In one aspect, provided herein is a method of cellular loading. The method can comprise flowing a fluid sample comprising a plurality of cells through a microarray device, which comprises a bottomless microwell array and a porous bottom membrane in contact with the bottom surface of the microwell array. The method of cellular loading can comprise loading the cells by gravity or applying a pressure gradient from the top opening to the bottom opening of at least one of the plurality of through-holes, thus loading a single cell into the at least one through-hole. The pressure gradient can be generated by any means including applying vacuum or forcing a fluid flow. The method can comprise retaining the cell at the bottom of the at least one through-hole by applying a pressure gradient. When a cell is retained at the bottom of the through-hole, the pressure gradient within the through-hole can be reduced, e.g., to a level insufficient to induce a loading of a second cell such that only a single cell is loaded per hole. The method can further comprise inverting the microwell array while the cell is retained, such that the unloaded cells can be removed, e.g., by a fluid flow, and the loaded cell can be retained. The method can also comprise washing the cell or the microwell array when the microwell array is inverted. Additionally, the method can further comprise reversing the inverted microwell array, and after the reversing, the pressure gradient can be optionally removed. Using the method of cellular loading, at least a portion of the plurality of through-holes may be loaded with a single cell per through-hole.

In one aspect, provided herein is a method of culturing or storing isolated cells. The method can comprise flowing a fluid sample comprising a plurality of cells through the microarray device. The method can also comprise loading at least one cell of the plurality of cells into the through-holes by gravity or by application of a pressure gradient. The method can further comprise flowing a media through the microwell array and/or submerging the microwell array in a media such that at least a portion of the plurality of through-holes are fluidically connected with the media through the top, the bottom, or both openings. The media can be a buffer, a cell culture media, or a fixative. For some applications, a porous top membrane can be applied above the top surface of the microwell array. For certain applications such as sequencing, the method can comprise flowing a fluid sample comprising a plurality of beads through the microwell array. The method can further comprise storing the microarray at a temperature for more than a day, a week, a month, 6 months, or a year, and the temperature can be ambient temperature or any temperature below or above 40° C., 30° C., 20° C., 10° C., 0° C., −10° C., −20° C., −30° C., −40° C., −50° C., −60° C., −70° C., or −80° C.

In one aspect, provided herein is a method of analyzing a tissue section, for example, spatially locating transcripts in the tissue section. The method can comprise contacting the tissue section with a microarray device that comprises a bottomless microwell array (e.g., a photoresist film) and a porous bottom membrane that is in contact with the bottom surface of the microwell array. A portion of the plurality of through-holes can comprise one or more barcoded transcript capture beads, and/or one or more functional surfaces that comprise a unique spatial barcode with known location on the microarray. The method can comprise hydrating the through-holes, either before or after the tissue is attached to the microwell array. For some devices, better hydration can be achieved by hydrating the through-holes before the tissue section is attached. The method can further comprise generating cDNA sequences from the transcripts, and/or generating bead barcode: spatial barcode hybrid molecules through primer extension of spatial barcodes bound to transcript capture beads. The method can further comprise matching the bead barcode in the cDNA to the bead barcode: spatial barcode hybrid molecule, thus locating the transcript on the microarray.

It should be noted that a skilled artisan would appreciate the various ways of using and assembling the device; a sample (such as a cell or a tissue) can be attached to or loaded into the device before or after the device is fully assembled. Take the tissue section analysis as an example, as one of the alternatives of the above described process, the tissue can be attached to the top surface of the bottomless microwell array, followed by hydration, with or without the beads, and then the porous membrane can be applied to the bottom surface of the microwell array. If beads are not pre-loaded, they can be loaded before the bottom porous membrane is attached. Similar principles apply to other samples such as cells and beads. When the device comprises two or more photoresist films or two or more porous membranes, the sequence of assembling the device and sample can also vary depending on the type of sample and the application; all are encompassed by this disclosure.

In one aspect, a single cell analyses kit can comprise one or more microarrays each comprising a photoresist film and at least one porous membrane. The kit can comprise additional components, including without limitation, a second porous membrane, a membrane applicator, a holder of the microarray, a membrane frame, a hybridization chamber plate, a buffer, a cell culture media, a fixative, beads, a manual clamp, a crowding agent, DNA polymerase, a thermocycler adaptor, or any combination thereof. In some of the kits, beads are pre-loaded in one or more of the microarrays, e.g., one bead per through-hole.

Kits

In some instances, it may be desirable to reduce the amount of manual processing and manipulation associated with preparing samples for analysis. This may help to both decrease the amount of time associate with processing samples as well as reduce the cost for processing the samples. For example, a kit including components for the processing of samples may be provided to a practitioner for loading a plurality of microwell arrays for bulk processing. While any number of different methods and kits may be used for such an application, possible embodiments of kits and their use are detailed further below.

Figure 14:
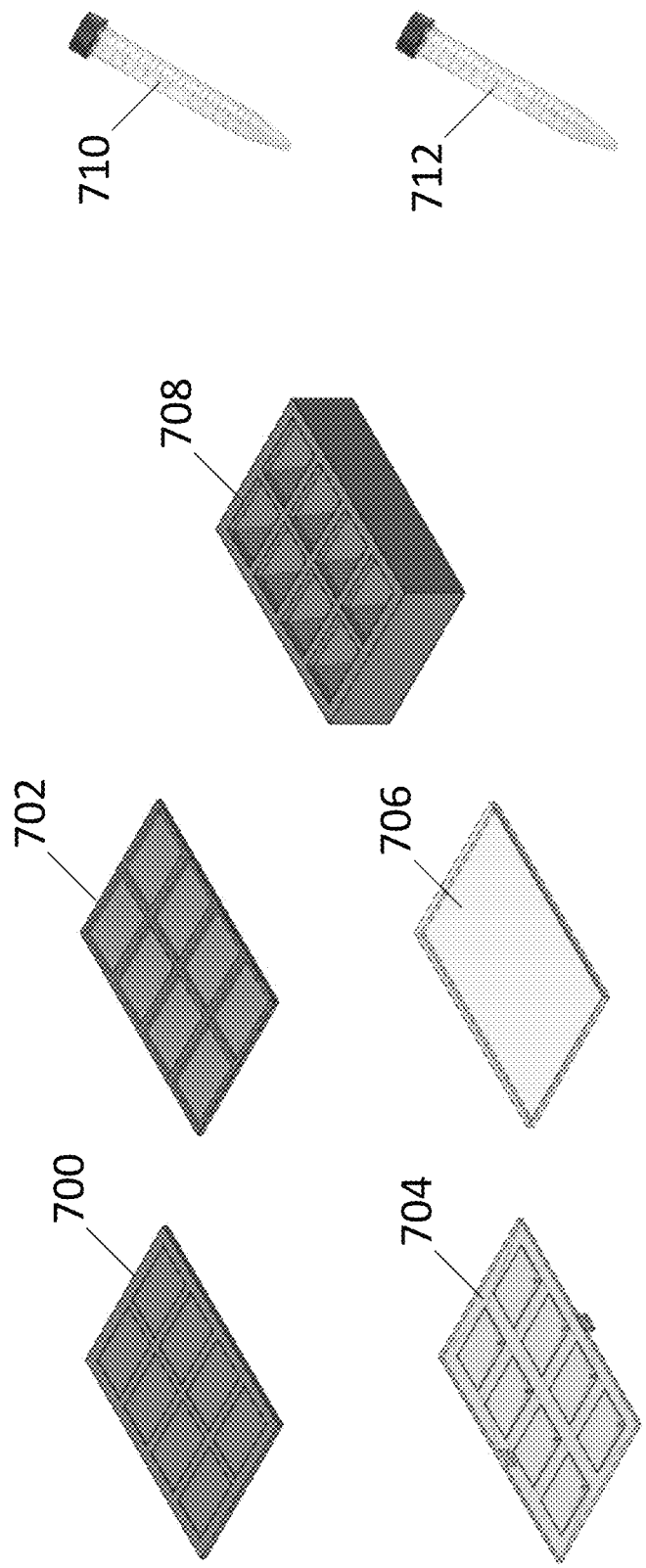
FIG. 14 is a schematic perspective view of one embodiment of a kit used for processing a plurality of microwell arrays.

FIG. 14 presents one embodiment of a kit for processing biological samples. The kit may include one or more of a base plate 700, a membrane plate 702, which may include one or more membranes, a hybridization plate 704, a cover 706, a collection plate 708, a hybridization buffer 710, a lysis buffer 712, combinations thereof, and/or any other appropriate component or solution. In some embodiments, the kit may also include written instructions for using the kit to process biological samples.

Figure 16:
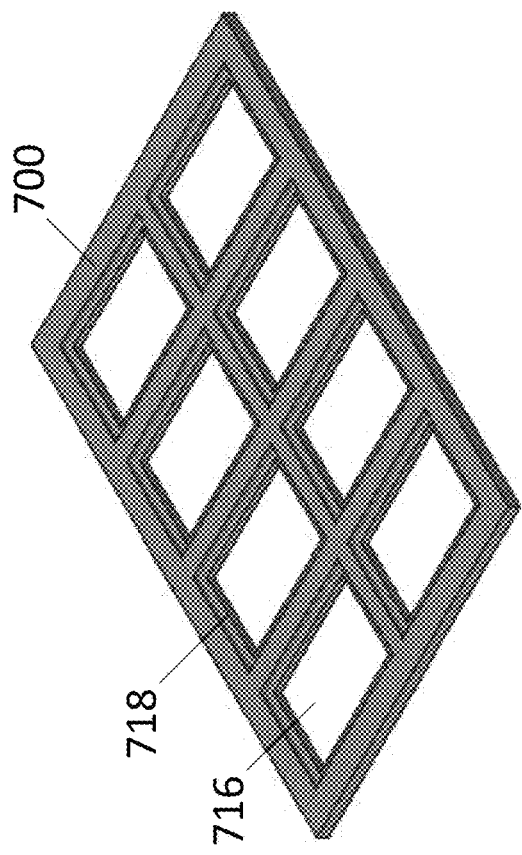
FIG. 16 is a schematic perspective view of another embodiment of a base plate for supporting a microwell array.
Figure 15:
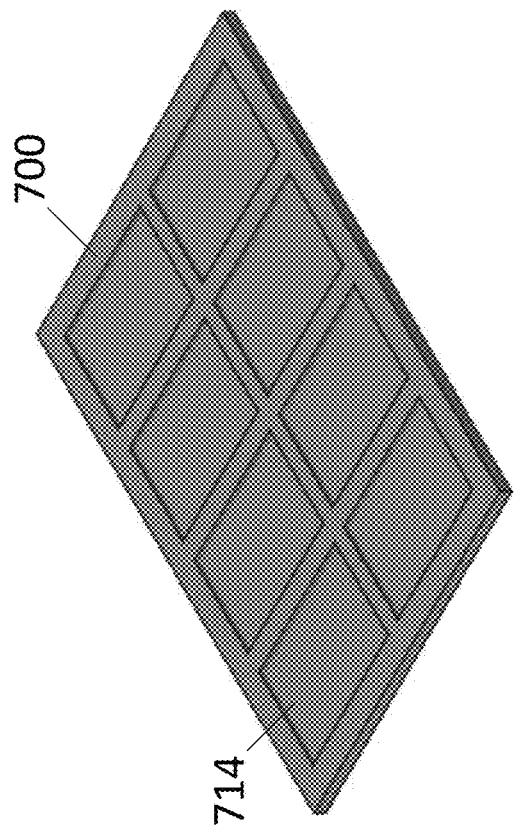
FIG. 15 is a schematic perspective view of one embodiment of a base plate for supporting a microwell array.

FIGS. 15 and 16 illustrate two possible embodiments of a base plate 700. The base plates may include a plurality of receptacles formed in a surface, such as a top surface, of the base plate. Each of the receptacles may be sized and shaped to receive a microwell array therein. For example, as shown in FIG. 15, the receptacles may be depressions 714 formed in a top surface of the base plate such that each receptacle includes a bottom surface upon which the individual microwell arrays may be disposed. In some instances, the depressions may be deep enough such that the microwell arrays are fully received within the receptacles. Such an embodiment may be useful with microwell arrays with closed bottoms where the individual wells do not extend all the way through the arrays. In another embodiment, the base plate may include receptacles in the form of a plurality of through-holes 716 and surrounding lips 718. The individual through-holes and lips may be sized and shaped to both receive and support a microwell array therein. In such an embodiment, the bottom surfaces of the microwell arrays disposed in the base plate may be exposed to the environment through the bottom openings of the through-holes. Such an embodiment may be useful in applications where the microwell arrays include microwells that extend completely through the arrays as previously discussed. However, embodiments in which these separate base plates are used with different types of microwell arrays with and/or without microwells that extend completely through the arrays are also contemplated as the disclosure is not so limited.

Figure 17:
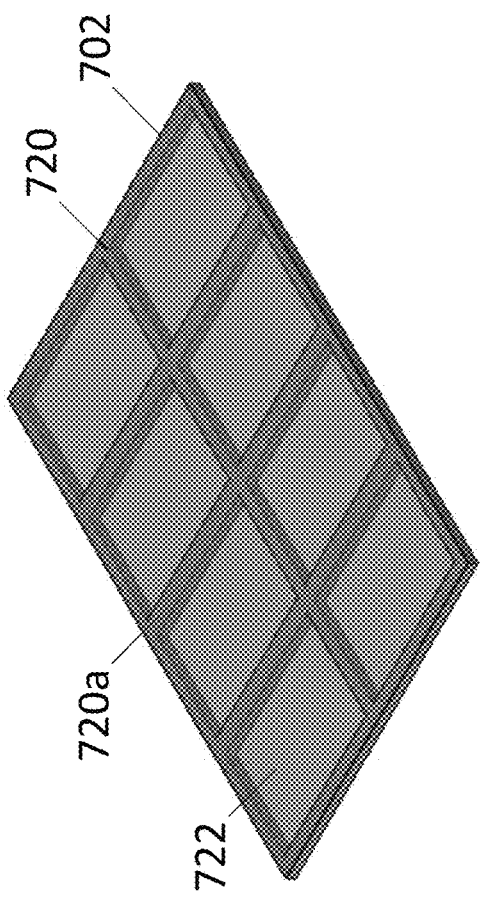
FIG. 17 is a schematic perspective view of one embodiment of a membrane plate.

FIG. 17 depicts one possible embodiment of a membrane plate including one or more membranes 722 that are configured to be attached to a surface of a base plate such that they cover the plurality of receptacles formed in the base plate. In some instances, this may simply correspond to a single membrane sheet that may be attached to the base plate. However, in some instances, it may be desirable to either provide support to the one or more membranes and/or to aid in isolating the plurality of receptacles from each other. For example, the membrane plate may include a frame 720 with a plurality of ribs 720a, or other structures, that the one or more membranes are disposed on and attached to. Further, as illustrated in figure, the ribs, or other structures, are laid out such that they surround the periphery of the individual receptacles of a base plate when disposed on a surface of the base plate including the receptacles. When properly bonded to the base plate, the membrane plate may prevent flow between the individual receptacles through the membrane plate itself while still permitting fluid communication into and out of the arrays in the receptacles through the isolated portions of the one or more membranes.

Figure 18:
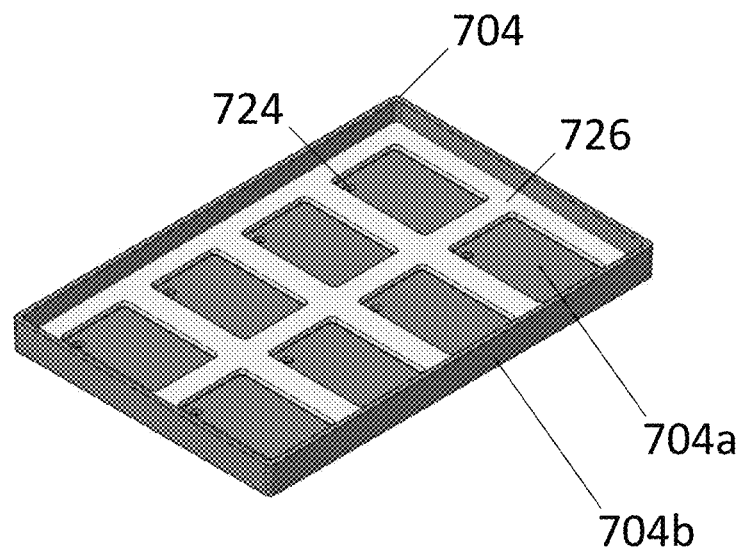
FIG. 18 is a schematic perspective view of one embodiment of a hybridization plate.
Figure 19:
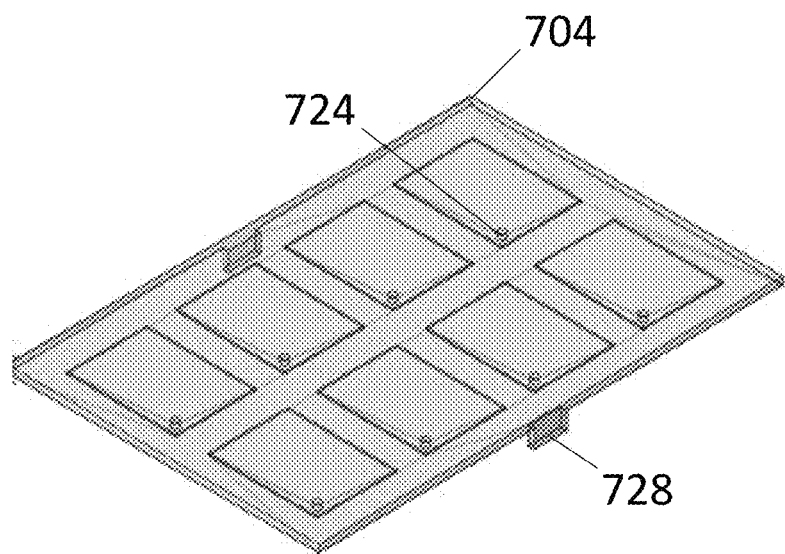
FIG. 19 is a schematic perspective view of another embodiment of a hybridization plate.

FIGS. 18 and 19 illustrate two possible embodiments for a hybridization plate 704. In both embodiments, the hybridization plate includes a plate 704a with openings 724 formed therein. The openings may be distributed across the plate such that the individual openings are in fluid communication with separate receptacles when the hybridization plate is assembled with the base plates described above. In some embodiments, the hybridization plate may include a lip 704b that surrounds, and extends in a direction perpendicularly out from, an outer periphery of the plate. The lip may be sized and shaped to surround a corresponding periphery of the base plate when the hybridization plate is assembled thereto as described further below. In the embodiment of FIG. 18, the hybridization plate may include an adhesive 726 in the form of an adhesive gasket disposed on an interior surface of the plate which is intended to be disposed against a surface of the base plate in which the receptacles are formed. The adhesive gasket may be constructed such that it engages portions of a frame of a membrane plate and/or another appropriate structure to help form separate isolated volumes between the interior surface of the hybridization plate and the one or more membranes such that each volume is in fluid communication with a separate receptacle of the base plate and the array contained therein. Each of these separate volumes are also fluidly coupled with at least one of the openings formed in the hybridization plate to permit the introduction of fluid to the individual receptacles for processing of the microwell arrays. FIG. 19 depicts another embodiment of the hybridization plate in which the hybridization plate is attached to a base plate using a mechanical interference fit such as tabs 728 which may engage with recesses formed in the base plate. In such an embodiment, the individual volumes may be formed by appropriate corresponding lips, gaskets, and/or any other appropriate structures present on either the hybridization plate and/or the membrane plate to form the above described isolated volumes associated with the separate receptacles and arrays as the disclosure is not so limited.

While specific embodiments of a hybridization plate and methods for attaching the hybridization plate to a base plate have been discussed above, it should be understood that the current disclosure is not limited to these particular constructions and methods. For example, a hybridization plate may be attached to a base plate using any appropriate method, including, but not limited to, threaded fasteners, clamps, adhesives, mechanical interference fits, and or any other appropriate technique as the disclosure is not limited in this fashion.

Figure 20B:
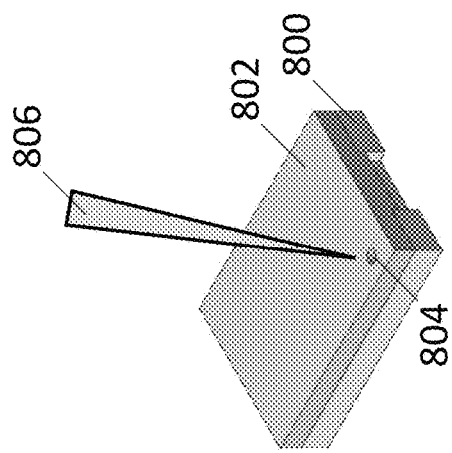
FIGS. 20A and 20B are schematic perspective views of hybridization chambers described herein.
Figure 20A:
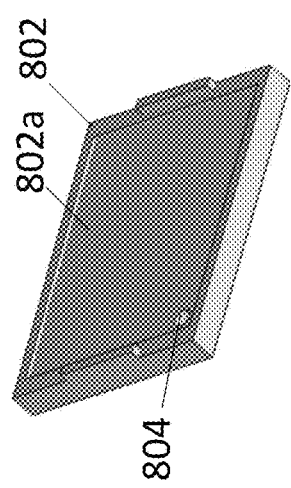

FIGS. 20A and 20B depict one embodiment for a device and method for sample collection. In the depicted embodiment, a hybridization chamber 800 is bonded onto a top surface of a microwell array 800 in which a plurality of microwells are formed. The hybridization chamber may be bonded to the array using any appropriate method and/or material. However, in some embodiments, it may be beneficial for the hybridization chamber to be bonded onto the array with a hydrophobic adhesive. Since the depicted hybridization chamber does not fully surround the array, the array may include a closed bottom surface such that the microwell arrays only extend partially through the array. The hybridization chamber may include an interior surface that forms an internal volume between an interior surface 802a of the hybridization chamber and the array. Fluids may be introduced by a pipette 806, or other appropriate fluid dispensing device, through an opening 804 that extends from an exterior surface to an interior surface of the hybridization chamber. Accordingly, samples may be injected into and initially processed using the depicted assembly.

Figure 21:
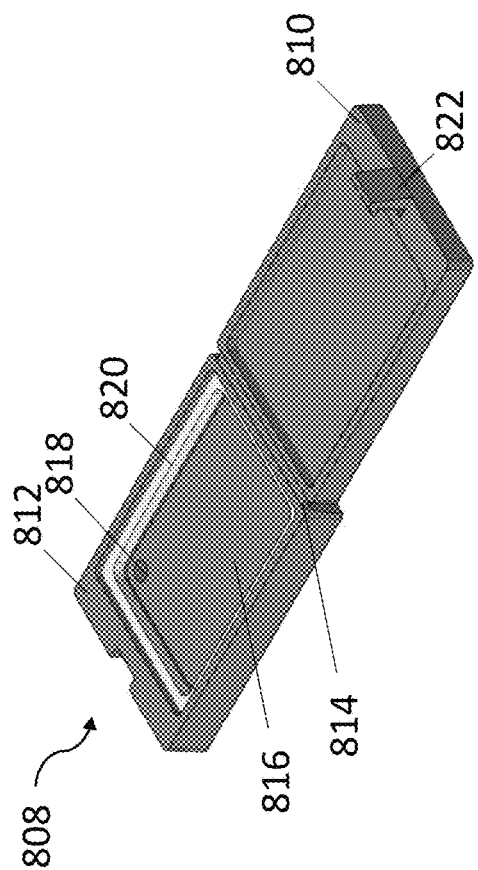
FIG. 21 is a schematic perspective view of another embodiment of a hybridization chamber.

FIG. 21 depicts another embodiment of a hybridization chamber 808. In this particular embodiment, the hybridization chamber includes a first body portion 810 and a second body portion 812. The first and second body portions are connected by a hinge 814 which may be any appropriate structure including both living hinges and separately formed hinges either attached to and/or overmolded into the body portions. An appropriate connector 822, such as the depicted tab and slot configuration, may be used to selectively retain the first and second body portions in a closed configuration against each other. The first and second body portions may include interior surfaces that are appropriately constructed to form a chamber 816 between the first and second body portions when they are in the closed configuration disposed against one another. The chamber may be sized and shaped to accept an array including a plurality of microwells. In some instances the microwells may extend completely through the array. The chamber may also include a gasket 820 surrounding a periphery of the chamber to seal the chamber when closed. Additionally, similar to the above embodiment, an opening 818 may be formed in either the first and/or second body portions in order to introduce and removed liquid from the chamber for initial sample processing.

Regardless of the specific hybridization chamber used, once an array has been appropriately placed into and/or bonded with a hybridization chamber, the array may be hydrated by introducing a desired buffer or other solution for a desired duration. The hybridization chamber may then be aspirated prior to introduction of appropriately buffered cells being introduced into the hybridization chamber through the chamber opening. The cells may remain in the hybridization chamber for an appropriate duration to ensure a majority, or substantially all, of the microwells of an array have received a cell therein. The hybridization chamber may then again be asperated and a buffered fixative may be introduced to the hybridization chamber. Depending on the particular application, the hybridization chamber may then be spun dry and/or a sticker, plug, or other seal may be placed into and/or on the opening of the hybridization chamber for subsequent use and processing of the biological samples (i.e. cells) held within the array.

Figure 22:
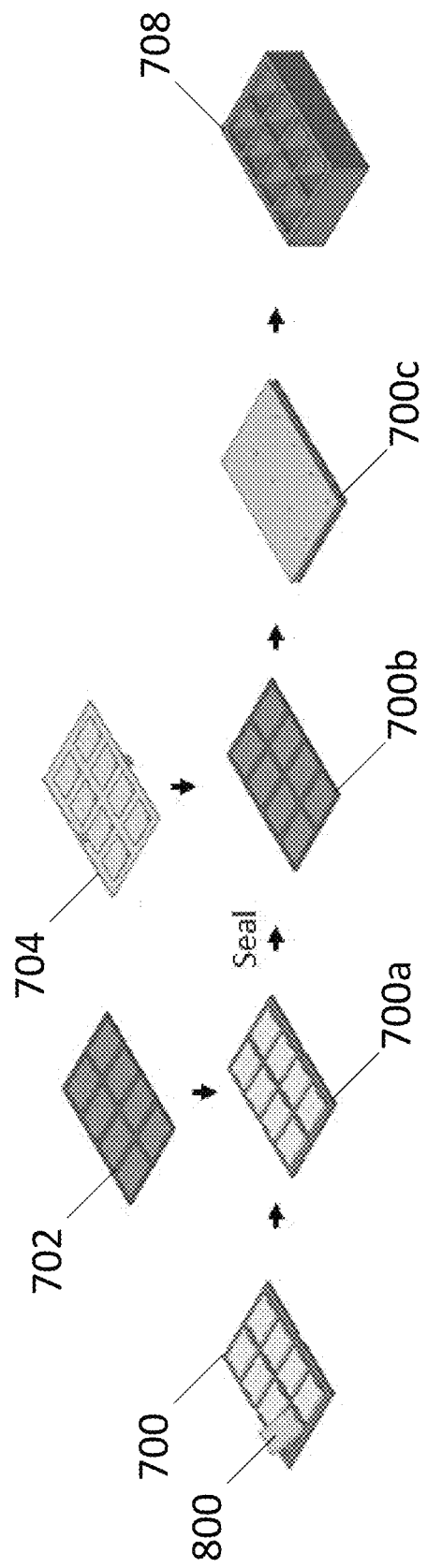
FIG. 22 is a schematic of workflow for processing a sample.

After a number of samples have been collected, it may be desirable to process multiple arrays at once. Such a process is illustrated in FIG. 22 using the previously described kit. Initially, a plurality of microwell arrays 800 may be loaded into the corresponding plurality of receptacals formed in a base plate 700 that is constructed and arranged to support the arrays. A separate membrane plate 702 may be assembled with the first assembly 700a of the base plate and arrays such that the one or more membranes of the membrane plate are disposed on the surface of the base plate including the receptacles the arrays are received in. In the assembled state the one or more membranes of the membrane plate may cover the plurality of receptacles and the arrays positioned therein. As previously described, the membrane plate may include appropriate structures for isolating the receptacles from each other to avoid fluid communication between the receptacles through the membrane plate. After being assembled, the membrane plate may be sealed onto the base plate to form a second assembly 700b. In some embodiments, the membrane plate may be sealed onto the base plate using a thermal press. However, embodiments in which other sealing methods are used are also contemplated. For example, instances in which base plates including receptacles formed by through-holes formed in the base plate, as described previously, may facilitate the use of vacuum sealing to attach and seal the membrane plate to the base plate. However, any appropriate attachment and/or sealing method may be used as the disclosure is not so limited.

As also illustrated in FIG. 22, the resulting second assembly 700b including the membrane plate sealed to the base plate may be subsequently assembled with a hybridization plate 704. Specifically, an interior surface of the hybridization plate may be positioned such that it is disposed on the second assembly with the membrane plate disposed between the hybridization plate interior surface and the base plate. As previously described, the hybridization plate may be constructed to form separate isolated volumes between the one or more membranes of the membrane plate and corresponding regions of the hybridization plate interior surface. Each of the separate isolated volumes may be in fluid communication with a separate individual receptacle of the base plate and the array disposed therein. The hybridization plate may be attached to the second assembly using any appropriate method to form a third assembly 700c.

Once the third assembly 700c is formed, any appropriate processing of the biological samples contained in the microwells of the arrays contained in the third assembly may be conducted. Specifically, various reactants, buffers, solvents, and/or any other desired materials may be input into the individual volumes and associated receptacles through openings formed in the hybridization plate. This may either be done manually and/or using an automated system as the disclosure is not so limited. For example, cell lysis, RNA hybridization, RT, exo, and S3 reactions may all be easily performed by injecting the desired materials into the isolated separate receptacles containing the arrays. The materials may then be aspirated from the system while the membrane prevents the biological materials retained in the arrays from leaving the system during processing. The next processing step may then be similarly performed until processing has been completed.

Once all processing of the biological materials in the microwells of the arrays have been completed, the hybridization plate and membrane plate may be removed from the assembly. The arrays 800, and in some embodiments the corresponding base plate 700, may be placed onto an associated collection plate 708. As described previously, the collection plate may include a plurality of recesses that are constructed and arranged to support the individual arrays and base plate such that each array, and associated receptacle of the base plate, are in fluid communication with a single recess of the collection plate. Accordingly, the assembly of the arrays, base plate, and collection plate may be centrifuged to spin out the biological materials contained in the plurality of microwells of the arrays into the recesses of the collection plate. In some embodiments the biological material contained in the microwells may be cellular fragments such as DNA and/or RNA fragments bonded with the microbeads though embodiments in which different biological materials are collected are also contemplated. Depending on the desired use, the collection plate may be sealed with an appropriate cover that is sized and shaped to seal the plurality of recesses of the collection plate for subsequent use and/or processing. Alternatively, the collected biological material may simply be collected from the recesses and used in any desired fashion.

EXAMPLES

Example 1—Seq-Well Second Stand Synthesis Protocol 0.1 M NaOH
TE—10 mM Tris, 1 mM EDTA pH 8.0
TE—0.5% SDS
TE—0.01% Tween
RT Reaction—No TSO
40 uL 5× Maxima buffer
80 uL 30% PEG8000
20 uL dNTPs
5 uL RNase Inhib
10 uL Maxima RT (Thermo)
45 uL water
$2^{nd}$ Strand Synthesis Reaction
40 uL 5× Maxima buffer
80 uL 30% PEG8000
20 uL dNTPs
2 uL dN-SMRT oligo (1 mM)
5 uL Klenow Exo—(NEB)
53 uL water

```
                                            (SEQ ID NO: 1)
dN-SMRT oligo - AAGCAGTGGTATCAACGCAGAGTGANNNGGNNNB
```

Beginning after $2^{nd}$ wash of TE-Tween after Exo treatment of standard Seq-well protocol 1) After aspiration of $2^{nd}$ TE-Tween wash, resuspend beads in 500 uL 0.1 M NaOH
2) Rotate tube for 5 min at room temp.
3) Spin and aspirate supernatant
4) Wash 1× in TE-Tween
5) Wash 1× in TE
6) Resuspend beads in 200 uL $2^{nd}$ strand synthesis reaction.
7) Rotate at 37 C for 1 hr
8) Wash beads 2× in TE-Tween
9) Wash 1× in TE
10) Resuspend beads in 200 uL of water
11) Count beads
12) Proceed to standard WTA protocol.

Example 2—Spatial Barcoding Protocol Sealing Picowell Array with Barcode Microarray Reagents
Spatial Barcode Microarray Extension
In situ synthesized microarray—80k features
    Each feature is 5'-$dT_{17}$-$SpatialBC_{10}$-CAACTCTGCGTT-GATACCACTG-3' (SEQ ID NO: 2)
Hyb Buffer—6×SSC, 10% formamide, 0.01% Tween20, 0.01 mg/mL BSA
Klenow exo- Rxn-1× Buffer 2, 30 uM dNTPs, 0.2 U/uL Klenow Exo—
    Optional: 6 uM Texas Red-5-dCTP to visualize extension product
20×SSC buffer

```
Primers
                                            (SEQ ID NO: 3)
SpatBC oligo /56-FAM//iAmMC6T/

AAGCAGTGGTATCAACGCAGAGTTG (HPLC purified)
```

0.1 M sodium bicarbonate buffer pH 8.5
NHS—S—S-biotin
Seq-Well Array Conjugation
standard chitosan/aspartate Seq-well nanowell array
EDC ((1-ethyl-3-(3-dimethylaminopropyl)carbodiimide hydrochloride)—(Thermo 22980)
NHS (N-Hydroxysuccinimide)—(Thermo)
BupH MES saline buffer pH 4.7 (Thermo 28390B)
PBS
Streptavidin (Biolegend)
60×25 lifter slip (Electron Microscopy Sciences)
Amplifying/Sequencing Spatial Barcode
Ampure beads (Beckman)
Klenow Exo—(NEB)
Kapa HiFi 2× Master mix (Kapa)

```
Primers
P5-TSO_Hybrid -
                                            (SEQ ID NO: 4)
AATGATACGGCGACCACCGAGATCTACACGCCTGTCCGCGGAAGCAGTGG

TATCAACGCAGAGT*A*C
```

```
SB_Nextera_Primer1 -
                                           (SEQ ID NO: 5)
GTCTCGTGGGCTCGGAGATGTGTATAAGAGACAGAAGCAGTGGTATCAAC

GCAGAGT*T*G

Nextera N7xx - (N701) -
                                           (SEQ ID NO: 6)
CAAGCAGAAGACGGCATACGAGATTCGCCTTAGTCTCGTGGGCTCGG Read1CustomSeqB -
                                           (SEQ ID NO: 7)
GCCTGTCCGCGGAAGCAGTGGTATCAACGCAGAGTAC
```

Equipment

60 C oven

Hybridization clamp (Agilent)

Protocol

Conjugating Oligo with Cleavable Biotin
1. Resuspend oligo in 0.1 M sodium bicarb buffer pH 8.5 to a concentration of 200 uM
2. Per 90 uL of oligo solution, measure 250 ug of NHS—S—S-Biotin in 1.5 mL tube.
3. Resuspend NHS-biotin in 10 uL DMSO
4. Quickly add the oligo solution to the biotin crosslinker.
5. Incubate in the dark >6 hr-ON. Lightly vortex every 30 min for first 2 hours.
6. While oligo conjugates, prepare desalting column by washing 2× with 300 uL of PBS by centrifuging at 1000×g for 1 min in between each wash.
7. After incubation, remove unreacted biotin by running reaction through dealting column, 100 uL/column Spatial Barcode Microarray Extension Typically performed on a slide washer
1. Wash 2 min 2×SSC
2. Inject 200 uL Hyb buffer
3. Hybridize 10 min
4. Wash 2×SSC
5. Inject 200 uL Hyb buffer+100 nM SPATBC oligo
6. Incubate 3 min 70 C
7. Incubate 1 hr 25 C
8. Wash 2×SSC
9. Wash 0.2×SSC
10. Inject 200 uL 1×Buffer2
11. Inject 200 uL Klenow reaction
12. Incubate 25 C for 30 min
13. Wash 2×SSC
14. Wash 0.2×SSC
15. Store in PBS for up to 5 days (probably much longer—do not dry)

Conjugation of Seq-Well Array with Anti-FITC Antibody
16. Wash array in 50 mL water in tip box
17. Wash array in 5 mL 1×MES buffer in 4 well dish
18. Submerge array in 5 mL of 10 mg/mL EDC, 1 mg/mL NHS in MES buffer in 4 well dish
19. Incubate for 30 min at RT
20. Wash array 2× in 50 mL water in tip box
21. Quickly wash 1× in 1×PBS in tip box
22. Add 200 uL of 50 ug/mL streptavidin in PBS on top of array
13) Optional: 5 ug/mL PE-streptavidin to visualize conjugated protein layer
23. Place lifter slip on array
24. Incubate for >15 hours at 4 C
25. Wash 2× in PBS Transfer Spatial Barcode
26. Wash Seq-well array and extended spatial barcode microarray in 0.1×PBS
27. Place Seq-well array in hybridization clamp
28. Lay microarray on top, array side down, making sure no bubbles get tramped underneath.
29. Seal array by tightening clamp
30. Incubate at 37 C for 30 min to improve seal
31. Remove clamp
32. Image array sandwich in transmitted light and FITC fluorescence channel to document relationship between spatial array and Seq-well array
33. While imaging, prepare boiling water bath
34. After imaging, place sandwich back in clamp
35. Transfer clamp to boiling water bath for 3 min
36. Transfer clamp to RT for 1 hr
37. Open clamp
38. Examine array under microscope—FITC signal should be filling entire well volume
39. If so, place array in 50 mL PBS and open sandwich
40. Quickly wash 2× in PBS in tip boxes
41. Array is spatially barcoded Load Cells Perform Functional Assays/Image Cytometry Perform Standard Seq-Well Capture Reaction Up to RT Step Amplifying and Sequencing Spatial Barcode
14)
42. Perform RT and ExoI steps according to Seq-well protocol.
43. WTA reaction is performed using the same PCR mix but is only amplified for 8 cycles (only necessary if large number of barcodes have been captured).

Purification of the cDNA Library
44. Let beads come to room temperature (30 minutes) and occasionally vortex for 5-10 seconds.
45. Pool your PCR reactions for one sample into 1.5 mL tube (For instance, if I run 7 PCR reactions for one sample (AKA one array), then I will pull those together for subsequent processing)
46. Add 0.6×volume of Ampure XP beads to the pooled PCR product
47. Incubate 5 minutes
48. Place tube in magnet stand. Allow beads to aggregate on magnet (~1-2 min)
49. Remove supernatant and place in clean tube
50. Add 400 uL of 80% ethanol to tube with beads
51. Add 1.4×volume Ampure beads to the removed supernatant Optional: To save on beads, can purify only a portion of the supernatant
52. Incubate for 5 min
53. Place on magnet. Allow beads to aggregate on magnet (~1-2 min)
54. Remove supernatant
55. Add 400 uL of 80% ethanol to supernatant tube
56. Rotate positions of all tubes on magnet 4× to make beads move through volume of the tube
57. Remove wash
58. Repeat steps 7-10
59. After removing second wash, close top of tube and place in centrifuge.
60. Spin at max speed for 10 s
61. Place tube back in magnet rack
62. Remove remaining liquid with 20 uL pipet
63. Incubate 5 min open to dry pellet (do not overshoot this much or beads will not resuspend well)
64. Remove tube from magnet rack
65. Add 15 uL of H$_2$O to each tube 66. Fully resuspend beads in water
67. Place back on magnet rack
68. Transfer supernatant to new PCR tube, discard tubes with beads.
69. Add 25 uL Kapa HiFi and 4 uM Seq-well WTA primer.
70. Finish amplification of WTA product with 8 more cycles.

Amplify Spatial Barcode

71. Dilute supernatant fraction 1:10, 1:100 and 1:1000, 1:10,000
72. Make 4 reactions of the following PCR mix
    25 uL 2× Kapa HiFi mix
    1 uL 40 uM P5-TSO_Hybrid
    1 uL 40 uM SB_Nextera_Primer1
    1 uL diluted supernatant fraction
    22 uL water
73. Amplify each dilution with the following program
PCR Program
15) 95 C 3 minutes
16) 15 cycles of:
17) 98 C 20 s
18) 67 C 20 s
19) 72 C 30 min
20) Then:
21) 4 C forever
74. Make 4 reactions of the 2$^{nd}$ PCR mix:
22) 25 uL 2× Kapa HiFi mix
23) 1 uL 40 uM P5-TSO_Hybrid
24) 1 uL 40 uM SB_Nextera N7xx
25) 1 uL PCR reaction 1
26) 22 uL water
75. Amplify each dilution with the following program
PCR Program
27) 95 C 3 minutes
28) 12 cycles of:
29) 98 C 20 s
30) 67 C 20 s
31) 72 C 30 min
32) Then:
33) 4 C forever
76. Purify reactions with 2× Ampure beads as described above
77. Analyze by BioAnalyzer
78. Select library that is not over-amplified (2-20 nM)
    a. Library should be clean ~230-240 bp peak
79. Sequence on MiSeq as follows
    Read 1-20 bp-Primer-Read1CustomSeqB
    Index 1-8 bp-Nextera standard
    Read 2-40 bp-Primer-Nextera standard Example 3—Spatial Barcoding Protocol Using Picowell Array Synthesized on Barcode Oligo Microarray Reagents
Spatial Barcode Microarray Functionalization
In situ synthesized microarray—80k features, not deprotected
Each feature is 5'-dT$_{17}$-SpatialBC$_{10}$-CAACTCTGCGTT-GATACCACTG-3' (SEQ ID NO: 2)
Acrydite phosphoramidite (0.1M in anhydrous acetonitrile)
3% Trichloroacetic acid (TCA) in dichloromethane (DCM)
0.3M BTT
0.1M iodine in THF/pyridine/water
Final Deprotect solution—Ethanolamine:Ethanol 1:1 solution Spatial Barcode Microarray Extension
Hyb Buffer—6×SSC, 10% formamide, 0.01% Tween20, 0.01 mg/mL BSA
Klenow exo- Rxn-1× Buffer 2, 30 uM dNTPs, 0.2 U/uL Klenow Exo—
    Optional: 6 uM Texas Red-5-dCTP to visualize extension product 20×SSC buffer

```
Primers
                                             (SEQ ID NO: 3)
SpatBC oligo /56-FAM/AAGCAGTGGTATCAACGCAGAGTTG (HPLC purified)
```

Picowell Array Surface Functionalization
0.2% chitosan in 0.1M acetic acid pH 6.0
1% BSA in PBS
Amplifying/Sequencing Spatial Barcode
Ampure beads (Beckman)
Klenow Exo—(NEB)
Kapa HiFi 2× Master mix (Kapa)

```
Primers
P5-TSO_Hybrid -
                                             (SEQ ID NO: 4)
AATGATACGGCGACCACCGAGATCTACACGCCTGTCCGCGGAAGCAGTGG

TATCAACGCAGAGT*A*C

SB_Nextera_Primer1 -
                                             (SEQ ID NO: 5)
GTCTCGTGGGCTCGGAGATGTGTATAAGAGACAGAAGCAGTGGTATCAAC

GCAGAGT*T*G

Nextera N7xx - (N701) -
                                             (SEQ ID NO: 6)
CAAGCAGAAGACGGCATACGAGATTCGCCTTAGTCTCGTGGGCTCGG Read1CustomSeqB -
                                             (SEQ ID NO: 7)
GCCTGTCCGCGGAAGCAGTGGTATCAACGCAGAGTAC
```

Equipment
60 C oven
Hybridization clamp (Agilent)
Protocol
Spatial Barcode Microarray Acryl Functionalization
1. Remove DMT from spatial barcode microarray still containing protecting groups on oligos by treating array with 500 uL TCA solution for 2 min
2. Wash with anhydrous DCM
3. Mix 250 uL BTT activation reagent and 250 uL Acrydite solution in anhydrous vial
4. Add to top microarray surface
5. Incubate for 10 min
6. Wash 2× with 5 mL acetonitrile
7. Submerge array in 4 mL iodine solution for 2 min
8. Wash 2× with acetonitrile
9. Wash 2× with ethanol
10. Submerge array in 5 mL final deprotect solution for 25 min in 65 C.
11. Wash 3× in ethanol
12. Wash 1× in acetone
13. Spin dry Spatial Barcode Microarray Extension
   Typically performed on a slide washer
   14. Wash 2 min 2×SSC
   15. Inject 200 uL Hyb buffer
   16. Hybridize 10 min
   17. Wash 2×SSC
   18. Inject 200 uL Hyb buffer+100 nM SPATBC oligo
   19. Incubate 3 min 70 C
   20. Incubate 1 hr 25 C
   21. Wash 2×SSC
   22. Wash 0.2×SSC
   23. Inject 200 uL 1×Buffer2
   24. Inject 200 uL Klenow reaction
   25. Incubate 25 C for 30 min
   26. Wash 2×SSC
   27. Wash 0.2×SSC
   28. Store in PBS for up to 5 days (probably much longer—do not dry)
Use 3D Stereolithography to Synthesize Picowell Array on Microarray Surface Using Acryl-Containing Resin
Functionalize Picowell Array Surface
   29. Submerge array in chitosan solution for 2 hours
   30. Wash 4× with water
   31. Submerge in BSA solution
   32. Place in vacuum chamber to hydrate picowells
   33. Incubate rocking overnight in vacuum chamber
   34. Place in PBS until just before using
   35. Transfer to RPMI+10% FBS (or equivalent media) just prior to cell loading
Load Cells
Perform Functional Assays/Image Cytometry
Perform Standard Seq-Well Capture Reaction Up to RT Step
   Lysis buffer will cause denaturation of double-stranded barcode. Released oligo will bind barcoded capture bead.
Amplifying and Sequencing Spatial Barcode
   34)
   36. Perform RT and ExoI steps according to Seq-well protocol.
   37. WTA reaction is performed using the same PCR mix but is only amplified for 8 cycles (only necessary if large number of barcodes have been captured).
   Purification of the cDNA Library
   38. Let beads come to room temperature (30 minutes) and occasionally vortex for 5-10 seconds.
   39. Pool your PCR reactions for one sample into 1.5 mL tube (For instance, if I run 7 PCR reactions for one sample (AKA one array), then I will pull those together for subsequent processing)
   40. Add 0.6×volume of Ampure XP beads to the pooled PCR product
   41. Incubate 5 minutes
   42. Place tube in magnet stand. Allow beads to aggregate on magnet (~1-2 min)
   43. Remove supernatant and place in clean tube
   44. Add 400 uL of 80% ethanol to tube with beads
   45. Add 1.4×volume Ampure beads to the removed supernatant
   Optional: To save on beads, can purify only a portion of the supernatant
   46. Incubate for 5 min
   47. Place on magnet. Allow beads to aggregate on magnet (~1-2 min)
   48. Remove supernatant
   49. Add 400 uL of 80% ethanol to supernatant tube
   50. Rotate positions of all tubes on magnet 4× to make beads move through volume of the tube
   51. Remove wash
   52. Repeat steps 7-10
   53. After removing second wash, close top of tube and place in centrifuge.
   54. Spin at max speed for 10 s
   55. Place tube back in magnet rack
   56. Remove remaining liquid with 20 uL pipet
   57. Incubate 5 min open to dry pellet (do not overshoot this much or beads will not resuspend well)
   58. Remove tube from magnet rack
   59. Add 15 uL of $H_2O$ to each tube
   60. Fully resuspend beads in water
   61. Place back on magnet rack
   62. Transfer supernatant to new PCR tube, discard tubes with beads.
   63. Add 25 uL Kapa HiFi and 4 uM Seq-well WTA primer.
   64. Finish amplification of WTA product with 8 more cycles.
Amplify Spatial Barcode
   65. Dilute supernatant fraction 1:10, 1:100 and 1:1000, 1:10,000
   66. Make 4 reactions of the following PCR mix
      25 uL 2× Kapa HiFi mix
      1 uL 40 uM P5-TSO_Hybrid
      1 uL 40 uM SB_Nextera_Primer1
      1 uL diluted supernatant fraction
      22 uL water
   67. Amplify each dilution with the following program
   PCR Program
      35) 95 C 3 minutes
      36) 15 cycles of:
      37) 98 C 20 s
      38) 67 C 20 s
      39) 72 C 30 min
      40) Then:
      41) 4 C forever
   68. Make 4 reactions of the $2^{nd}$ PCR mix:
      42) 25 uL 2× Kapa HiFi mix
      43) 1 uL 40 uM P5-TSO_Hybrid
      44) 1 uL 40 uM SB_Nextera N7xx
      45) 1 uL PCR reaction 1
      46) 22 uL water
   69. Amplify each dilution with the following program
   PCR Program
      47) 95 C 3 minutes
      48) 12 cycles of:
      49) 98 C 20 s
      50) 67 C 20 s
      51) 72 C 30 min
      52) Then:
      53) 4 C forever
   70. Purify reactions with 2× Ampure beads as described above
   71. Analyze by BioAnalyzer
   72. Select library that is not over-amplified (2-20 nM)
      a. Library should be clean ~230-240 bp peak
   73. Sequence on MiSeq as follows
      Read 1-20 bp-Primer-Read1CustomSeqB
      Index 1-8 bp-Nextera standard
      Read 2-40 bp-Primer-Nextera standard Example 4—Scalable Method for Making Templated Porous Membranes with Micron-Sized Features Using Dry Film Photoresist Laminates Scalable manufacture of microfluidic devices is currently challenging to achieve. Most research grade devices are manufactured by replica molding microfluidic components etched into silicon wafers or photoresist with polydimethylsiloxane (PDMS) polymer in molds. PDMS has several properties that make it suitable for microfluidic devices including elasticity, optical clarity and ease of use. However, scaling manufacture of PDMS devices is notoriously difficult due to the long cure time, short pot life and viscosity of the material. Typically, for large scale manufacture of microfluidic devices other systems are co-opted including micro-injection molding of thermoplastics or etching fluidic components directly in glass. However, these techniques are not widely available and have limits on the geometries that can be produced. Furthermore, they cannot produce elastomeric devices or devices with through-holes while maintaining a thin device. A new approach provided herein has been developed for scalable production of microfluidic features that can be leveraged to make standard elastomeric devices at scale at low cost and can be used to make new device (e.g., array) forms including filter plates for single cell analysis.

The approach described herein leverages dry films of photoresists to manufacture final microfluidic features directly in the photoresist using membrane roll-to-plate manufacturing processes using photolithographic processes. In traditional microfluidic device manufacture in research or at scale, liquid photoresist is spin coated onto a substrate, typically silicon wafers. A photolithographic mask and UV-exposure is then used to make the features in the photoresist. The photomask defines the pore geometries and spacing. The features in the developed photoresist are then either replicated (using PDMS or nickel for microinjection molding) or used as a mask to etch the features into the underlying substrate (glass microfluidics). In the process described herein, instead of spin coating liquid photoresist, pre-manufactured dry films of a photoresist is used, and such dry films can be purchased in bulk (in rolls of 100 m or more). The dry film is laminated directly to a photomask without an underlying substrate, exposed to UV light, and developed, generating microfluidic features in the film. Due to the low cost and scale of the dry films, the features in the photoresist can be used as the final fluidic features. The method does not require expensive and technically challenging replication of the microfeatures. This process can be done in a heated membrane roll-to-plate process with an added UV-light source, enabling the manufacture of material for 1000s of devices each day using standard industrial membrane processes.

Another major advantage is that, by the nature of the whole film being the photoresist, the microfluidic features become through-holes in the film, making the resulting product a highly engineered porous bottomless microwell array designed by light. Through-holes are notoriously challenging to create using any microfluidic manufacturing process even at small scale. The process described herein manufactures through-holes without significant effort. Another advantage is multiple photoresist films can be exposed separately and laminated on top of each other to generate complex 3D geometries. Finally the films come pre-made in about a variety of thicknesses including for example from 5-500 micron, making it extremely easy to control the thickness of the features, which has been a problem with traditional spin coating.

The engineered bottomless microwell arrays have been used to generate single cell analytical devices in various forms. In one example, the bottomless microwell arrays can be bonded to standard acrylic plastic sheets and laser cut to make hard plastic devices at similar cost and scale as micro-injection molding but with far less upfront tooling and cost. Moreover, this approach can be extended to incorporate biologic functionality at the bottom of the microfluidic features. For example, devices have been made in which the dry film photoresist with through-holes is bonded to DNA microarrays to place known DNA sequences in each nanowell for the spatial barcoding technique disclosed herein. In another example, the bottomless microwell arrays can be bonded to elastomer silicone sheets to make elastomeric devices where the walls of the microfluidic features are the photoresist but the top and bottom are elastic, thereby regaining the advantages of PDMS but maintaining scalability and low cost.

In yet another example, a device is created by bonding the engineered bottomless microwell arrays to a commercial membrane with much smaller pores (e.g., 80-200 nm), creating a filter that allows flux through the microfluidic features. As an example, a 24-well filter plate with 45 micron wells arrayed in the photoresist bonded to a 200 nm pore membrane was made. This allowed cells to be loaded into the wells through vacuum, as well as the attachment of a semiporous membrane to the top surface after cell loading via suction. This dramatically increased the usability of nanowell arrays including for genomic research.

Figure 11A:
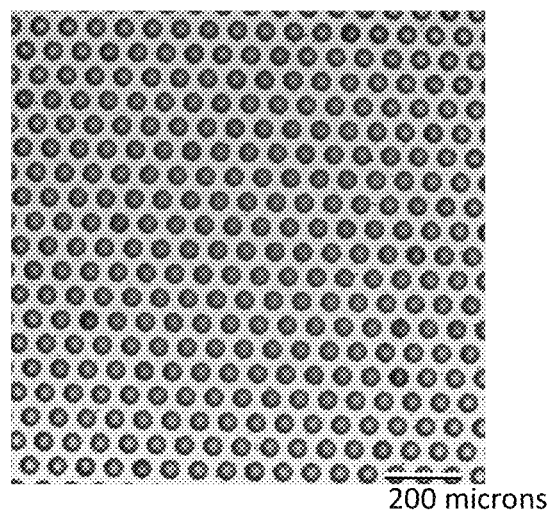
FIGS. 11A and 11B are images dry film of photoresist having through-holes.
Figure 11B:
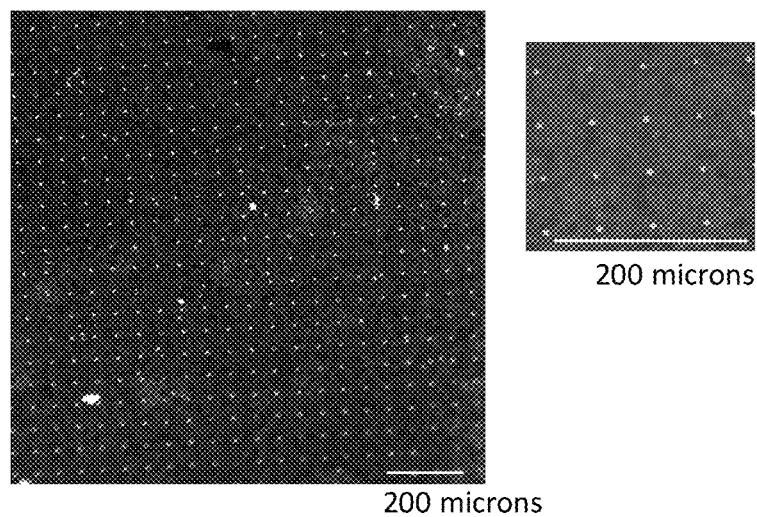
Figure 13A:
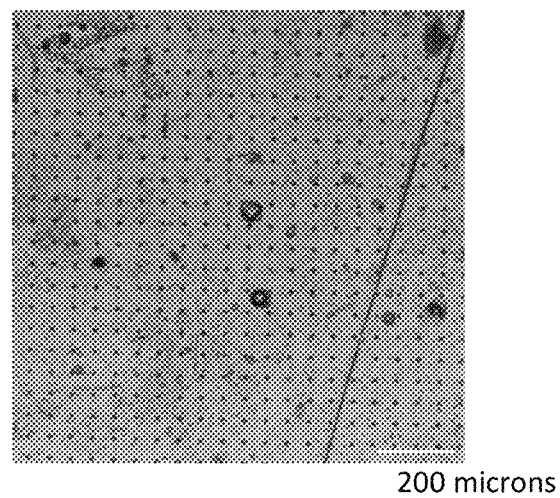
FIG. 13A and FIG. 13B are images of cell loaded arrays.
Figure 13B:
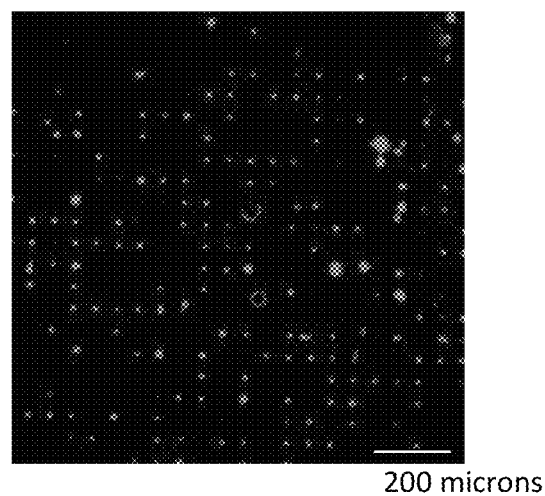

Exemplary configurations are shown in FIGS. 10A and 10B. FIGS. 11A and 11B show exemplary arrays with 50 micron and 5 micron pore sizes (in diameter) respectively. FIGS. 13A and 13B shows an exemplary loaded array. A double layer array was made by bonding two engineered photoresists with a commercial membrane. Exemplary double layer configurations are shown in FIGS. 10C and 10D and loaded configurations are shown in FIGS. 12A and 12B. The engineered arrays had well sizes of 7 micron and 45 micron and the spacing of the wells was designed such that only one 7 micron hole can overlap any given 45 micron hole. When cells are loaded into this engineered array via suction, only a single cell can fit into the small holes which subsequently blocks the suction force into the greater 45 micron well structure, thereby enabling directed cell loading of a single cell into each 45 micron well that overlapped a 10 micron well.

Directed cell loading is a major advance in single cell genomics which typically achieves single cell resolution through Poisson loading of wells or droplets, which unfortunately also means a single cell is loaded in only ~1 out of every ten wells or droplets, wasting 90% of the reagents and surface area of a device. Directed cell loading has the ability to increase by an order of magnitude the number of cells that can be analyzed in a device at the same cost.

FURTHER EMBODIMENTS

Additional, non-limiting, embodiments of this disclosure are as follows:
1. An array of wells comprising:
a first porous membrane having a flux rate of 0.1-100 mL/min/cm$^2$ and/or a pore size of 50 nm-3 microns; and
a first bottomless microwell array comprising a dry film of photoresist having a first plurality of through-holes;
wherein the first porous membrane contacts the first bottomless microwell array at the bottom surface of the first bottomless microwell array;
and wherein each well of the array comprises one of the first plurality of through-holes and a bottom surface comprising the first porous membrane.
2. The array of wells of embodiment 1, wherein the array further comprises a second porous membrane that contacts the first dry film of photoresist at the top surface of the first dry film of photoresist.

3. The array of wells of embodiment 2, wherein the second porous membrane is an ultrafiltration membrane.
4. The array of wells of embodiment 3, wherein the ultrafiltration membrane has an average pore diameter in the range of 1 nm and 200 nm.
5. The array of wells of any of the preceding embodiments, wherein the first dry film of photoresist is bonded to the first porous membrane.
6. The array of wells of any of the preceding embodiments, wherein the wells of the first bottomless microwell array have a pitch in a range of 20 microns to 200 microns.
7. The array of wells of any of the preceding embodiments, wherein the wells of the first bottomless microwell array have a uniform depth in a range of 5 microns to 500 microns.
8. The array of wells of any of the preceding embodiments, wherein the wells of the first bottomless microwell array are cylindrical and have a uniform diameter in the range of 1 microns to 500 microns (e.g., 15-100 microns or 1-10 microns).
9. The array of wells of any of embodiments 1-7, wherein the wells of the first bottomless microwell array are cuboid and have a uniform largest lateral length in a range of 1 micron-500 microns (e.g., 15-100 microns or 1-10 microns).
10. The array of wells of any of embodiments 1-7, wherein the wells of the first bottomless microwell array are conical and have a uniform diameter in a range of 35 microns to 100 microns at the top surface and have a uniform diameter in a range of 0.5 microns to 3 microns at the bottom surface.
11. The array of wells of embodiment 10, wherein the wells of the first bottomless microwell array have a uniform depth in a range of 30 microns to 100 microns.
12. The array of wells of any of the preceding embodiments, wherein the wells of the first bottomless microwell array have a largest lateral dimension in a range of 1 to 6 times the largest lateral dimension of a cell and/or bead.
13. The array of wells of any of the preceding embodiments, wherein the wells of the first bottomless microwell array have a largest lateral dimension in a range of 1 to 6 times the largest lateral dimension of a cell.
14. The array of wells of any of the preceding embodiments, wherein the wells of the first bottomless microwell array have a largest lateral dimension in a range of 1 to 6 times the largest lateral dimension of a bead.
15. The array of wells of any of the preceding embodiments, wherein the first dry film of photoresist is directly contacted to the first porous membrane.
15. The array of wells of any of the preceding embodiments, wherein the total lateral area of the wells at the top surface of the first dry film of photoresist is at least 10% of the total lateral area of the first dry film of photoresist.
16. The array of wells of any of the preceding embodiments, wherein the array further comprises a second bottomless microwell array.
17. The array of wells of embodiment 16, wherein the second bottomless microwell array comprises a second dry film of photoresist over the first dry film of photoresist having a second plurality of through-holes.
18. The array of wells of embodiment 16 or 17, wherein the array further comprises a second porous membrane over the second bottomless microwell array.
19. The array of wells of embodiment 18, wherein the second porous membrane is directly contacted to the second bottomless microwell array.
20. The array of wells of any of embodiments 16-19, wherein the wells of the first bottomless microwell array have a uniform diameter in the range of 1 micron to 10 microns.
21. The array of wells of any of embodiments 16-20, wherein the wells of the second bottomless microwell array have a uniform diameter in the range of 15 microns to 100 microns.
22. The array of wells of any of embodiments 16-21, wherein the second bottomless microwell array is directly contacted to the first bottomless microwell array.
23. The array of wells of any of embodiments 16-19, wherein the wells of the first bottomless microwell array have a uniform diameter in the range of 15 microns to 100 microns.
24. The array of wells of any of embodiments 16-19 or 23, wherein the wells of the second bottomless microwell array have a uniform diameter in the range of 1 micron to 10 microns.
25. The array of wells of any of embodiments 16-24, wherein the array further comprises a third porous membrane between the first bottomless microwell array and the second bottomless microwell array.
26. The array of wells of embodiment 25, wherein the third porous membrane is directly contacted to the first bottomless microwell array and/or the second bottomless microwell array.
27. The array of wells of any of embodiments 16-26, wherein the total lateral area of the wells at the top surface of the second dry film of photoresist is at least 10% of the total lateral area of the second dry film of photoresist.
29. The array of wells of any of embodiments 16-27, wherein the wells of the first and/or second dry film of photoresist have a maximum pitch of 2 mm.
30. The array of wells of any of the preceding embodiments, wherein the array further comprises one or more cells.
31. The array of wells of any of the preceding embodiments, wherein the array further comprises one or more beads.
32. A dry film of photoresist comprising a first array of wells having a largest lateral dimension in the range of 15-100 microns and having a porous bottom having a flux rate of 0.1-100 mL/min/cm$^2$ and/or a pore size of 50 nm-3 microns.
33. The dry film of photoresist of embodiment 32, wherein the porous bottom comprises a first porous membrane.
34. The dry film of photoresist of embodiment 32 or 33, the dry film of photoresist further comprises a second porous membrane that contacts the top surface of the first dry film of photoresist.
35. The dry film of photoresist of any of embodiments 32-34, wherein the dry film of photoresist is bonded to the first porous membrane.
36. The dry film of photoresist of any of embodiments 32-35, wherein the dry film of photoresist has a pitch in a range of 20 microns to 200 microns.
37. The dry film of photoresist of any of embodiments 32-36, wherein the wells of the dry film of photoresist have a maximum pitch of 2 mm.
38. The dry film of photoresist of any of embodiments 32-37, wherein the wells have a uniform depth in a range of 5 microns to 500 microns.
39. The dry film of photoresist of any of embodiments 32-38, wherein the wells are cylindrical have a uniform diameter in a range of 1 micron to 500 microns (e.g., 15-100 microns or 1-10 microns).
40. The dry film of photoresist of any of embodiments 32-38, wherein the wells are cuboid and have a largest lateral length in a range of 1 micron to 500 microns (e.g., 15-100 microns or 1-10 microns).
41. The dry film of photoresist of any of embodiments 32-38, wherein the wells are conical and have a uniform diameter in a range of 35 microns to 100 microns at the top surface and have a uniform diameter in a range of 0.5 microns to 3 microns at the bottom surface.

42. The dry film of photoresist of embodiment 41, wherein wells have a uniform depth of 30 microns to 100 microns.

43. The dry film of photoresist of any of embodiments 32-42, wherein the total lateral area of the wells at the top surface of the dry film of photoresist is at least 10% of the total lateral area of the dry film of photoresist.

44. A microfluidic device comprising a first bottomless microwell array having a largest lateral dimension in the range of 1-500 microns, bonded to (a) a second bottomless microwell array having a largest lateral dimension in the range of 1-500 microns, and (b) a first porous membrane.

45. The microfluidic device of embodiment 44, wherein the wells of the first bottomless microwell array have a largest lateral dimension in the range of 1-10 microns and the wells of the second bottomless microwell array have a largest lateral dimension in the range of 15-100 microns.

46. The microfluidic device of embodiment 45, wherein the wells of the first bottomless microwell array have a pitch in a range of 20 microns to 200 microns.

47. The microfluidic device of embodiments 45 or 46, wherein the wells of the second bottomless microwell array have a pitch in a range of 10 microns to 200 microns.

48. The microfluidic device of embodiment 44, wherein the wells of the first bottomless microwell array have a largest lateral dimension in the range of 15-100 microns and the wells of the second bottomless microwell array have a largest lateral dimension in the range of 1-10 microns.

49. The microfluidic device of embodiment 48, wherein the wells of the first bottomless microwell array has a pitch in a range of 10 microns to 200 microns.

50. The microfluidic device of embodiment 48 or 49, wherein the wells of the second bottomless microwell array has a pitch in a range of 20 microns to 200 microns.

51. The microfluidic device of any of embodiments 44-50, wherein the wells of the first and second bottomless microwell array have a maximum pitch of 2 mm.

52. The microfluidic device of any of embodiments 44-51, wherein the total lateral area of the wells at the top surface of the first bottomless microwell array is at least 10% of the total lateral area of the first bottomless microwell array.

53. The microfluidic device of any of embodiments 44-52, wherein the total lateral area of the wells at the top surface of the second bottomless microwell array is at least 10% of the total lateral area of the second bottomless microwell array.

54. The microfluidic device of any of embodiments 44-53, wherein the wells are cylindrical.

55. The microfluidic device of any of embodiments 44-53, wherein the wells are cuboid.

56. The microfluidic device of any of embodiments 44-53, wherein the wells of the array are conical.

57. The microfluidic device of any of embodiments 44-56, wherein each of at least 90% of the wells of the first bottomless microwell array is in fluid communication with a single well of the second bottomless microwell array.

58. The microfluidic device of any of embodiments 44-57, wherein the first and or second bottomless microwell array comprise a dry film of photoresist.

59. The microfluidic device of any of embodiments 44-58, wherein the microfluidic device further comprises a second porous membrane that contacts the top surface of the second bottomless microwell array.

60. The microfluidic device of any of embodiments 44-59, wherein the first bottomless microwell array is bonded to the first porous membrane.

61. The microfluidic device of any of embodiments 44-60, wherein the wells of first bottomless microwell array have a uniform depth in a range of 5 microns to 500 microns.

62. The microfluidic device of any of embodiments 44-61, wherein the microfluidic device further comprises a third porous membrane situated between the first and second bottomless microwell array.

63. The microfluidic device of embodiment 62, wherein the second bottomless microwell array is bonded to a third porous membrane.

64. The array of wells, dry film of photoresist, or microfluidic device of any of the preceding embodiments, wherein wells are configured to capture a single cell and/or bead.

65. The array of wells, dry film of photoresist, or microfluidic device of any of the preceding embodiments, wherein the wells are arranged in a hexagonal pattern 66. The array of wells, dry film of photoresist, or microfluidic device of any of the preceding embodiments, wherein the first porous membrane has an average pore size in a range of 1 nm to 1000 nm. (e.g., 80 nm to 200 nm)

67. The array of wells, dry film of photoresist, or microfluidic device of any of the preceding embodiments, wherein the first porous membrane has an average pore size in a range of 0.001 to 0.25 times a largest lateral dimension of a cell and/or bead.

68. The array of wells, dry film of photoresist, or microfluidic device of any of the preceding embodiments, wherein the first porous membrane has an average pore size in a range of 0.001 to 0.1 times a largest lateral dimension of a cell.

69. The array of wells, dry film of photoresist, or microfluidic device of any of the preceding embodiments, wherein the first porous membrane has an average pore size in a range of 0.001 to 0.1 times a largest lateral dimension of a bead.

70. The array of wells, dry film of photoresist, or microfluidic device of any of the preceding embodiments, wherein the second porous membrane is an ultrafiltration membrane.

71. The array of wells, dry film of photoresist, or microfluidic device of embodiment 70, wherein the ultrafiltration membrane has an average pore diameter in the range of 1 nm and 200 nm.

72. The array of wells, dry film of photoresist, or microfluidic device of any of the preceding embodiments, wherein the third porous membrane has an average pore size in a range of 1 nm to 1000 nm. (e.g., 80 nm to 200 nm)

73. A method of making a free standing photoresist film comprising a plurality of through-holes, comprising:
    aligning a first dry film of photoresist with a photomask;
    exposing at least a portion of the first dry film of photoresist to ultraviolet (UV) light through the photomask to form a plurality of first through-holes in the first dry film of photoresist, thereby producing a first free standing photoresist film comprising a plurality of through-holes.

73a. The method of embodiment 73, wherein the first free standing photoresist film comprising a plurality of through-holes comprises a first bottomless microwell array.

73a. The method of embodiment 73 or 73a, wherein the method further comprises contacting the bottomless microwell with a base layer to form an array of wells, wherein the first dry film of photoresist is not supported by a substrate.

74. The method of any of embodiments 73-73b, wherein base layer comprises a first porous membrane.

75. The method of embodiment 74, wherein the method further comprises loading beads into the array of wells.

76. The method of any of embodiments 73-75, wherein the method further comprises contacting the first bottomless microwell array or the array of wells, at its top surface, with a second porous membrane.

77. The method of embodiment 76, wherein the method further comprises contacting (e.g., bonding, heat laminating) the second porous membrane, at its exposed surface, with a second bottomless microwell array.

78. The method of any of embodiments 73-75, wherein the method further comprising contacting the first bottomless microwell array, at its top surface, with a second bottomless microwell array.

79. The method of embodiment 78, wherein the method further comprising heat laminating the first bottomless microwell array with to the bottomless microwell array with the second bottomless microwell array.

80. The method of any of embodiments 73-79, wherein the second bottomless microwell array is produced by:
    aligning a second dry film of photoresist with a second photomask;
    exposing at least a portion of the second dry film of photoresist to UV light through the second photomask to form a plurality of second through-holes in the second dry film of photoresist, thereby producing a second bottomless microwell array.

81. The method of embodiment 80, further comprising randomly aligning the first bottomless microwell array with the second bottomless microwell array.

82. The method of embodiment 80 or 81, wherein exposing the at least one portion of the first dry film of photoresist to UV light through the photomask comprises directing the UV light at an angle in a range of 0 degrees to 45 degrees from a direction normal to a surface of the first dry film of photoresist such that first microwells of the first bottomless microwell array are conical in shape.

83. The method of any of embodiments 73a-82, wherein the wells of the first bottomless microwell array have a pitch in a range of 20 microns to 200 microns.

84. The method of any of embodiments 73a-83, wherein the first and/or second bottomless microwell array has a thickness in a range of 5 microns to 500 microns.

85. The method of any of embodiments 73a-84, wherein the wells have a largest and/or smallest lateral dimension in a range of 5 microns to 500 microns. (e.g., 45 microns, 7 microns, 10 microns)

86. The method of any of embodiments 73a-85, wherein the wells of the first bottomless microwell array have a largest lateral dimension in a range of 1-10 microns and the wells of the second bottomless microwell array have a largest lateral dimension in a range of 15-100 microns.

87. The method of embodiment 86, wherein the wells of the first bottomless microwell array has a pitch in a range of 20 microns to 200 microns.

88. The method of embodiment 86 or 87, wherein the wells of the second bottomless microwell array has a pitch in a range of 10 microns to 200 microns.

89. The method of any of embodiments 73a-88, wherein the wells of the first bottomless microwell array have a largest lateral dimension in a range of 15-100 microns and the wells of the second bottomless microwell array have a largest lateral dimension in a range of 1-10 microns.

90. The method of embodiment 89, wherein the wells of the first bottomless microwell array have a pitch in a range of 10 microns to 200 microns.

91. The method of embodiment 89 or 90, wherein the wells of the second bottomless microwell array has a pitch in a range of 20 microns to 200 microns.

92. The method of any of embodiments 73-91, wherein the photomask comprises a polymer.

93. The method of embodiment 92, wherein the photomask comprises polyethylene terephthalate (PET).

94. The method of any of embodiments 73-93, wherein the photomask comprises wells with a maximum pitch of 2 mm between any two adjacent wells.

95. The method of any of embodiments 73-94, wherein the photomask comprises features every 2 mm or less in any direction along a surface of the photomask.

96. The method of embodiment 95, wherein the features on the photomask occupy at least 10% of the area of the photomask and at most 99.9% of the area of the photomask (e.g., 50%).

97. The method of any of embodiments 73b-96, wherein the base layer comprises a plastic sheet.

98. The method of embodiment 97, wherein the plastic sheet comprises an acrylic plastic sheet.

97. The method of any of embodiments 73b-96, wherein the base layer comprises a DNA microarray.

100. The method of any of embodiments 73b-96, wherein the base layer comprises a silicone elastomer sheet.

101. The method of embodiment 100, wherein the silicone elastomer sheet comprises polydimethylsiloxane (PDMS).

102. The method of any of embodiments 7b3-96, wherein the base layer comprises a porous membrane.

103. The method of embodiment 102, wherein the porous membrane has a flux rate of 0.1-100 mL/min/cm$^2$ and/or a pore size of 50 nm-3 microns.

104. The method of any of embodiments 73-103, further comprising laminating a surface of the first dry film of photoresist directly to the photomask, optionally without an underlying support.

105. The method of embodiment 104, further comprising removing a release-liner (e.g., a polyolefin release-liner) from a surface of the first and/or second dry film of photoresist.

106. The method of embodiment 105, further comprising removing the release-liner immediately prior to lamination.

107. The method of any of embodiments 104-106, wherein laminating the surface of the first and/or second dry film of photoresist directly to the first and/or second photomask involves contacting the surface of the first and/or second dry film of photoresist with a surface of the first and/or second photomask; and
    exposing the first and/or second dry film of photoresist and the first and/or second photomask to a temperature in a range of 60 degrees Celsius to 80 degrees Celsius (e.g., 65 degrees Celsius) for a duration sufficient to bond the surface of the first and/or second dry film of photoresist to the surface of the first and/or second photomask.

108. The method of any of embodiments 104-107, wherein laminating the surface of the first and/or second dry film of photoresist directly to the first and/or second photomask involves heat-laminating the first and/or second dry film of photoresist directly to the first and/or second photomask at a rate in a range of 0.1 m/min to 0.5 m/min (e.g., 0.3048 m/min=1 ft/min)

109. The method of any of embodiments 73-108, wherein the at least one portion of the first and/or second dry film of photoresist is exposed to ultraviolet (UV) light through the first and/or second photomask for a period of time in a range of 1 min to 10 min (e.g., 2.5 min).

110. The method of any of embodiments 73-109, further comprising exposing the first and/or second dry film of photoresist and the first and/or second photomask to a temperature in a range of 80 degrees Celsius to 100 degrees Celsius (e.g., 95 degrees Celsius) for a duration sufficient to crosslink the at least one portion of the first and/or second dry film of photoresist that was exposed to UV light through the first and/or second photomask.

111. The method of any of embodiments 73-110, further comprising exposing the first and/or second dry film of photoresist and the first and/or second photomask to a temperature in a range of 80 degrees Celsius to 100 degrees Celsius (e.g., 95 degrees Celsius) for a period of time in a range of 1 min and 30 min (e.g., 15 min).

112. The method of any of embodiments 73-111, further comprising the method further comprising exposing the first and/or second dry film of photoresist and the first and/or second photomask to a temperature in a range of 15 degrees Celsius to 25 degrees Celsius (e.g., 20 degrees Celsius) for a duration sufficient to cool the first and/or second dry film of photoresist and the first and/or second photomask to the temperature.

113. The method of embodiment 112, wherein the first and/or second dry film of photoresist and the first and/or second photomask are exposed to a temperature in a range of 15 degrees Celsius to 25 degrees Celsius (e.g., 20 degrees Celsius) for a period of time in a range of 30 min to 90 min (e.g., 60 min).

114. The method of any of embodiments 73-113, further comprising exposing the first and/or second dry film of photoresist and the first and/or second photomask to a developing solution for a duration sufficient to remove any non-crosslinked portions of the first and/or second dry film of photoresist from the first and/or second dry film of photoresist.

115. The method of embodiment 114, wherein the first and/or second dry film of photoresist and the first and/or second photomask is exposed to a developing solution for a period of time in a range of 10 min and 30 min (e.g., 20 min).

116. The method of embodiment 114 or 115, wherein the developing solution comprises a developing solvent (e.g., cyclohexanol, cyclohexanone).

117. The method of any of embodiments 73-116, wherein the method further comprises de-laminating the first and/or second dry film of photoresist from the photomask in the developing solution.

118. The method of any of embodiments 73-118, further comprising washing the developed first and/or second dry film of photoresist.

119. The method of embodiment 119, wherein the developed first and/or second dry film of photoresist is washed in isopropanol for a duration sufficient to remove residual developing solution from the first and/or second dry film of photoresist.

120. The method of embodiment 118 or 119, —the method comprising washing the developed first and/or second dry film of photoresist in isopropanol for a period of time in a range of 1 min to 10 min (e.g., 5 min).

121. The method of any of embodiments 73-120, further comprising air drying the developed first and/or second dry film of photoresist.

122. The method of any of embodiments 73-121, further comprising bonding (e.g., by adhesive, by heat lamination) the base layer to the bottom surface of the first free standing photoresist film comprising a plurality of through-holes (e.g., the first bottomless microwell array).

123. The method of embodiment 122, wherein the base layer is laminated to the bottom surface of the first bottomless microwell array. (e.g., in embodiments where the base layer comprises a porous membrane)

124. The method of any of embodiments 73b-123, the method further comprising enclosing the first bottomless microwell array and the base layer in a housing.

125. The method of embodiment 124, wherein the housing comprises polystyrene.

126. A method, comprising:
 flowing a first fluid comprising a plurality of cells and/or a plurality of beads through:
  (i) the array of wells of any one of embodiments 1-31 or 64-72;
  (ii) the dry film of photoresist of any one of embodiments 32-43 or 64-72; or
  (iii) the microfluidic device of any one of embodiments 44-72,
 thereby forming a cell-loaded and/or a bead-loaded microwell array.

126a. The method of embodiment 126, wherein the cell-loaded array is super-poisson loaded.

127. The method of embodiment 126 or 126a, wherein the bead-loaded array is super-Poisson loaded.

128. The method of any of embodiments 126-127, wherein flowing the first liquid comprises flowing liquid through the array at a flow rate of 0.1-10 mL/min.

129. The method of any of embodiments 126-128, wherein the first liquid is flowed through the array at room temperature.

130. The method of any of embodiments 126-129, wherein the first liquid is flowed through the array for 1-5 minutes.

131. The method of any of embodiments 126-130, wherein flowing the first liquid comprises applying vacuum in the flow direction through the array.

132. The method of any of embodiments 126-131, wherein flowing the first liquid comprises applying pressure to the liquid in the flow direction through the array.

133. The method of any of embodiments 126-132, wherein flowing the first liquid comprises centrifuging the array.

134. The method of any of embodiments 126-133, wherein 85% of wells are occupied with a single cell.

135. The method of any of embodiments 126-134, wherein the concentration of cells in the first fluid is unknown.

136. The method of any of embodiments 126-135, wherein the concentration of cells in the first fluid exceeds the concentration that would be required for a Poisson distribution.

137. The method of any of embodiments 126-136, wherein the concentration of cells in the first fluid results in greater than 75% of wells being occupied by a cell.

138. The method of any of embodiments 126-137, wherein 95% of the wells are loaded with a single bead.

139. The method of any of embodiments 126-138, wherein the method further comprises sealing the array with an ultrafiltration membrane.

140. The method of any of embodiments 126-139, further comprising contacting the array with one or more lysis buffers to lyse the cells, and analyzing the protein and/or nucleic acid released from the lysed cells.

141. The method of embodiment 140, wherein the bead is a barcoded transcript capture bead and the RNA from the lysed cells in each well is captured on the bead present in the same well.

142. The method of embodiment 141, further comprising generating cDNA from the captured RNA such that the sequence of the bead barcode is incorporated into the cDNA.

143. The method of any of embodiments 125-138, wherein the first fluid comprises one or more beads and is flowed through (i) the array of wells of any one of embodiments 1-31 or 64-72 or (ii) the dry film of photoresist of any one of embodiments 32-43 or 64-72; and the method further comprises contacting the array with a second dry film of photoresist having a plurality of through-holes (e.g., a second bottomless microwell array).

144. The method of embodiment 143, wherein at least 90% of the wells of the first bottomless microwell array or of the dry film of photoresist are in fluid communication with a single through-hole of the second dry film of photoresist.

145. The method of embodiment 143 or 144, wherein the method further comprises flowing a second fluid comprising one or more cells through the array of wells or dry film of photoresist.

146. The method of embodiment 145, wherein flowing the second liquid comprises applying vacuum in the flow direction through the array.

147. The method of embodiment 145, wherein flowing the second liquid comprises applying pressure to the liquid in the flow direction through the array.

148. The method of embodiment 145, wherein flowing the second liquid comprises centrifuging the array.

149. The method of any of embodiment 144-148, wherein the method further comprises sealing the array with an ultrafiltration membrane.

150. The method of any of embodiment 144-149, further comprising contacting the array with one or more lysis buffers to lyse the cells, and analyzing the protein and/or nucleic acid released from the lysed cells.

151. The method of any of embodiment 144-150, wherein the bead is a barcoded transcript capture bead and the RNA from the lysed cells in each well is captured on the bead present in the same well.

152. The method of embodiment 151, further comprising generating cDNA from the captured transcripts such that the sequence of the bead barcode is incorporated into the cDNA.

153. A method comprising:
providing a microfluidic device comprising a first bottomless microwell array having an average well diameter of 15-100 microns and bonded to a first porous membrane having an average pore diameter of 80-1000 nanometers;
flowing a first fluid comprising a plurality of beads through the microfluidic device;
bonding the first bottomless microwell array bound to the first porous membrane to a second porous membrane having an average pore diameter of 80-1000 nanometers bonded to a second bottomless microwell array having an average well diameter of 1-10 microns; and
flowing a second fluid comprising a plurality of cells through the microfluidic device; wherein 80% of the wells of the first bottomless microwell array are occupied by a single bead.

154. A method comprising:
providing a microfluidic device comprising a first bottomless microwell array having an average well diameter of 1-10 microns and bonded to (a) a second bottomless microwell array having an average well diameter of 15-100 microns, and (b) a porous membrane having an average pore diameter of 80-1000 nanometers;
flowing a first fluid comprising a plurality of cells through the microfluidic device; and
exposing the microfluidic device to a second fluid comprising beads; wherein 80% of the wells of the first bottomless microwell array are occupied by a single cell 155. The method of embodiment 153 or 154, wherein at least 90% of the wells of the first bottomless microwell array are in contact with a single well of the second bottomless microwell array.

156. The method of any of embodiments 153-155, wherein the first and or second bottomless microwell array comprise a dry film of photoresist.

157. The method of any of embodiments 153-156, wherein 85% of wells of the second bottomless microwell array are occupied with a single cell and/or bead.

158. The method of any of embodiments 153-157, wherein the concentration of the plurality of cells in the first fluid is unknown.

159. The method of any of embodiments 153-158, wherein the concentration of the plurality of cells in the first fluid exceeds the concentration that would be required for a Poisson distribution.

Equivalents

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or"

should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method for producing a library of nucleic acids containing universal primer sites on the 5' and 3' end from input nucleic acids comprising:
  (a) providing a picowell array comprising a plurality of picowells,
  (b) contacting input nucleic acids with a pool of capture oligonucleotides in a picowell of the plurality of picowells, each capture oligonucleotide in the picowell containing a 5' universal primer site and a 3' target binding site complementary to a nucleotide sequence in an input nucleic acid, wherein the input nucleic acids comprise RNA, and wherein the 3' target binding site contained in the capture oligonucleotide comprises a poly(dT) sequence,
  (c) adding a DNA polymerase and thereby extending the capture oligonucleotides hybridized to the input nucleic acids, to form first strand cDNA nucleic acids each comprising the 5' universal primer site and a sequence that is complementary to one of the input nucleic acids, (d) contacting the first strand cDNA nucleic acids with a pool of second strand priming oligonucleotides, each consisting of a 5' universal primer site and a 3' target binding site complementary to a nucleotide sequence in the first strand cDNA nucleic acid, wherein each 3' target binding site of the second strand priming oligonucleotides consists of a random sequence, (e) adding a DNA polymerase and thereby extending the second strand priming oligonucleotides, to form second strand cDNA nucleic acids comprising 5' and 3' universal primer sites that flank nucleotide sequences present in the input nucleic acids, and (f) amplifying the second strand cDNA nucleic acids comprising 5' and 3' universal primer sites formed in step (e).

2. The method of claim 1, wherein each capture oligonucleotide comprises a barcode present between the 5' universal primer site and the 3' target binding site.

3. The method of claim 1, wherein the capture oligonucleotides are attached to a surface of a bead.

4. The method of claim 1, wherein the input nucleic acids are derived from a single cell.

5. The method of claim 1, wherein a crowding reagent is added in step (b), (c), (d) and/or (e).

6. The method of claim 1, wherein the random sequence in the 3' target binding site of the second strand priming oligonucleotide is 7, 8, 9, 10, 11, 12, 13, 14, or 15 nucleotides long.

7. The method of claim 1, further comprising pooling the content of a plurality of picowells into a single reaction volume after (b).

8. The method of claim 7, wherein (d) and (e) are performed in the single reaction volume.

9. The method of claim 7, wherein (c) is performed in the single reaction volume.

10. The method of claim 1, wherein the DNA polymerase added in (e) lacks both 5'-3' and 3'-5' exonuclease activity.

11. The method of claim 4, wherein the method further comprises loading the single cell to the picowell array, and wherein each picowell of the plurality of picowells comprises a functionalized surface comprising one or more nucleic acid barcodes.

12. The method of claim 11, wherein each nucleic acid barcode is unique relative to all other nucleic acid barcodes in the array or to a subset of other nucleic acid barcodes in the array.

13. The method of claim 11, wherein the location of each nucleic acid barcode in the array is known.

14. The method of claim 3, wherein each of the capture oligonucleotides in the picowell further comprises a bead barcode that is the same in each capture oligonucleotide of the picowell.

15. The method of claim 14, wherein the bead barcode identically labels the input nucleic acids derived from the same single cell.

16. The method of claim 3, further comprising separating the second strand cDNA nucleic acids by base-mediated DNA denaturation.

17. The method of claim 1, wherein the amplifying comprises PCR amplification.

* * * * *

SEQUENCE LISTING

```
<160> NUMBER OF SEQ ID NOS: 7

<210> SEQ ID NO 1
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (26)..(28)
<223> OTHER INFORMATION: n is a, c, g, t or u
<220> FEATURE:
<221> NAME/KEY: misc_feature
<222> LOCATION: (31)..(33)
<223> OTHER INFORMATION: n is a, c, g, t or u
<220> FEATURE:
<221> NAME/KEY: misc_feature
<222> LOCATION: (34)..(34)
<223> OTHER INFORMATION: b is c, g or t

<400> SEQUENCE: 1
aagcagtggt atcaacgcag agtgannngg nnnb                                34

<210> SEQ ID NO 2
<211> LENGTH: 49
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (18)..(27)
<223> OTHER INFORMATION: n is a, c, g, t or u
```

```
<400> SEQUENCE: 2
tttttttttt ttttttttnnn nnnnnnncaa ctctgcgttg ataccactg        49

<210> SEQ ID NO 3
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 3
aagcagtggt atcaacgcag agttg                                  25

<210> SEQ ID NO 4
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 4
aatgatacgg cgaccaccga gatctacacg cctgtccgcg gaagcagtgg tatcaacgca    60
gagtac                                                             66

<210> SEQ ID NO 5
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 5
gtctcgtggg ctcggagatg tgtataagag acagaagcag tggtatcaac gcagagttg    59

<210> SEQ ID NO 6
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 6
caagcagaag acggcatacg agattcgcct tagtctcgtg ggctcgg                47

<210> SEQ ID NO 7
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 7
gcctgtccgc ggaagcagtg gtatcaacgc agagtac                    37
```